United States Patent
Wang et al.

(10) Patent No.: US 11,299,550 B2
(45) Date of Patent: Apr. 12, 2022

(54) ANTI-CD73 ANTIBODIES AND USES THEREOF

(71) Applicant: Phanes Therapeutics, Inc., San Diego, CA (US)

(72) Inventors: Minghan Wang, San Diego, CA (US); Hui Zou, Dallas, TX (US); Fen Pei, San Diego, CA (US)

(73) Assignee: Phanes Therapeutics, Inc., San Diego, CA (US)

(*) Notice: Subject to any disclaimer, the term of this patent is extended or adjusted under 35 U.S.C. 154(b) by 92 days.

(21) Appl. No.: 15/733,540

(22) PCT Filed: Mar. 5, 2019

(86) PCT No.: PCT/US2019/020688
§ 371 (c)(1),
(2) Date: Aug. 24, 2020

(87) PCT Pub. No.: WO2019/173291
PCT Pub. Date: Sep. 12, 2019

(65) Prior Publication Data
US 2020/0399389 A1 Dec. 24, 2020

Related U.S. Application Data

(60) Provisional application No. 62/640,955, filed on Mar. 9, 2018, provisional application No. 62/721,044, filed on Aug. 22, 2018, provisional application No. 62/786,598, filed on Dec. 31, 2018.

(51) Int. Cl.
| | | |
|---|---|---|
| *C07H 21/04* | (2006.01) | |
| *C12P 21/06* | (2006.01) | |
| *C12N 15/87* | (2006.01) | |
| *C12N 1/20* | (2006.01) | |
| *C12N 15/74* | (2006.01) | |
| *A61K 39/395* | (2006.01) | |
| *A61K 39/00* | (2006.01) | |
| *C07K 16/00* | (2006.01) | |
| *C07K 16/28* | (2006.01) | |

(52) U.S. Cl.
CPC ...... *C07K 16/2896* (2013.01); *C07K 2317/24* (2013.01); *C07K 2317/74* (2013.01); *C07K 2317/76* (2013.01)

(58) Field of Classification Search
None
See application file for complete search history.

(56) References Cited

U.S. PATENT DOCUMENTS

| | | |
|---|---|---|
| 2014/0235833 A1 | 8/2014 | Sugioka |
| 2016/0129108 A1 | 5/2016 | Sachsenmeier |
| 2016/0145350 A1 | 5/2016 | Lonberg |
| 2016/0194407 A1 | 7/2016 | Hay |
| 2016/0272643 A1 | 9/2016 | Chaloin |
| 2017/0044203 A1 | 2/2017 | Cacatian |
| 2017/0253665 A1 | 9/2017 | Lonberg |
| 2018/0009899 A1 | 1/2018 | Griffin |

FOREIGN PATENT DOCUMENTS

| | | |
|---|---|---|
| WO | 2015049447 | 4/2015 |
| WO | 2015164573 | 10/2015 |
| WO | 2016055609 | 4/2016 |
| WO | 2016075099 | 5/2016 |
| WO | 2016081746 | 5/2016 |
| WO | 2016081748 | 5/2016 |
| WO | 2016131950 | 8/2016 |
| WO | 2017064043 | 4/2017 |
| WO | 2017100670 | 6/2017 |
| WO | 2017118613 | 7/2017 |
| WO | 2017152085 | 9/2017 |
| WO | 2018013611 | 1/2018 |

OTHER PUBLICATIONS

Antonioli et al., "Anti-CD 73 in Cancer Immunotherapy: Awakening New Opportunities", Trends in Cancer, vol. 2, No. 2, pp. 95-109, 2016.
Geoghegan et al., "Inhibition of CD 73 AMP hydrolysis by a therapeutic antibody with a dual, non-competitive mechanism of action", MAbs, vol. 8, No. 3, pp. 454-467, 2016.
International Preliminary Report on Patentability for PCT/US2019/020688, dated Sep. 15, 2020, 7 pages.
International Search Report and Written Opinion for PCT/US2019/020688, dated May 28, 2019, 10 pages.
Airas et al., "Differential Regulation and Function of CD73, a Glycosyl-Phosphatidylinositol-linked 70-kD Adhesion Molecule, on Lymphocytes and Endothelial Cells", J Cell Biol. 1997; 136(2):421-31.
Bours et al., "Adenosine 5'-triphosphate and adenosine as endogenous signaling molecules in immunity and inflammation", Pharmacol Ther 2006; 112:358-404.
Beavis et al., "CD73: a potent suppressor of antitumor immune responses", Trends Immunol 2012; 33:231-237.
Theresa L. Whiteside, "Targeting adenosine in cancer immunotherapy: a review of recent progress", Expert Rev. Anticancer Ther. 2017; 17(6):527-35.
Csoka et al., "Adenosine promotes alternative macrophage activation via A2A and A2B receptors", FASEB J 2012; 26:376-386.
Panther et al., "Adenosine affects expressioin of membrane molecules, cytokine and chemokine release, and the T-cell stimulatory capacity of human dendritic cells", Blood 2003; 101:3985-3990.
Hausler et al., "Ectonucleotidases CD39 and CD73 on OvCA cells are potent adenosine-generating enzymes responsible for adenosine receptor 2A-dependent suppression of T cell function and NK cell cytotoxicity", Cancer Immunol Immunother 2011; 60:1405-1418.
Hoskin et al., "Inhibition of T cell and natural killer cell function by adenosine and its contribution to immune evasion by tumor cells (Review)", Int J Oncol 2008; 32:527-535.

(Continued)

*Primary Examiner* — Maher M Haddad
(74) *Attorney, Agent, or Firm* — Ice Miller LLP

(57) ABSTRACT

Anti-CD73 antibodies and antigen-binding fragments thereof are described. Also described are nucleic acids encoding the antibodies, compositions comprising the antibodies, and methods of producing the antibodies and using the antibodies for treating or preventing diseases such as cancer.

20 Claims, 7 Drawing Sheets

Specification includes a Sequence Listing.

(56) References Cited

OTHER PUBLICATIONS

Jin et al., "CD73 on Tumor Cells Impairs Antitumor T-Cell Responses: A Novel Mechanism of Tumor-Induced Immune Suppression", Cancer Res 2010; 70:2245-2255.
Stagg et al., "CD73-Deficient Mice Have Increased Antitumor Immunity and Are Resistant to Experimental Metastasis", Cancer Res 2011; 71:2892-2900.
Hay et al., "Targeting CD73 in the tumor microenvironment with MEDI9447", Oncoimmunology Aug. 5(8):e1208875 (2016), 10 pages.
Luca Antonioli et al., "Switching off CD73: a way to boost the activity of conventional and targeted antineoplastic therapies", Drug Discovery Today, vol. 22, No. 11, pp. 1686-1696 (2017).

SEQUENCE LISTING

```
<160> NUMBER OF SEQ ID NOS: 299

<210> SEQ ID NO 1
<211> LENGTH: 120
<212> TYPE: PRT
<213> ORGANISM: Artificial Sequence
<220> FEATURE:
<223> OTHER INFORMATION: 37C7A Heavy Chain Variable Region

<400> SEQUENCE: 1

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30
```

Gly Met Gly Val Thr Trp Ile Arg Gln Pro Ser Gly Lys Gly Leu Glu
            35                  40                  45

Trp Leu Ala His Ile Trp Trp Asp Asp Met Tyr Tyr Asn Pro Ala
 50                  55                  60

Leu Lys Ser Arg Leu Thr Ile Ser Lys Asp Thr Ser Lys Asn Gln Val
65                  70                  75                  80

Phe Leu Lys Ile Ala Asn Val Asp Thr Ala Asp Thr Ala Thr Tyr Tyr
                85                  90                  95

Cys Ala Arg Ser Pro Ile Thr Thr Val Val Ala Asp Tyr Trp Gly Gln
            100                 105                 110

Gly Ser Thr Leu Thr Val Ser Ser
            115                 120

<210> SEQ ID NO 2
<211> LENGTH: 112
<212> TYPE: PRT
<213> ORGANISM: Artificial Sequence
<220> FEATURE:
<223> OTHER INFORMATION: 37C7A Light Chain Variable Region

<400> SEQUENCE: 2

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Asn Leu Val His Ser
            20                  25                  30

Tyr Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Asn
                85                  90                  95

Thr His Val Pro Trp Thr Phe Gly Gly Thr Lys Leu Glu Ile Gln
            100                 105                 110

<210> SEQ ID NO 3
<211> LENGTH: 121
<212> TYPE: PRT
<213> ORGANISM: Artificial Sequence
<220> FEATURE:
<223> OTHER INFORMATION: 38C16A Heavy Chain Variable Region

<400> SEQUENCE: 3

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
            35                  40                  45

Gly Glu Ile Leu Pro Gly Ser Gly Ser Thr Asn Tyr Asn Glu Lys Phe
 50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asp Tyr Phe Gly Ser Ser Tyr Arg Gly Pro Tyr Trp Gly
            100                 105                 110

```
Gln Gly Thr Leu Val Thr Val Ser Ala
        115                 120

<210> SEQ ID NO 4
<211> LENGTH: 112
<212> TYPE: PRT
<213> ORGANISM: Artificial Sequence
<220> FEATURE:
<223> OTHER INFORMATION: 38C16A Light Chain Variable Region

<400> SEQUENCE: 4

Asp Val Val Met Thr Gln Thr Pro Leu Thr Leu Ser Val Thr Ile Gly
1               5                   10                  15

Gln Pro Ala Ser Ile Ser Cys Lys Ser Gln Ser Leu Leu Asp Ser
            20                  25                  30

Asp Gly Arg Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro His Thr Phe Gly Gly Gly Thr Lys Leu Glu Ile Lys
            100                 105                 110

<210> SEQ ID NO 5
<211> LENGTH: 121
<212> TYPE: PRT
<213> ORGANISM: Artificial Sequence
<220> FEATURE:
<223> OTHER INFORMATION: 39G8A Heavy Chain Variable Region

<400> SEQUENCE: 5

Gln Val Gln Leu Gln Pro Gly Ala Glu Leu Val Met Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asp Pro Ser Gly Gly Tyr Thr Asn Tyr Asn Gln Lys Phe
    50                  55                  60

Lys Gly Lys Ser Thr Leu Thr Val Asp Lys Ser Ser Ser Thr Ala Tyr
65                  70                  75                  80

Met Gln Leu Ser Arg Leu Thr Ser Glu Asp Ser Ala Val Tyr Tyr Cys
                85                  90                  95

Ala Arg Asn Tyr Tyr Tyr Gly Ser Ser Gly Thr Met Asp Tyr Trp Gly
            100                 105                 110

Gln Gly Thr Ser Val Thr Val Ser Ser
        115                 120

<210> SEQ ID NO 6
<211> LENGTH: 113
<212> TYPE: PRT
<213> ORGANISM: Artificial Sequence
<220> FEATURE:
<223> OTHER INFORMATION: 39G8A Light Chain Variable Region

<400> SEQUENCE: 6
```

-continued

```
Asp Ile Val Met Thr Gln Ser Pro Ser Ser Leu Ala Met Ser Val Gly
  1               5                   10                  15

Gln Lys Val Thr Met Ser Cys Lys Ser Ser Gln Ser Leu Leu Asn Ser
             20                  25                  30

Ser Asn Gln Lys Asn Tyr Leu Ala Trp Tyr Gln Gln Lys Pro Gly Gln
         35                  40                  45

Ser Pro Lys Leu Leu Val Tyr Phe Ala Ser Thr Arg Glu Ser Gly Val
     50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                 85                  90                  95

His Tyr Ser Thr Pro Tyr Thr Phe Gly Gly Gly Thr Lys Leu Glu Ile
            100                 105                 110

Lys
```

<210> SEQ ID NO 7
<211> LENGTH: 121
<212> TYPE: PRT
<213> ORGANISM: Artificial Sequence
<220> FEATURE:
<223> OTHER INFORMATION: 43E8A Heavy Chain Variable Region

<400> SEQUENCE: 7

```
Gln Val Gln Leu Gln Gln Ser Gly Ala Glu Leu Met Lys Pro Gly Ala
  1               5                   10                  15

Ser Val Lys Ile Ser Cys Lys Ala Thr Gly Tyr Thr Phe Ser Asn Tyr
             20                  25                  30

Trp Ile Glu Trp Val Lys Gln Arg Pro Gly His Gly Leu Glu Trp Ile
         35                  40                  45

Gly Glu Ile Leu Pro Gly Asn Val Ile Thr Asn Tyr Asn Glu Lys Phe
     50                  55                  60

Lys Gly Lys Ala Thr Phe Thr Ala Asp Thr Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Ala Arg Arg Gly Asp Asp Gly Tyr Leu Tyr Ala Met Asp Tyr Trp Gly
            100                 105                 110

Gln Gly Thr Ser Val Thr Val Ser Ser
            115                 120
```

<210> SEQ ID NO 8
<211> LENGTH: 111
<212> TYPE: PRT
<213> ORGANISM: Artificial Sequence
<220> FEATURE:
<223> OTHER INFORMATION: 43E8A Light Chain Variable Region

<400> SEQUENCE: 8

```
Asp Ile Val Leu Thr Gln Ser Pro Ala Ser Leu Ala Val Ser Leu Gly
  1               5                   10                  15

Gln Arg Ala Thr Ile Ser Cys Arg Ala Ser Glu Ser Val Asp Asn Tyr
             20                  25                  30

Gly Ile Ser Phe Met Asn Trp Phe Gln Gln Lys Pro Gly Gln Pro Pro
         35                  40                  45

Lys Leu Leu Ile Tyr Ala Ala Ser Asn Gln Gly Ser Gly Val Pro Ala
     50                  55                  60
```

Arg Phe Ser Gly Ser Gly Ser Gly Thr Asp Phe Ser Leu Asn Ile His
 65                  70                  75                  80

Pro Met Glu Glu Asp Asp Thr Ala Met Tyr Phe Cys Gln Gln Ser Lys
                 85                  90                  95

Glu Val Pro Phe Thr Phe Gly Ser Gly Thr Lys Leu Glu Ile Lys
            100                 105                 110

<210> SEQ ID NO 9
<211> LENGTH: 123
<212> TYPE: PRT
<213> ORGANISM: Artificial Sequence
<220> FEATURE:
<223> OTHER INFORMATION: 46J3A Heavy Chain Variable Region

<400> SEQUENCE: 9

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met His Trp Val Lys Gln Lys Pro Gly Gln Gly Leu Glu Trp Ile
        35                  40                  45

Gly Glu Ile Tyr Pro Gly Ser Gly Asn Thr Tyr Tyr Asn Glu Lys Phe
 50                  55                  60

Lys Gly Lys Ala Thr Leu Thr Ala Asp Arg Ser Ser Thr Val Tyr
 65                  70                  75                  80

Met Leu Leu Ser Ser Leu Thr Ser Glu Asp Ser Ala Val Tyr Phe Cys
                 85                  90                  95

Ala Arg Tyr Trp Asp Tyr Tyr Gly Ser Thr Tyr Gly Tyr Phe Asp Val
            100                 105                 110

Trp Gly Ala Gly Thr Thr Val Thr Val Ser Ser
        115                 120

<210> SEQ ID NO 10
<211> LENGTH: 107
<212> TYPE: PRT
<213> ORGANISM: Artificial Sequence
<220> FEATURE:
<223> OTHER INFORMATION: 46J3A Light Chain Variable Region

<400> SEQUENCE: 10

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Asn Ile Ser Lys Tyr
            20                  25                  30

Leu Ala Trp Tyr Gln Glu Ile Pro Gly Lys Thr Tyr Asn Leu Leu Ile
        35                  40                  45

Tyr Ser Gly Ser Thr Leu Gln Ser Gly Ile Pro Ser Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His Asn Glu Tyr Pro Phe
                 85                  90                  95

Thr Phe Gly Ser Gly Thr Lys Leu Glu Ile Lys
            100                 105

<210> SEQ ID NO 11
<211> LENGTH: 117
<212> TYPE: PRT
<213> ORGANISM: Artificial Sequence

```
<220> FEATURE:
<223> OTHER INFORMATION: 46O19A Heavy Chain Variable Region

<400> SEQUENCE: 11

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
                20                  25                  30

Asn Met His Trp Val Lys Gln Ser His Gly Lys Ser Leu Glu Trp Ile
            35                  40                  45

Gly Tyr Ile Asn Pro Asn Asn Gly Gly Thr Ser Tyr Asn Gln Lys Phe
        50                  55                  60

Lys Gly Lys Ala Thr Leu Thr Val Asn Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Tyr Phe Trp Tyr Phe Asp Val Trp Gly Thr Gly Thr Thr
                100                 105                 110

Val Thr Val Ser Ser
            115

<210> SEQ ID NO 12
<211> LENGTH: 113
<212> TYPE: PRT
<213> ORGANISM: Artificial Sequence
<220> FEATURE:
<223> OTHER INFORMATION: 46O19A Light Chain Variable Region

<400> SEQUENCE: 12

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Glu Lys Pro Gly Gln
            35                  40                  45

Pro Pro Lys Val Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
                100                 105                 110

Lys

<210> SEQ ID NO 13
<211> LENGTH: 113
<212> TYPE: PRT
<213> ORGANISM: Artificial Sequence
<220> FEATURE:
<223> OTHER INFORMATION: 47H24A Heavy Chain Variable Region

<400> SEQUENCE: 13

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
                20                  25                  30

Gly Val His Trp Val Arg Gln Ser Pro Gly Lys Gly Leu Glu Trp Leu
```

```
                35                  40                  45
Gly Val Ile Trp Ser Gly Gly Ser Thr Asp Tyr Asn Ala Ala Phe Ile
        50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Ser Gln Tyr Val Ala Tyr Trp Gly Gln Gly Thr Leu Val Thr Val Ser
                100                 105                 110

Thr

<210> SEQ ID NO 14
<211> LENGTH: 107
<212> TYPE: PRT
<213> ORGANISM: Artificial Sequence
<220> FEATURE:
<223> OTHER INFORMATION: 47H24A Light Chain Variable Region

<400> SEQUENCE: 14

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Arg
                20                  25                  30

Leu Thr Trp Leu Gln Gln Glu Pro Asp Gly Thr Ile Lys Arg Leu Ile
            35                  40                  45

Tyr Ala Thr Ser Ser Leu Asp Ser Gly Val Pro Lys Arg Phe Ser Gly
        50                  55                  60

Ser Arg Ser Gly Ser Asp Tyr Ser Leu Thr Ile Ser Ser Leu Glu Ser
65                  70                  75                  80

Glu Asp Phe Val Asp Tyr Phe Cys Leu Gln Tyr Ala Ser Ser Pro Phe
                85                  90                  95

Thr Phe Gly Ser Gly Thr Lys Leu Glu Ile Lys
            100                 105

<210> SEQ ID NO 15
<211> LENGTH: 121
<212> TYPE: PRT
<213> ORGANISM: Artificial Sequence
<220> FEATURE:
<223> OTHER INFORMATION: 49O5A Heavy Chain Variable Region

<400> SEQUENCE: 15

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Asn Ile Asn Pro Ser Asn Gly Gly Thr Asn Tyr Asn Glu Lys Phe
        50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Lys Ser Asn Tyr Gly Tyr Tyr Ala Met Asp Tyr Trp Gly
                100                 105                 110

Gln Gly Thr Ser Val Thr Val Ser Ser
```

-continued

```
                115                 120

<210> SEQ ID NO 16
<211> LENGTH: 107
<212> TYPE: PRT
<213> ORGANISM: Artificial Sequence
<220> FEATURE:
<223> OTHER INFORMATION: 4905A Light Chain Variable Region

<400> SEQUENCE: 16

Asp Ile Gln Met Thr Gln Ser Ser Ser Tyr Leu Ser Val Ser Leu Gly
1               5                   10                  15

Gly Arg Val Thr Ile Thr Cys Glu Ala Ser Asp His Ile Asp Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Ser Pro Phe
                85                  90                  95

Thr Phe Gly Ser Gly Thr Lys Leu Glu Ile Lys
            100                 105

<210> SEQ ID NO 17
<211> LENGTH: 124
<212> TYPE: PRT
<213> ORGANISM: Artificial Sequence
<220> FEATURE:
<223> OTHER INFORMATION: 50B10A Heavy Chain Variable Region

<400> SEQUENCE: 17

Gln Val Gln Leu Gln Gln Pro Gly Ala Glu Leu Val Lys Pro Gly Ala
1               5                   10                  15

Ser Val Lys Leu Ser Cys Lys Ser Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Glu Gly Arg Val Tyr Tyr Asp Tyr Phe Tyr Ala Met Asp
            100                 105                 110

Tyr Trp Gly Gln Gly Thr Ser Val Thr Val Ser Ser
        115                 120

<210> SEQ ID NO 18
<211> LENGTH: 107
<212> TYPE: PRT
<213> ORGANISM: Artificial Sequence
<220> FEATURE:
<223> OTHER INFORMATION: 50B10A Light Chain Variable Region

<400> SEQUENCE: 18

Asp Ile Gln Met Thr Gln Thr Thr Ser Ser Leu Ser Ala Ser Leu Gly
1               5                   10                  15
```

```
Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 19
<211> LENGTH: 117
<212> TYPE: PRT
<213> ORGANISM: Artificial Sequence
<220> FEATURE:
<223> OTHER INFORMATION: 50H17A Heavy Chain Variable Region

<400> SEQUENCE: 19

Gln Val Gln Leu Gln Gln Ser Gly Ala Glu Leu Val Arg Pro Gly Thr
 1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Val Ile Asn Pro Gly Ser Gly Gly Thr Asn Tyr Asn Glu Lys Phe
 50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                85                  90                  95

Ala Arg Asp Tyr Tyr Trp Tyr Phe Asp Val Trp Gly Thr Gly Thr Thr
            100                 105                 110

Val Thr Val Ser Ser
        115

<210> SEQ ID NO 20
<211> LENGTH: 113
<212> TYPE: PRT
<213> ORGANISM: Artificial Sequence
<220> FEATURE:
<223> OTHER INFORMATION: 50H17A Light Chain Variable Region

<400> SEQUENCE: 20

Asp Ile Val Met Thr Gln Ser Pro Ser Ser Leu Thr Val Thr Ala Gly
 1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Val Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
```

85                  90                  95
Asp Tyr Ser Tyr Pro Leu Thr Phe Gly Ala Gly Thr Lys Leu Glu Leu
                    100                 105                 110

Lys

<210> SEQ ID NO 21
<211> LENGTH: 120
<212> TYPE: PRT
<213> ORGANISM: Artificial Sequence
<220> FEATURE:
<223> OTHER INFORMATION: 50E16A Heavy Chain Variable Region

<400> SEQUENCE: 21

Glu Leu Ala Arg Pro Trp Ala Ser Val Lys Ile Ser Cys Gln Ala Phe
1               5                   10                  15

Tyr Thr Phe Ser Arg Arg Met His Phe Ala Ile Arg Asp Thr Asn Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Val Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Thr Tyr Tyr Ser Asn Tyr Gly Gly Ala Met Asp Tyr Trp Gly Gln
            100                 105                 110

Gly Thr Ser Val Thr Val Ser Ser
        115                 120

<210> SEQ ID NO 22
<211> LENGTH: 107
<212> TYPE: PRT
<213> ORGANISM: Artificial Sequence
<220> FEATURE:
<223> OTHER INFORMATION: 50E16 Light Chain Variable Region

<400> SEQUENCE: 22

Asp Ile Val Met Thr Gln Phe His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 23
<211> LENGTH: 117
<212> TYPE: PRT
<213> ORGANISM: Artificial Sequence
<220> FEATURE:
<223> OTHER INFORMATION: 50F1A Heavy Chain Variable Region

<400> SEQUENCE: 23

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Ile Phe Trp Ala Met Asp Tyr Trp Gly Gln Gly Thr Ser
            100                 105                 110

Val Thr Val Ser Ser
        115

<210> SEQ ID NO 24
<211> LENGTH: 113
<212> TYPE: PRT
<213> ORGANISM: Artificial Sequence
<220> FEATURE:
<223> OTHER INFORMATION: 50F1A Light Chain Variable Region

<400> SEQUENCE: 24

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 25
<211> LENGTH: 117
<212> TYPE: PRT
<213> ORGANISM: Artificial Sequence
<220> FEATURE:
<223> OTHER INFORMATION: 54I14A Heavy Chain Variable Region

<400> SEQUENCE: 25

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
        35                  40                  45

```
Gly Ala Ile Tyr Pro Gly Asn Gly Asp Thr Ser Tyr Asn Gln Lys Phe
        50                  55                  60

Lys Gly Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Tyr Asp Tyr Asp Ala Met Asp Tyr Trp Gly Gln Gly Thr Ser
            100                 105                 110

Val Thr Val Ser Ser
            115

<210> SEQ ID NO 26
<211> LENGTH: 107
<212> TYPE: PRT
<213> ORGANISM: Artificial Sequence
<220> FEATURE:
<223> OTHER INFORMATION: 54I14A Light Chain Variable Region

<400> SEQUENCE: 26

Asp Ile Gln Met Thr Gln Ser Pro Ala Ser Leu Ser Ala Ser Val Gly
  1               5                  10                  15

Glu Thr Val Thr Ile Thr Cys Arg Ala Ser Glu Asn Ile Tyr Ser Tyr
             20                  25                  30

Phe Ala Trp Tyr Gln Gln Lys Gln Gly Lys Ser Pro Gln Leu Leu Val
         35                  40                  45

Tyr Asn Ala Lys Thr Leu Ala Glu Gly Val Pro Ser Arg Phe Ser Gly
     50                  55                  60

Ser Gly Ser Gly Thr Gln Phe Ser Leu Lys Ile Asn Ser Leu Gln Pro
 65                  70                  75                  80

Glu Asp Phe Gly Ser Tyr Tyr Cys Gln His His Tyr Gly Thr Pro Phe
                 85                  90                  95

Thr Phe Gly Ser Gly Thr Lys Leu Glu Ile Lys
            100                 105

<210> SEQ ID NO 27
<211> LENGTH: 119
<212> TYPE: PRT
<213> ORGANISM: Artificial Sequence
<220> FEATURE:
<223> OTHER INFORMATION: 52K11A Heavy Chain Variable Region

<400> SEQUENCE: 27

Glu Ile Gln Leu Gln Gln Ser Gly Ala Glu Leu Val Lys Pro Gly Ala
  1               5                  10                  15

Ser Val Lys Ile Ser Cys Lys Ala Ser Gly Tyr Ser Phe Thr Gly Tyr
             20                  25                  30

Asn Met Asn Trp Val Lys Gln Ser His Gly Lys Ser Leu Glu Trp Ile
         35                  40                  45

Gly Asn Ile Asn Pro Tyr Tyr Gly Ser Thr Ser Tyr Asn Gln Lys Phe
     50                  55                  60

Lys Gly Lys Ala Thr Leu Thr Val Asp Lys Ser Ser Ser Thr Ala Tyr
 65                  70                  75                  80

Met Gln Leu Asn Ser Leu Thr Ser Lys Asp Ser Ala Val Tyr Tyr Cys
                 85                  90                  95

Ala Gly Ser Ser Tyr Val Asp Tyr Ala Met Asp Tyr Trp Gly Gln Gly
            100                 105                 110

Thr Ser Val Thr Val Ser Ser
            115
```

<210> SEQ ID NO 28
<211> LENGTH: 112
<212> TYPE: PRT
<213> ORGANISM: Artificial Sequence
<220> FEATURE:
<223> OTHER INFORMATION: 52K11A Light Chain Variable Region

<400> SEQUENCE: 28

```
Asp Ile Val Met Thr Gln Ala Ala Ile Ser Asn Pro Val Thr Leu Gly
1               5                   10                  15

Thr Ser Ala Ser Ile Ser Cys Ser Ser Asn Lys Ser Leu Leu His Ser
            20                  25                  30

Asn Asp Ile Thr Tyr Leu Tyr Trp Tyr Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Met
                85                  90                  95

Leu Glu Arg Pro Trp Thr Phe Gly Gly Gly Thr Lys Leu Glu Ile Lys
            100                 105                 110
```

<210> SEQ ID NO 29
<211> LENGTH: 118
<212> TYPE: PRT
<213> ORGANISM: Artificial Sequence
<220> FEATURE:
<223> OTHER INFORMATION: 53H21A Heavy Chain Variable Region

<400> SEQUENCE: 29

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Ile Pro Tyr Asn Asp Gly Thr Lys Tyr Asn Glu Lys Phe
    50                  55                  60

Glu Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Trp Gly Asn Trp Asp Tyr Phe Asp Tyr Trp Gly Gln Gly Thr
            100                 105                 110

Thr Leu Thr Val Ser Ser
        115
```

<210> SEQ ID NO 30
<211> LENGTH: 106
<212> TYPE: PRT
<213> ORGANISM: Artificial Sequence
<220> FEATURE:
<223> OTHER INFORMATION: 53H21A Light Chain Variable Region

<400> SEQUENCE: 30

```
Gln Ile Val Leu Thr Gln Ser Pro Ala Leu Met Ser Ala Ser Pro Gly
1               5                   10                  15
```

Glu Lys Val Thr Met Thr Cys Ser Ala Ser Ser Val Ser Tyr Met
              20                  25                  30

Tyr Trp Tyr Gln Gln Lys Pro Arg Ser Ser Pro Lys Pro Trp Ile Tyr
         35                  40                  45

Leu Thr Ser Asn Leu Ala Ser Gly Val Pro Ala Arg Phe Ser Gly Ser
     50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Trp Thr
                 85                  90                  95

Phe Gly Gly Gly Thr Lys Leu Glu Ile Lys
            100                 105

<210> SEQ ID NO 31
<211> LENGTH: 119
<212> TYPE: PRT
<213> ORGANISM: Artificial Sequence
<220> FEATURE:
<223> OTHER INFORMATION: 53I12A Heavy Chain Variable Region

<400> SEQUENCE: 31

Gln Val Gln Leu Gln Gln Pro Gly Ala Glu Leu Val Lys Pro Gly Ala
 1               5                  10                  15

Ser Val Lys Leu Ser Cys Lys Ala Pro Gly Tyr Thr Phe Thr Ser Tyr
             20                  25                  30

Trp Ile Asn Trp Val Lys Gln Arg Pro Gly Gln Gly Leu Glu Trp Ile
         35                  40                  45

Gly Asn Ile Tyr Ala Gly Ser Ser Ser Asn Tyr Asn Glu Lys Phe
     50                  55                  60

Lys Ser Lys Ala Thr Leu Thr Val Asp Thr Ser Ser Ser Thr Ala Tyr
 65                  70                  75                  80

Met Gln Leu Ser Ser Leu Thr Ser Asp Asp Ser Ala Val Tyr Tyr Cys
                 85                  90                  95

Ala Arg Ser Gly His Gly Tyr Asp Gly Phe Ala Tyr Trp Gly Gln Gly
            100                 105                 110

Thr Leu Val Thr Val Ser Ala
        115

<210> SEQ ID NO 32
<211> LENGTH: 107
<212> TYPE: PRT
<213> ORGANISM: Artificial Sequence
<220> FEATURE:
<223> OTHER INFORMATION: 53I12A Light Chain Variable Region

<400> SEQUENCE: 32

Asp Ile Gln Met Thr Gln Thr Thr Ser Ser Leu Ser Ala Ser Leu Gly
 1               5                  10                  15

Asp Arg Val Thr Ile Ser Cys Ser Ala Ser Gln Gly Ile Ser Asn Tyr
             20                  25                  30

Leu Asn Trp Tyr Gln Gln Lys Pro Asp Gly Thr Val Lys Leu Leu Ile
         35                  40                  45

Tyr Tyr Thr Ser Ser Leu His Ser Gly Val Pro Ser Arg Phe Ser Gly
     50                  55                  60

Ser Gly Ser Gly Thr Asp Tyr Ser Leu Thr Ile Ser Asn Leu Glu Pro
 65                  70                  75                  80

Glu Asp Ile Ala Thr Tyr Tyr Cys Gln Gln Tyr Ser Lys Leu Pro Arg
                 85                  90                  95

Thr Phe Gly Gly Gly Thr Lys Leu Glu Ile Lys
            100                 105

<210> SEQ ID NO 33
<211> LENGTH: 121
<212> TYPE: PRT
<213> ORGANISM: Artificial Sequence
<220> FEATURE:
<223> OTHER INFORMATION: 60A9A Heavy Chain Variable Region

<400> SEQUENCE: 33

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Asp Thr Tyr Tyr Ser Gly Lys Phe
    50                  55                  60

Lys Gly Lys Ala Thr Leu Thr Ala Ala Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Glu Ala Ile Tyr Tyr Gly Asn Tyr Val Phe Thr Tyr Trp Gly
            100                 105                 110

Gln Gly Thr Leu Val Thr Val Ser Ala
        115                 120

<210> SEQ ID NO 34
<211> LENGTH: 113
<212> TYPE: PRT
<213> ORGANISM: Artificial Sequence
<220> FEATURE:
<223> OTHER INFORMATION: 60A9A Light Chain Variable Region

<400> SEQUENCE: 34

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Asp Ser Gly Val
    50                  55                  60

Pro Asp Arg Phe Ile Gly Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys

<210> SEQ ID NO 35
<211> LENGTH: 120
<212> TYPE: PRT
<213> ORGANISM: Artificial Sequence
<220> FEATURE:
<223> OTHER INFORMATION: 39J9A Heavy Chain Variable Region

<400> SEQUENCE: 35

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Ile Lys Gln Arg Pro Gly Gln Gly Leu Glu Trp Ile
        35                  40                  45

Gly Leu Ile Asn Pro Gly Ser Gly Gly Thr Asn Tyr Ile Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Arg Gly Asp Tyr Tyr Gly Asn Pro Phe Asp Tyr Trp Gly Gln
            100                 105                 110

Gly Thr Thr Leu Thr Val Ser Ser
        115                 120

<210> SEQ ID NO 36
<211> LENGTH: 107
<212> TYPE: PRT
<213> ORGANISM: Artificial Sequence
<220> FEATURE:
<223> OTHER INFORMATION: 39J9A Light Chain Variable Region

<400> SEQUENCE: 36

Asp Ile Gln Met Thr Gln Ser Pro Ala Ser Leu Ala Ala Ser Val Gly
1               5                   10                  15

Glu Thr Val Thr Ile Thr Cys Arg Ala Ser Glu Asn Ile Tyr Tyr Ser
            20                  25                  30

Leu Ala Trp Tyr Gln Gln Lys Gln Gly Lys Ser Pro Gln Leu Leu Ile
        35                  40                  45

Tyr Asn Ala Asp Thr Leu Glu Asp Gly Val Pro Ser Arg Phe Ser Gly
    50                  55                  60

Ser Gly Ser Gly Thr Gln Tyr Ser Met Lys Ile Asn Ser Met Gln Pro
65                  70                  75                  80

Glu Asp Thr Ala Thr Tyr Phe Cys Lys Gln Ala Tyr Asp Val Pro Leu
                85                  90                  95

Thr Phe Gly Ala Gly Thr Lys Leu Glu Leu Lys
            100                 105

<210> SEQ ID NO 37
<211> LENGTH: 121
<212> TYPE: PRT
<213> ORGANISM: Artificial Sequence
<220> FEATURE:
<223> OTHER INFORMATION: 49H8A Heavy Chain Variable Region

<400> SEQUENCE: 37

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30

Trp Met Gln Trp Val Arg Gln Arg Pro Gly Gln Gly Leu Glu Trp Ile
        35                  40                  45

Gly Glu Ile Asp Pro Ser Asp Asn Tyr Thr His Tyr Asn Gln Lys Phe
    50                  55                  60

-continued

Lys Gly Glu Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Gly Tyr Tyr Gly Tyr Ser Pro Ser Trp Phe Ala Tyr Trp Gly
            100                 105                 110

Gln Gly Thr Leu Val Thr Val Ser Ala
            115                 120

<210> SEQ ID NO 38
<211> LENGTH: 106
<212> TYPE: PRT
<213> ORGANISM: Artificial Sequence
<220> FEATURE:
<223> OTHER INFORMATION: 49H8A Light Chain Variable Region

<400> SEQUENCE: 38

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asn Pro Pro Thr
                85                  90                  95

Phe Gly Ser Gly Thr Lys Leu Glu Ile Lys
            100                 105

<210> SEQ ID NO 39
<211> LENGTH: 117
<212> TYPE: PRT
<213> ORGANISM: Artificial Sequence
<220> FEATURE:
<223> OTHER INFORMATION: 51B10A Heavy Chain Variable Region

<400> SEQUENCE: 39

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Val Lys Ser Leu Glu Trp Ile
        35                  40                  45

Gly Arg Ile Asn Pro Tyr Ser Gly Ala Thr Asn Ser Asn Gln Asn Phe
    50                  55                  60

Lys Asp Lys Ala Ser Leu Thr Val Asp Lys Ser Ser Thr Ala Tyr
65                  70                  75                  80

Met Glu Leu His Ser Leu Thr Ser Glu Asp Ser Ala Val Tyr Tyr Cys
            85                  90                  95

Ala Arg Ser Tyr Tyr Gly Ala Met Asp Tyr Trp Gly Gln Gly Thr Ser
            100                 105                 110

Val Thr Val Ser Ser
        115

<210> SEQ ID NO 40

<211> LENGTH: 107
<212> TYPE: PRT
<213> ORGANISM: Artificial Sequence
<220> FEATURE:
<223> OTHER INFORMATION: 51B10A Light Chain Variable Region

<400> SEQUENCE: 40

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Leu
                85                  90                  95

Thr Phe Gly Ala Gly Thr Lys Leu Glu Leu Lys
            100                 105

<210> SEQ ID NO 41
<211> LENGTH: 10
<212> TYPE: PRT
<213> ORGANISM: Artificial Sequence
<220> FEATURE:
<223> OTHER INFORMATION: 37C7A HC CDR1

<400> SEQUENCE: 41

Gly Phe Ser Leu Ser Thr Phe Gly Met Gly
1               5                   10

<210> SEQ ID NO 42
<211> LENGTH: 7
<212> TYPE: PRT
<213> ORGANISM: Artificial Sequence
<220> FEATURE:
<223> OTHER INFORMATION: 37C7A HC CDR2

<400> SEQUENCE: 42

Ile Trp Trp Asp Asp Asp Met
1               5

<210> SEQ ID NO 43
<211> LENGTH: 12
<212> TYPE: PRT
<213> ORGANISM: Artificial Sequence
<220> FEATURE:
<223> OTHER INFORMATION: 37C7A HC CDR3

<400> SEQUENCE: 43

Ala Arg Ser Pro Ile Thr Thr Val Val Ala Asp Tyr
1               5                   10

<210> SEQ ID NO 44
<211> LENGTH: 8
<212> TYPE: PRT
<213> ORGANISM: Artificial Sequence
<220> FEATURE:
<223> OTHER INFORMATION: 38C16A HC CDR1

<400> SEQUENCE: 44

Gly Tyr Thr Phe Ser Ser Tyr Trp

```
<210> SEQ ID NO 45
<211> LENGTH: 8
<212> TYPE: PRT
<213> ORGANISM: Artificial Sequence
<220> FEATURE:
<223> OTHER INFORMATION: 38C16A HC CDR2

<400> SEQUENCE: 45

Ile Leu Pro Gly Ser Gly Ser Thr
1               5

<210> SEQ ID NO 46
<211> LENGTH: 14
<212> TYPE: PRT
<213> ORGANISM: Artificial Sequence
<220> FEATURE:
<223> OTHER INFORMATION: 38C16A HC CDR3

<400> SEQUENCE: 46

Ala Arg Gly Asp Tyr Phe Gly Ser Ser Tyr Arg Gly Pro Tyr
1               5                   10

<210> SEQ ID NO 47
<211> LENGTH: 8
<212> TYPE: PRT
<213> ORGANISM: Artificial Sequence
<220> FEATURE:
<223> OTHER INFORMATION: 39G8A HC CDR1

<400> SEQUENCE: 47

Gly Tyr Thr Phe Thr Ser Tyr Trp
1               5

<210> SEQ ID NO 48
<211> LENGTH: 8
<212> TYPE: PRT
<213> ORGANISM: Artificial Sequence
<220> FEATURE:
<223> OTHER INFORMATION: 39G8A HC CDR2

<400> SEQUENCE: 48

Ile Asp Pro Ser Gly Gly Tyr Thr
1               5

<210> SEQ ID NO 49
<211> LENGTH: 14
<212> TYPE: PRT
<213> ORGANISM: Artificial Sequence
<220> FEATURE:
<223> OTHER INFORMATION: 39G8A HC CDR3

<400> SEQUENCE: 49

Ala Arg Asn Tyr Tyr Tyr Gly Ser Ser Gly Thr Met Asp Tyr
1               5                   10

<210> SEQ ID NO 50
<211> LENGTH: 8
<212> TYPE: PRT
<213> ORGANISM: Artificial Sequence
<220> FEATURE:
<223> OTHER INFORMATION: 43E8A HC CDR1

<400> SEQUENCE: 50

Gly Tyr Thr Phe Ser Asn Tyr Trp
1               5
```

```
<210> SEQ ID NO 51
<211> LENGTH: 8
<212> TYPE: PRT
<213> ORGANISM: Artificial Sequence
<220> FEATURE:
<223> OTHER INFORMATION: 43E8A HC CDR2

<400> SEQUENCE: 51

Ile Leu Pro Gly Asn Val Ile Thr
1               5

<210> SEQ ID NO 52
<211> LENGTH: 14
<212> TYPE: PRT
<213> ORGANISM: Artificial Sequence
<220> FEATURE:
<223> OTHER INFORMATION: 43E8A HC CDR3

<400> SEQUENCE: 52

Ala Arg Arg Gly Asp Asp Gly Tyr Leu Tyr Ala Met Asp Tyr
1               5                   10

<210> SEQ ID NO 53
<211> LENGTH: 8
<212> TYPE: PRT
<213> ORGANISM: Artificial Sequence
<220> FEATURE:
<223> OTHER INFORMATION: 46J3A HC CDR1

<400> SEQUENCE: 53

Gly Tyr Thr Phe Thr Asp Tyr Tyr
1               5

<210> SEQ ID NO 54
<211> LENGTH: 8
<212> TYPE: PRT
<213> ORGANISM: Artificial Sequence
<220> FEATURE:
<223> OTHER INFORMATION: 46J3A HC CDR2

<400> SEQUENCE: 54

Ile Tyr Pro Gly Ser Gly Asn Thr
1               5

<210> SEQ ID NO 55
<211> LENGTH: 16
<212> TYPE: PRT
<213> ORGANISM: Artificial Sequence
<220> FEATURE:
<223> OTHER INFORMATION: 46J3A HC CDR3

<400> SEQUENCE: 55

Ala Arg Tyr Trp Asp Tyr Tyr Gly Ser Thr Tyr Gly Tyr Phe Asp Val
1               5                   10                  15

<210> SEQ ID NO 56
<211> LENGTH: 8
<212> TYPE: PRT
<213> ORGANISM: Artificial Sequence
<220> FEATURE:
<223> OTHER INFORMATION: 46O19A HC CDR1

<400> SEQUENCE: 56

Gly Tyr Thr Phe Thr Asp Tyr Asn
1               5
```

<210> SEQ ID NO 57
<211> LENGTH: 8
<212> TYPE: PRT
<213> ORGANISM: Artificial Sequence
<220> FEATURE:
<223> OTHER INFORMATION: 46O19A HC CDR2

<400> SEQUENCE: 57

Ile Asn Pro Asn Asn Gly Gly Thr
1               5

<210> SEQ ID NO 58
<211> LENGTH: 10
<212> TYPE: PRT
<213> ORGANISM: Artificial Sequence
<220> FEATURE:
<223> OTHER INFORMATION: 46O19A HC CDR3

<400> SEQUENCE: 58

Ala Arg Asp Tyr Phe Trp Tyr Phe Asp Val
1               5                   10

<210> SEQ ID NO 59
<211> LENGTH: 8
<212> TYPE: PRT
<213> ORGANISM: Artificial Sequence
<220> FEATURE:
<223> OTHER INFORMATION: 47H24A HC CDR1

<400> SEQUENCE: 59

Gly Phe Ser Leu Thr Ser Tyr Gly
1               5

<210> SEQ ID NO 60
<211> LENGTH: 7
<212> TYPE: PRT
<213> ORGANISM: Artificial Sequence
<220> FEATURE:
<223> OTHER INFORMATION: 47H24A HC CDR2

<400> SEQUENCE: 60

Ile Trp Ser Gly Gly Ser Thr
1               5

<210> SEQ ID NO 61
<211> LENGTH: 7
<212> TYPE: PRT
<213> ORGANISM: Artificial Sequence
<220> FEATURE:
<223> OTHER INFORMATION: 47H24A HC CDR3

<400> SEQUENCE: 61

Ala Ser Gln Tyr Val Ala Tyr
1               5

<210> SEQ ID NO 62
<211> LENGTH: 8
<212> TYPE: PRT
<213> ORGANISM: Artificial Sequence
<220> FEATURE:
<223> OTHER INFORMATION: 49O5A HC CDR1

<400> SEQUENCE: 62

Gly Tyr Thr Phe Thr Ser Tyr Trp
1               5

```
<210> SEQ ID NO 63
<211> LENGTH: 8
<212> TYPE: PRT
<213> ORGANISM: Artificial Sequence
<220> FEATURE:
<223> OTHER INFORMATION: 49O5A HC CDR2

<400> SEQUENCE: 63

Ile Asn Pro Ser Asn Gly Gly Thr
1               5

<210> SEQ ID NO 64
<211> LENGTH: 14
<212> TYPE: PRT
<213> ORGANISM: Artificial Sequence
<220> FEATURE:
<223> OTHER INFORMATION: 49O5A HC CDR3

<400> SEQUENCE: 64

Ala Arg Ser Lys Ser Asn Tyr Gly Tyr Tyr Ala Met Asp Tyr
1               5                   10

<210> SEQ ID NO 65
<211> LENGTH: 8
<212> TYPE: PRT
<213> ORGANISM: Artificial Sequence
<220> FEATURE:
<223> OTHER INFORMATION: 50B10A HC CDR1

<400> SEQUENCE: 65

Gly Tyr Thr Phe Thr Ser Tyr Trp
1               5

<210> SEQ ID NO 66
<211> LENGTH: 8
<212> TYPE: PRT
<213> ORGANISM: Artificial Sequence
<220> FEATURE:
<223> OTHER INFORMATION: 50B10A HC CDR2

<400> SEQUENCE: 66

Ile Asn Pro Ser Asn Gly Arg Thr
1               5

<210> SEQ ID NO 67
<211> LENGTH: 17
<212> TYPE: PRT
<213> ORGANISM: Artificial Sequence
<220> FEATURE:
<223> OTHER INFORMATION: 50B10A HC CDR3

<400> SEQUENCE: 67

Ala Arg Ser Glu Gly Arg Val Tyr Tyr Asp Tyr Phe Tyr Ala Met Asp
1               5                   10                  15

Tyr

<210> SEQ ID NO 68
<211> LENGTH: 8
<212> TYPE: PRT
<213> ORGANISM: Artificial Sequence
<220> FEATURE:
<223> OTHER INFORMATION: 50H17A HC CDR1

<400> SEQUENCE: 68

Gly Tyr Ala Phe Thr Asn Tyr Leu
1               5
```

<210> SEQ ID NO 69
<211> LENGTH: 8
<212> TYPE: PRT
<213> ORGANISM: Artificial Sequence
<220> FEATURE:
<223> OTHER INFORMATION: 50H17A HC CDR2

<400> SEQUENCE: 69

Ile Asn Pro Gly Ser Gly Gly Thr
1               5

<210> SEQ ID NO 70
<211> LENGTH: 10
<212> TYPE: PRT
<213> ORGANISM: Artificial Sequence
<220> FEATURE:
<223> OTHER INFORMATION: 50H17A HC CDR3

<400> SEQUENCE: 70

Ala Arg Asp Tyr Tyr Trp Tyr Phe Asp Val
1               5                   10

<210> SEQ ID NO 71
<211> LENGTH: 8
<212> TYPE: PRT
<213> ORGANISM: Artificial Sequence
<220> FEATURE:
<223> OTHER INFORMATION: 50E16A HC CDR1

<400> SEQUENCE: 71

Ala Ile Arg Asp Thr Asn Tyr Trp
1               5

<210> SEQ ID NO 72
<211> LENGTH: 8
<212> TYPE: PRT
<213> ORGANISM: Artificial Sequence
<220> FEATURE:
<223> OTHER INFORMATION: 50E16A HC CDR2

<400> SEQUENCE: 72

Ile Tyr Pro Gly Asn Gly Asp Thr
1               5

<210> SEQ ID NO 73
<211> LENGTH: 13
<212> TYPE: PRT
<213> ORGANISM: Artificial Sequence
<220> FEATURE:
<223> OTHER INFORMATION: 50E16A HC CDR3

<400> SEQUENCE: 73

Ala Thr Tyr Tyr Ser Asn Tyr Gly Gly Ala Met Asp Tyr
1               5                   10

<210> SEQ ID NO 74
<211> LENGTH: 8
<212> TYPE: PRT
<213> ORGANISM: Artificial Sequence
<220> FEATURE:
<223> OTHER INFORMATION: 50F1A HC CDR1

<400> SEQUENCE: 74

Gly Tyr Thr Phe Thr Asp Tyr Ser
1               5

```
<210> SEQ ID NO 75
<211> LENGTH: 8
<212> TYPE: PRT
<213> ORGANISM: Artificial Sequence
<220> FEATURE:
<223> OTHER INFORMATION: 50F1A HC CDR2

<400> SEQUENCE: 75

Ile Asn Thr Glu Thr Gly Glu Pro
1               5

<210> SEQ ID NO 76
<211> LENGTH: 10
<212> TYPE: PRT
<213> ORGANISM: Artificial Sequence
<220> FEATURE:
<223> OTHER INFORMATION: 50F1A HC CDR3

<400> SEQUENCE: 76

Ala Arg Asp Ile Phe Trp Ala Met Asp Tyr
1               5                   10

<210> SEQ ID NO 77
<211> LENGTH: 8
<212> TYPE: PRT
<213> ORGANISM: Artificial Sequence
<220> FEATURE:
<223> OTHER INFORMATION: 54I14A HC CDR1

<400> SEQUENCE: 77

Gly Tyr Thr Phe Thr Ser Tyr Asn
1               5

<210> SEQ ID NO 78
<211> LENGTH: 8
<212> TYPE: PRT
<213> ORGANISM: Artificial Sequence
<220> FEATURE:
<223> OTHER INFORMATION: 54I14A HC CDR2

<400> SEQUENCE: 78

Ile Tyr Pro Gly Asn Gly Asp Thr
1               5

<210> SEQ ID NO 79
<211> LENGTH: 10
<212> TYPE: PRT
<213> ORGANISM: Artificial Sequence
<220> FEATURE:
<223> OTHER INFORMATION: 54I14A HC CDR3

<400> SEQUENCE: 79

Ala Arg Tyr Asp Tyr Asp Ala Met Asp Tyr
1               5                   10

<210> SEQ ID NO 80
<211> LENGTH: 8
<212> TYPE: PRT
<213> ORGANISM: Artificial Sequence
<220> FEATURE:
<223> OTHER INFORMATION: 52K11A HC CDR1

<400> SEQUENCE: 80

Gly Tyr Ser Phe Thr Gly Tyr Asn
1               5

<210> SEQ ID NO 81
```

```
<211> LENGTH: 8
<212> TYPE: PRT
<213> ORGANISM: Artificial Sequence
<220> FEATURE:
<223> OTHER INFORMATION: 52K11A HC CDR2

<400> SEQUENCE: 81

Ile Asn Pro Tyr Tyr Gly Ser Thr
1               5

<210> SEQ ID NO 82
<211> LENGTH: 12
<212> TYPE: PRT
<213> ORGANISM: Artificial Sequence
<220> FEATURE:
<223> OTHER INFORMATION: 52K11A HC CDR3

<400> SEQUENCE: 82

Ala Gly Ser Ser Tyr Val Asp Tyr Ala Met Asp Tyr
1               5                   10

<210> SEQ ID NO 83
<211> LENGTH: 8
<212> TYPE: PRT
<213> ORGANISM: Artificial Sequence
<220> FEATURE:
<223> OTHER INFORMATION: 53H21A HC CDR1

<400> SEQUENCE: 83

Gly Tyr Thr Phe Thr Ser Tyr Val
1               5

<210> SEQ ID NO 84
<211> LENGTH: 8
<212> TYPE: PRT
<213> ORGANISM: Artificial Sequence
<220> FEATURE:
<223> OTHER INFORMATION: 53H21A HC CDR2

<400> SEQUENCE: 84

Ile Ile Pro Tyr Asn Asp Gly Thr
1               5

<210> SEQ ID NO 85
<211> LENGTH: 11
<212> TYPE: PRT
<213> ORGANISM: Artificial Sequence
<220> FEATURE:
<223> OTHER INFORMATION: 53H21A HC CDR3

<400> SEQUENCE: 85

Ala Arg Trp Gly Asn Trp Asp Tyr Phe Asp Tyr
1               5                   10

<210> SEQ ID NO 86
<211> LENGTH: 8
<212> TYPE: PRT
<213> ORGANISM: Artificial Sequence
<220> FEATURE:
<223> OTHER INFORMATION: 53I12A HC CDR1

<400> SEQUENCE: 86

Gly Tyr Thr Phe Thr Ser Tyr Trp
1               5

<210> SEQ ID NO 87
<211> LENGTH: 8
```

```
<212> TYPE: PRT
<213> ORGANISM: Artificial Sequence
<220> FEATURE:
<223> OTHER INFORMATION: 53I12A HC CDR2

<400> SEQUENCE: 87

Ile Tyr Ala Gly Ser Ser Ser
1               5

<210> SEQ ID NO 88
<211> LENGTH: 12
<212> TYPE: PRT
<213> ORGANISM: Artificial Sequence
<220> FEATURE:
<223> OTHER INFORMATION: 53I12A HC CDR3

<400> SEQUENCE: 88

Ala Arg Ser Gly His Gly Tyr Asp Gly Phe Ala Tyr
1               5                   10

<210> SEQ ID NO 89
<211> LENGTH: 8
<212> TYPE: PRT
<213> ORGANISM: Artificial Sequence
<220> FEATURE:
<223> OTHER INFORMATION: 60A9A HC CDR1

<400> SEQUENCE: 89

Gly Tyr Ala Phe Ser Ser Tyr Trp
1               5

<210> SEQ ID NO 90
<211> LENGTH: 8
<212> TYPE: PRT
<213> ORGANISM: Artificial Sequence
<220> FEATURE:
<223> OTHER INFORMATION: 60A9A HC CDR2

<400> SEQUENCE: 90

Ile Tyr Pro Gly Asp Gly Asp Thr
1               5

<210> SEQ ID NO 91
<211> LENGTH: 14
<212> TYPE: PRT
<213> ORGANISM: Artificial Sequence
<220> FEATURE:
<223> OTHER INFORMATION: 60A9A HC CDR3

<400> SEQUENCE: 91

Ala Arg Glu Ala Ile Tyr Tyr Gly Asn Tyr Val Phe Thr Tyr
1               5                   10

<210> SEQ ID NO 92
<211> LENGTH: 8
<212> TYPE: PRT
<213> ORGANISM: Artificial Sequence
<220> FEATURE:
<223> OTHER INFORMATION: 39J9A HC CDR1

<400> SEQUENCE: 92

Gly Tyr Ala Phe Thr Asn Tyr Leu
1               5

<210> SEQ ID NO 93
<211> LENGTH: 8
<212> TYPE: PRT
```

```
<213> ORGANISM: Artificial Sequence
<220> FEATURE:
<223> OTHER INFORMATION: 39J9A HC CDR2

<400> SEQUENCE: 93

Ile Asn Pro Gly Ser Gly Gly Thr
1               5

<210> SEQ ID NO 94
<211> LENGTH: 13
<212> TYPE: PRT
<213> ORGANISM: Artificial Sequence
<220> FEATURE:
<223> OTHER INFORMATION: 39J9A HC CDR3

<400> SEQUENCE: 94

Ala Arg Arg Gly Asp Tyr Tyr Gly Asn Pro Phe Asp Tyr
1               5                   10

<210> SEQ ID NO 95
<211> LENGTH: 8
<212> TYPE: PRT
<213> ORGANISM: Artificial Sequence
<220> FEATURE:
<223> OTHER INFORMATION: 49H8A HC CDR1

<400> SEQUENCE: 95

Gly Tyr Thr Phe Thr Asn Tyr Trp
1               5

<210> SEQ ID NO 96
<211> LENGTH: 8
<212> TYPE: PRT
<213> ORGANISM: Artificial Sequence
<220> FEATURE:
<223> OTHER INFORMATION: 49H8A HC CDR2

<400> SEQUENCE: 96

Ile Asp Pro Ser Asp Asn Tyr Thr
1               5

<210> SEQ ID NO 97
<211> LENGTH: 14
<212> TYPE: PRT
<213> ORGANISM: Artificial Sequence
<220> FEATURE:
<223> OTHER INFORMATION: 49H8A HC CDR3

<400> SEQUENCE: 97

Ala Arg Gly Tyr Tyr Gly Tyr Ser Pro Ser Trp Phe Ala Tyr
1               5                   10

<210> SEQ ID NO 98
<211> LENGTH: 8
<212> TYPE: PRT
<213> ORGANISM: Artificial Sequence
<220> FEATURE:
<223> OTHER INFORMATION: 51B10A HC CDR1

<400> SEQUENCE: 98

Gly Tyr Ser Phe Thr Gly Tyr Tyr
1               5

<210> SEQ ID NO 99
<211> LENGTH: 8
<212> TYPE: PRT
<213> ORGANISM: Artificial Sequence
```

<220> FEATURE:
<223> OTHER INFORMATION: 51B10A HC CDR2

<400> SEQUENCE: 99

Ile Asn Pro Tyr Ser Gly Ala Thr
1               5

<210> SEQ ID NO 100
<211> LENGTH: 10
<212> TYPE: PRT
<213> ORGANISM: Artificial Sequence
<220> FEATURE:
<223> OTHER INFORMATION: 51B10A HC CDR3

<400> SEQUENCE: 100

Ala Arg Ser Tyr Tyr Gly Ala Met Asp Tyr
1               5                   10

<210> SEQ ID NO 101
<211> LENGTH: 11
<212> TYPE: PRT
<213> ORGANISM: Artificial Sequence
<220> FEATURE:
<223> OTHER INFORMATION: 37C7A LC CDR1

<400> SEQUENCE: 101

Gln Asn Leu Val His Ser Tyr Gly Asn Thr Tyr
1               5                   10

<210> SEQ ID NO 102
<211> LENGTH: 3
<212> TYPE: PRT
<213> ORGANISM: Artificial Sequence
<220> FEATURE:
<223> OTHER INFORMATION: 37C7A LC CDR2

<400> SEQUENCE: 102

Lys Val Ser
1

<210> SEQ ID NO 103
<211> LENGTH: 9
<212> TYPE: PRT
<213> ORGANISM: Artificial Sequence
<220> FEATURE:
<223> OTHER INFORMATION: 37C7A LC CDR3

<400> SEQUENCE: 103

Ser Gln Asn Thr His Val Pro Trp Thr
1               5

<210> SEQ ID NO 104
<211> LENGTH: 11
<212> TYPE: PRT
<213> ORGANISM: Artificial Sequence
<220> FEATURE:
<223> OTHER INFORMATION: 38C16A LC CDR1

<400> SEQUENCE: 104

Gln Ser Leu Leu Asp Ser Asp Gly Arg Thr Tyr
1               5                   10

<210> SEQ ID NO 105
<211> LENGTH: 3
<212> TYPE: PRT
<213> ORGANISM: Artificial Sequence
<220> FEATURE:

<223> OTHER INFORMATION: 38C16A LC CDR2

<400> SEQUENCE: 105

Leu Val Ser
1

<210> SEQ ID NO 106
<211> LENGTH: 9
<212> TYPE: PRT
<213> ORGANISM: Artificial Sequence
<220> FEATURE:
<223> OTHER INFORMATION: 38C16A LC CDR3

<400> SEQUENCE: 106

Trp Gln Gly Thr His Phe Pro His Thr
1               5

<210> SEQ ID NO 107
<211> LENGTH: 12
<212> TYPE: PRT
<213> ORGANISM: Artificial Sequence
<220> FEATURE:
<223> OTHER INFORMATION: 39G8A LC CDR1

<400> SEQUENCE: 107

Gln Ser Leu Leu Asn Ser Ser Asn Gln Lys Asn Tyr
1               5                   10

<210> SEQ ID NO 108
<211> LENGTH: 3
<212> TYPE: PRT
<213> ORGANISM: Artificial Sequence
<220> FEATURE:
<223> OTHER INFORMATION: 39G8A LC CDR2

<400> SEQUENCE: 108

Phe Ala Ser
1

<210> SEQ ID NO 109
<211> LENGTH: 9
<212> TYPE: PRT
<213> ORGANISM: Artificial Sequence
<220> FEATURE:
<223> OTHER INFORMATION: 39G8A LC CDR3

<400> SEQUENCE: 109

Gln Gln His Tyr Ser Thr Pro Tyr Thr
1               5

<210> SEQ ID NO 110
<211> LENGTH: 10
<212> TYPE: PRT
<213> ORGANISM: Artificial Sequence
<220> FEATURE:
<223> OTHER INFORMATION: 43E8A LC CDR1

<400> SEQUENCE: 110

Glu Ser Val Asp Asn Tyr Gly Ile Ser Phe
1               5                   10

<210> SEQ ID NO 111
<211> LENGTH: 3
<212> TYPE: PRT
<213> ORGANISM: Artificial Sequence
<220> FEATURE:
<223> OTHER INFORMATION: 43E8A LC CDR2

```
<400> SEQUENCE: 111

Ala Ala Ser
1

<210> SEQ ID NO 112
<211> LENGTH: 9
<212> TYPE: PRT
<213> ORGANISM: Artificial Sequence
<220> FEATURE:
<223> OTHER INFORMATION: 43E8A LC CDR3

<400> SEQUENCE: 112

Gln Gln Ser Lys Glu Val Pro Phe Thr
1               5

<210> SEQ ID NO 113
<211> LENGTH: 6
<212> TYPE: PRT
<213> ORGANISM: Artificial Sequence
<220> FEATURE:
<223> OTHER INFORMATION: 46J3A LC CDR1

<400> SEQUENCE: 113

Lys Asn Ile Ser Lys Tyr
1               5

<210> SEQ ID NO 114
<211> LENGTH: 3
<212> TYPE: PRT
<213> ORGANISM: Artificial Sequence
<220> FEATURE:
<223> OTHER INFORMATION: 46J3A LC CDR2

<400> SEQUENCE: 114

Ser Gly Ser
1

<210> SEQ ID NO 115
<211> LENGTH: 9
<212> TYPE: PRT
<213> ORGANISM: Artificial Sequence
<220> FEATURE:
<223> OTHER INFORMATION: 46J3A LC CDR3

<400> SEQUENCE: 115

Gln Gln His Asn Glu Tyr Pro Phe Thr
1               5

<210> SEQ ID NO 116
<211> LENGTH: 12
<212> TYPE: PRT
<213> ORGANISM: Artificial Sequence
<220> FEATURE:
<223> OTHER INFORMATION: 46O19A LC CDR1

<400> SEQUENCE: 116

Gln Ser Leu Leu Asn Ser Gly Asn Gln Lys Asn Tyr
1               5                   10

<210> SEQ ID NO 117
<211> LENGTH: 3
<212> TYPE: PRT
<213> ORGANISM: Artificial Sequence
<220> FEATURE:
<223> OTHER INFORMATION: 46O19A LC CDR2
```

```
<400> SEQUENCE: 117

Trp Ala Ser
1

<210> SEQ ID NO 118
<211> LENGTH: 9
<212> TYPE: PRT
<213> ORGANISM: Artificial Sequence
<220> FEATURE:
<223> OTHER INFORMATION: 46O19A LC CDR3

<400> SEQUENCE: 118

Gln Asn Asp Tyr Ser Tyr Pro Leu Thr
1               5

<210> SEQ ID NO 119
<211> LENGTH: 6
<212> TYPE: PRT
<213> ORGANISM: Artificial Sequence
<220> FEATURE:
<223> OTHER INFORMATION: 47H24A LC CDR1

<400> SEQUENCE: 119

Gln Asp Ile Gly Ser Arg
1               5

<210> SEQ ID NO 120
<211> LENGTH: 3
<212> TYPE: PRT
<213> ORGANISM: Artificial Sequence
<220> FEATURE:
<223> OTHER INFORMATION: 47H24A LC CDR2

<400> SEQUENCE: 120

Ala Thr Ser
1

<210> SEQ ID NO 121
<211> LENGTH: 9
<212> TYPE: PRT
<213> ORGANISM: Artificial Sequence
<220> FEATURE:
<223> OTHER INFORMATION: 47H24A LC CDR3

<400> SEQUENCE: 121

Leu Gln Tyr Ala Ser Ser Pro Phe Thr
1               5

<210> SEQ ID NO 122
<211> LENGTH: 6
<212> TYPE: PRT
<213> ORGANISM: Artificial Sequence
<220> FEATURE:
<223> OTHER INFORMATION: 49O5A LC CDR1

<400> SEQUENCE: 122

Asp His Ile Asp Asn Trp
1               5

<210> SEQ ID NO 123
<211> LENGTH: 3
<212> TYPE: PRT
<213> ORGANISM: Artificial Sequence
<220> FEATURE:
<223> OTHER INFORMATION: 49O5A LC CDR2

<400> SEQUENCE: 123
```

```
Gly Ala Thr
1

<210> SEQ ID NO 124
<211> LENGTH: 9
<212> TYPE: PRT
<213> ORGANISM: Artificial Sequence
<220> FEATURE:
<223> OTHER INFORMATION: 49O5A LC CDR3

<400> SEQUENCE: 124

Gln Gln Tyr Trp Ser Ser Pro Phe Thr
1               5

<210> SEQ ID NO 125
<211> LENGTH: 6
<212> TYPE: PRT
<213> ORGANISM: Artificial Sequence
<220> FEATURE:
<223> OTHER INFORMATION: 50B10A LC CDR1

<400> SEQUENCE: 125

Gln Asp Ile Ser Asn Tyr
1               5

<210> SEQ ID NO 126
<211> LENGTH: 3
<212> TYPE: PRT
<213> ORGANISM: Artificial Sequence
<220> FEATURE:
<223> OTHER INFORMATION: 50B10A LC CDR2

<400> SEQUENCE: 126

Tyr Thr Ser
1

<210> SEQ ID NO 127
<211> LENGTH: 9
<212> TYPE: PRT
<213> ORGANISM: Artificial Sequence
<220> FEATURE:
<223> OTHER INFORMATION: 50B10A LC CDR3

<400> SEQUENCE: 127

Gln Gln Gly Asn Thr Leu Pro Trp Thr
1               5

<210> SEQ ID NO 128
<211> LENGTH: 12
<212> TYPE: PRT
<213> ORGANISM: Artificial Sequence
<220> FEATURE:
<223> OTHER INFORMATION: 50H17A LC CDR1

<400> SEQUENCE: 128

Gln Ser Leu Leu Asn Ser Gly Asn Gln Lys Asn Tyr
1               5                   10

<210> SEQ ID NO 129
<211> LENGTH: 3
<212> TYPE: PRT
<213> ORGANISM: Artificial Sequence
<220> FEATURE:
<223> OTHER INFORMATION: 50H17A LC CDR2

<400> SEQUENCE: 129
```

Trp Ala Ser
1

<210> SEQ ID NO 130
<211> LENGTH: 9
<212> TYPE: PRT
<213> ORGANISM: Artificial Sequence
<220> FEATURE:
<223> OTHER INFORMATION: 50H17A LC CDR3

<400> SEQUENCE: 130

Gln Asn Asp Tyr Ser Tyr Pro Leu Thr
1               5

<210> SEQ ID NO 131
<211> LENGTH: 8
<212> TYPE: PRT
<213> ORGANISM: Artificial Sequence
<220> FEATURE:
<223> OTHER INFORMATION: 50E16A LC CDR1

<400> SEQUENCE: 131

Gln Asp Val Gly Thr Ala Val Ala
1               5

<210> SEQ ID NO 132
<211> LENGTH: 3
<212> TYPE: PRT
<213> ORGANISM: Artificial Sequence
<220> FEATURE:
<223> OTHER INFORMATION: 50E16A LC CDR2

<400> SEQUENCE: 132

Trp Ala Ser
1

<210> SEQ ID NO 133
<211> LENGTH: 9
<212> TYPE: PRT
<213> ORGANISM: Artificial Sequence
<220> FEATURE:
<223> OTHER INFORMATION: 50E16A LC CDR3

<400> SEQUENCE: 133

Gln Gln Tyr Ser Ser Tyr Pro Tyr Thr
1               5

<210> SEQ ID NO 134
<211> LENGTH: 12
<212> TYPE: PRT
<213> ORGANISM: Artificial Sequence
<220> FEATURE:
<223> OTHER INFORMATION: 50F1A LC CDR1

<400> SEQUENCE: 134

Gln Ser Leu Leu Asn Ser Gly Asn Gln Lys Asn Tyr
1               5                   10

<210> SEQ ID NO 135
<211> LENGTH: 3
<212> TYPE: PRT
<213> ORGANISM: Artificial Sequence
<220> FEATURE:
<223> OTHER INFORMATION: 50F1A LC CDR2

<400> SEQUENCE: 135

Trp Ala Ser

```
<210> SEQ ID NO 136
<211> LENGTH: 9
<212> TYPE: PRT
<213> ORGANISM: Artificial Sequence
<220> FEATURE:
<223> OTHER INFORMATION: 50F1A LC CDR3

<400> SEQUENCE: 136

Gln Asn Asp Tyr Ser Tyr Pro Leu Thr
1               5

<210> SEQ ID NO 137
<211> LENGTH: 6
<212> TYPE: PRT
<213> ORGANISM: Artificial Sequence
<220> FEATURE:
<223> OTHER INFORMATION: 54I14A LC CDR1

<400> SEQUENCE: 137

Glu Asn Ile Tyr Ser Tyr
1               5

<210> SEQ ID NO 138
<211> LENGTH: 3
<212> TYPE: PRT
<213> ORGANISM: Artificial Sequence
<220> FEATURE:
<223> OTHER INFORMATION: 54I14A LC CDR2

<400> SEQUENCE: 138

Asn Ala Lys
1

<210> SEQ ID NO 139
<211> LENGTH: 9
<212> TYPE: PRT
<213> ORGANISM: Artificial Sequence
<220> FEATURE:
<223> OTHER INFORMATION: 54I14A LC CDR3

<400> SEQUENCE: 139

Gln His His Tyr Gly Thr Pro Phe Thr
1               5

<210> SEQ ID NO 140
<211> LENGTH: 11
<212> TYPE: PRT
<213> ORGANISM: Artificial Sequence
<220> FEATURE:
<223> OTHER INFORMATION: 52K11A LC CDR1

<400> SEQUENCE: 140

Lys Ser Leu Leu His Ser Asn Asp Ile Thr Tyr
1               5                   10

<210> SEQ ID NO 141
<211> LENGTH: 3
<212> TYPE: PRT
<213> ORGANISM: Artificial Sequence
<220> FEATURE:
<223> OTHER INFORMATION: 52K11A LC CDR2

<400> SEQUENCE: 141

Arg Met Ser
1
```

<210> SEQ ID NO 142
<211> LENGTH: 9
<212> TYPE: PRT
<213> ORGANISM: Artificial Sequence
<220> FEATURE:
<223> OTHER INFORMATION: 52K11A LC CDR3

<400> SEQUENCE: 142

Ala Gln Met Leu Glu Arg Pro Trp Thr
1               5

<210> SEQ ID NO 143
<211> LENGTH: 5
<212> TYPE: PRT
<213> ORGANISM: Artificial Sequence
<220> FEATURE:
<223> OTHER INFORMATION: 53H21A LC CDR1

<400> SEQUENCE: 143

Ser Ser Val Ser Tyr
1               5

<210> SEQ ID NO 144
<211> LENGTH: 3
<212> TYPE: PRT
<213> ORGANISM: Artificial Sequence
<220> FEATURE:
<223> OTHER INFORMATION: 53H21A LC CDR2

<400> SEQUENCE: 144

Leu Thr Ser
1

<210> SEQ ID NO 145
<211> LENGTH: 9
<212> TYPE: PRT
<213> ORGANISM: Artificial Sequence
<220> FEATURE:
<223> OTHER INFORMATION: 53H21A LC CDR3

<400> SEQUENCE: 145

Gln Gln Trp Ser Ser Asn Pro Trp Thr
1               5

<210> SEQ ID NO 146
<211> LENGTH: 6
<212> TYPE: PRT
<213> ORGANISM: Artificial Sequence
<220> FEATURE:
<223> OTHER INFORMATION: 53I12A LC CDR1

<400> SEQUENCE: 146

Gln Gly Ile Ser Asn Tyr
1               5

<210> SEQ ID NO 147
<211> LENGTH: 3
<212> TYPE: PRT
<213> ORGANISM: Artificial Sequence
<220> FEATURE:
<223> OTHER INFORMATION: 53I12A LC CDR2

<400> SEQUENCE: 147

Tyr Thr Ser
1

<210> SEQ ID NO 148
<211> LENGTH: 9
<212> TYPE: PRT
<213> ORGANISM: Artificial Sequence
<220> FEATURE:
<223> OTHER INFORMATION: 53I12A LC CDR3

<400> SEQUENCE: 148

Gln Gln Tyr Ser Lys Leu Pro Arg Thr
1               5

<210> SEQ ID NO 149
<211> LENGTH: 12
<212> TYPE: PRT
<213> ORGANISM: Artificial Sequence
<220> FEATURE:
<223> OTHER INFORMATION: 60A9A LC CDR1

<400> SEQUENCE: 149

Gln Ser Leu Leu Asn Ser Ser Asn Gln Lys Asn Tyr
1               5                   10

<210> SEQ ID NO 150
<211> LENGTH: 3
<212> TYPE: PRT
<213> ORGANISM: Artificial Sequence
<220> FEATURE:
<223> OTHER INFORMATION: 60A9A LC CDR2

<400> SEQUENCE: 150

Phe Ala Ser
1

<210> SEQ ID NO 151
<211> LENGTH: 9
<212> TYPE: PRT
<213> ORGANISM: Artificial Sequence
<220> FEATURE:
<223> OTHER INFORMATION: 60A9A LC CDR3

<400> SEQUENCE: 151

Gln Gln His Tyr Ser Thr Pro Leu Thr
1               5

<210> SEQ ID NO 152
<211> LENGTH: 6
<212> TYPE: PRT
<213> ORGANISM: Artificial Sequence
<220> FEATURE:
<223> OTHER INFORMATION: 39J9A LC CDR1

<400> SEQUENCE: 152

Glu Asn Ile Tyr Tyr Ser
1               5

<210> SEQ ID NO 153
<211> LENGTH: 3
<212> TYPE: PRT
<213> ORGANISM: Artificial Sequence
<220> FEATURE:
<223> OTHER INFORMATION: 39J9A LC CDR2

<400> SEQUENCE: 153

Asn Ala Asp
1

```
<210> SEQ ID NO 154
<211> LENGTH: 9
<212> TYPE: PRT
<213> ORGANISM: Artificial Sequence
<220> FEATURE:
<223> OTHER INFORMATION: 39J9A LC CDR3

<400> SEQUENCE: 154

Lys Gln Ala Tyr Asp Val Pro Leu Thr
1               5

<210> SEQ ID NO 155
<211> LENGTH: 5
<212> TYPE: PRT
<213> ORGANISM: Artificial Sequence
<220> FEATURE:
<223> OTHER INFORMATION: 49H8A LC CDR1

<400> SEQUENCE: 155

Ser Ser Val Ser Tyr
1               5

<210> SEQ ID NO 156
<211> LENGTH: 3
<212> TYPE: PRT
<213> ORGANISM: Artificial Sequence
<220> FEATURE:
<223> OTHER INFORMATION: 49H8A LC CDR2

<400> SEQUENCE: 156

Leu Thr Ser
1

<210> SEQ ID NO 157
<211> LENGTH: 9
<212> TYPE: PRT
<213> ORGANISM: Artificial Sequence
<220> FEATURE:
<223> OTHER INFORMATION: 49H8A LC CDR3

<400> SEQUENCE: 157

Gln Gln Trp Ser Ser Asn Pro Pro Thr
1               5

<210> SEQ ID NO 158
<211> LENGTH: 6
<212> TYPE: PRT
<213> ORGANISM: Artificial Sequence
<220> FEATURE:
<223> OTHER INFORMATION: 51B10A LC CDR1

<400> SEQUENCE: 158

Gln Asp Ile Asn Ser Tyr
1               5

<210> SEQ ID NO 159
<211> LENGTH: 3
<212> TYPE: PRT
<213> ORGANISM: Artificial Sequence
<220> FEATURE:
<223> OTHER INFORMATION: 51B10A LC CDR2

<400> SEQUENCE: 159

Arg Ala Asn
1

<210> SEQ ID NO 160
```

```
<211> LENGTH: 9
<212> TYPE: PRT
<213> ORGANISM: Artificial Sequence
<220> FEATURE:
<223> OTHER INFORMATION: 51B10A LC CDR3

<400> SEQUENCE: 160

Leu Gln Tyr Asp Glu Phe Pro Leu Thr
1               5

<210> SEQ ID NO 161
<211> LENGTH: 12
<212> TYPE: PRT
<213> ORGANISM: Artificial Sequence
<220> FEATURE:
<223> OTHER INFORMATION: 37C7A HC CDR1

<400> SEQUENCE: 161

Gly Phe Ser Leu Ser Thr Phe Gly Met Gly Val Thr
1               5                   10

<210> SEQ ID NO 162
<211> LENGTH: 16
<212> TYPE: PRT
<213> ORGANISM: Artificial Sequence
<220> FEATURE:
<223> OTHER INFORMATION: 37C7A HC CDR2

<400> SEQUENCE: 162

His Ile Trp Trp Asp Asp Asp Met Tyr Tyr Asn Pro Ala Leu Lys Ser
1               5                   10                  15

<210> SEQ ID NO 163
<211> LENGTH: 12
<212> TYPE: PRT
<213> ORGANISM: Artificial Sequence
<220> FEATURE:
<223> OTHER INFORMATION: 37C7A HC CDR3

<400> SEQUENCE: 163

Ala Arg Ser Pro Ile Thr Thr Val Val Ala Asp Tyr
1               5                   10

<210> SEQ ID NO 164
<211> LENGTH: 10
<212> TYPE: PRT
<213> ORGANISM: Artificial Sequence
<220> FEATURE:
<223> OTHER INFORMATION: 38C16A HC CDR1

<400> SEQUENCE: 164

Gly Tyr Thr Phe Ser Ser Tyr Trp Ile Glu
1               5                   10

<210> SEQ ID NO 165
<211> LENGTH: 17
<212> TYPE: PRT
<213> ORGANISM: Artificial Sequence
<220> FEATURE:
<223> OTHER INFORMATION: 38C16A HC CDR2

<400> SEQUENCE: 165

Glu Ile Leu Pro Gly Ser Gly Ser Thr Asn Tyr Asn Glu Lys Phe Lys
1               5                   10                  15

Gly
```

```
<210> SEQ ID NO 166
<211> LENGTH: 14
<212> TYPE: PRT
<213> ORGANISM: Artificial Sequence
<220> FEATURE:
<223> OTHER INFORMATION: 38C16A HC CDR3

<400> SEQUENCE: 166

Ala Arg Gly Asp Tyr Phe Gly Ser Ser Tyr Arg Gly Pro Tyr
1               5                   10

<210> SEQ ID NO 167
<211> LENGTH: 10
<212> TYPE: PRT
<213> ORGANISM: Artificial Sequence
<220> FEATURE:
<223> OTHER INFORMATION: 39G8A HC CDR1

<400> SEQUENCE: 167

Gly Tyr Thr Phe Thr Ser Tyr Trp Met His
1               5                   10

<210> SEQ ID NO 168
<211> LENGTH: 17
<212> TYPE: PRT
<213> ORGANISM: Artificial Sequence
<220> FEATURE:
<223> OTHER INFORMATION: 39G8A HC CDR2

<400> SEQUENCE: 168

Glu Ile Asp Pro Ser Gly Gly Tyr Thr Asn Tyr Asn Gln Lys Phe Lys
1               5                   10                  15
Gly

<210> SEQ ID NO 169
<211> LENGTH: 14
<212> TYPE: PRT
<213> ORGANISM: Artificial Sequence
<220> FEATURE:
<223> OTHER INFORMATION: 39G8A HC CDR3

<400> SEQUENCE: 169

Ala Arg Asn Tyr Tyr Tyr Gly Ser Ser Gly Thr Met Asp Tyr
1               5                   10

<210> SEQ ID NO 170
<211> LENGTH: 10
<212> TYPE: PRT
<213> ORGANISM: Artificial Sequence
<220> FEATURE:
<223> OTHER INFORMATION: 43E8A HC CDR1

<400> SEQUENCE: 170

Gly Tyr Thr Phe Ser Asn Tyr Trp Ile Glu
1               5                   10

<210> SEQ ID NO 171
<211> LENGTH: 17
<212> TYPE: PRT
<213> ORGANISM: Artificial Sequence
<220> FEATURE:
<223> OTHER INFORMATION: 43E8A HC CDR2

<400> SEQUENCE: 171

Glu Ile Leu Pro Gly Asn Val Ile Thr Asn Tyr Asn Glu Lys Phe Lys
1               5                   10                  15
```

Gly

<210> SEQ ID NO 172
<211> LENGTH: 14
<212> TYPE: PRT
<213> ORGANISM: Artificial Sequence
<220> FEATURE:
<223> OTHER INFORMATION: 43E8A HC CDR3

<400> SEQUENCE: 172

Ala Arg Arg Gly Asp Asp Gly Tyr Leu Tyr Ala Met Asp Tyr
1               5                   10

<210> SEQ ID NO 173
<211> LENGTH: 10
<212> TYPE: PRT
<213> ORGANISM: Artificial Sequence
<220> FEATURE:
<223> OTHER INFORMATION: 46J3A HC CDR1

<400> SEQUENCE: 173

Gly Tyr Thr Phe Thr Asp Tyr Tyr Met His
1               5                   10

<210> SEQ ID NO 174
<211> LENGTH: 17
<212> TYPE: PRT
<213> ORGANISM: Artificial Sequence
<220> FEATURE:
<223> OTHER INFORMATION: 46J3A HC CDR2

<400> SEQUENCE: 174

Glu Ile Tyr Pro Gly Ser Gly Asn Thr Tyr Tyr Asn Glu Lys Phe Lys
1               5                   10                  15

Gly

<210> SEQ ID NO 175
<211> LENGTH: 16
<212> TYPE: PRT
<213> ORGANISM: Artificial Sequence
<220> FEATURE:
<223> OTHER INFORMATION: 46J3A HC CDR3

<400> SEQUENCE: 175

Ala Arg Tyr Trp Asp Tyr Tyr Gly Ser Thr Gly Tyr Phe Asp Val
1               5                   10                  15

<210> SEQ ID NO 176
<211> LENGTH: 10
<212> TYPE: PRT
<213> ORGANISM: Artificial Sequence
<220> FEATURE:
<223> OTHER INFORMATION: 46O19A HC CDR1

<400> SEQUENCE: 176

Gly Tyr Thr Phe Thr Asp Tyr Asn Met His
1               5                   10

<210> SEQ ID NO 177
<211> LENGTH: 17
<212> TYPE: PRT
<213> ORGANISM: Artificial Sequence
<220> FEATURE:
<223> OTHER INFORMATION: 46O19A HC CDR2

<400> SEQUENCE: 177

```
Tyr Ile Asn Pro Asn Asn Gly Gly Thr Ser Tyr Asn Gln Lys Phe Lys
1               5                   10                  15
Gly

<210> SEQ ID NO 178
<211> LENGTH: 10
<212> TYPE: PRT
<213> ORGANISM: Artificial Sequence
<220> FEATURE:
<223> OTHER INFORMATION: 46O19A HC CDR3

<400> SEQUENCE: 178

Ala Arg Asp Tyr Phe Trp Tyr Phe Asp Val
1               5                   10

<210> SEQ ID NO 179
<211> LENGTH: 10
<212> TYPE: PRT
<213> ORGANISM: Artificial Sequence
<220> FEATURE:
<223> OTHER INFORMATION: 47H24A HC CDR1

<400> SEQUENCE: 179

Gly Phe Ser Leu Thr Ser Tyr Gly Val His
1               5                   10

<210> SEQ ID NO 180
<211> LENGTH: 17
<212> TYPE: PRT
<213> ORGANISM: Artificial Sequence
<220> FEATURE:
<223> OTHER INFORMATION: 47H24A HC CDR2

<400> SEQUENCE: 180

Val Ile Trp Ser Gly Gly Ser Thr Asp Tyr Asn Ala Ala Phe Ile Ser
1               5                   10                  15
Arg

<210> SEQ ID NO 181
<211> LENGTH: 7
<212> TYPE: PRT
<213> ORGANISM: Artificial Sequence
<220> FEATURE:
<223> OTHER INFORMATION: 47H24A HC CDR3

<400> SEQUENCE: 181

Ala Ser Gln Tyr Val Ala Tyr
1               5

<210> SEQ ID NO 182
<211> LENGTH: 10
<212> TYPE: PRT
<213> ORGANISM: Artificial Sequence
<220> FEATURE:
<223> OTHER INFORMATION: 49O5A HC CDR1

<400> SEQUENCE: 182

Gly Tyr Thr Phe Thr Ser Tyr Trp Met His
1               5                   10

<210> SEQ ID NO 183
<211> LENGTH: 17
<212> TYPE: PRT
<213> ORGANISM: Artificial Sequence
<220> FEATURE:
<223> OTHER INFORMATION: 49O5A HC CDR2
```

<400> SEQUENCE: 183

Asn Ile Asn Pro Ser Asn Gly Gly Thr Asn Tyr Asn Glu Lys Phe Lys
1               5                   10                  15
Ser

<210> SEQ ID NO 184
<211> LENGTH: 14
<212> TYPE: PRT
<213> ORGANISM: Artificial Sequence
<220> FEATURE:
<223> OTHER INFORMATION: 49O5A HC CDR3

<400> SEQUENCE: 184

Ala Arg Ser Lys Ser Asn Tyr Gly Tyr Tyr Ala Met Asp Tyr
1               5                   10

<210> SEQ ID NO 185
<211> LENGTH: 10
<212> TYPE: PRT
<213> ORGANISM: Artificial Sequence
<220> FEATURE:
<223> OTHER INFORMATION: 50B10A HC CDR1

<400> SEQUENCE: 185

Gly Tyr Thr Phe Thr Ser Tyr Trp Met His
1               5                   10

<210> SEQ ID NO 186
<211> LENGTH: 17
<212> TYPE: PRT
<213> ORGANISM: Artificial Sequence
<220> FEATURE:
<223> OTHER INFORMATION: 50B10A HC CDR2

<400> SEQUENCE: 186

Glu Ile Asn Pro Ser Asn Gly Arg Thr Asn Tyr Asn Glu Lys Phe Lys
1               5                   10                  15
Ser

<210> SEQ ID NO 187
<211> LENGTH: 17
<212> TYPE: PRT
<213> ORGANISM: Artificial Sequence
<220> FEATURE:
<223> OTHER INFORMATION: 50B10A HC CDR3

<400> SEQUENCE: 187

Ala Arg Ser Glu Gly Arg Val Tyr Tyr Asp Tyr Phe Tyr Ala Met Asp
1               5                   10                  15
Tyr

<210> SEQ ID NO 188
<211> LENGTH: 10
<212> TYPE: PRT
<213> ORGANISM: Artificial Sequence
<220> FEATURE:
<223> OTHER INFORMATION: 50H17A HC CDR1

<400> SEQUENCE: 188

Gly Tyr Ala Phe Thr Asn Tyr Leu Ile Glu
1               5                   10

<210> SEQ ID NO 189

```
<211> LENGTH: 17
<212> TYPE: PRT
<213> ORGANISM: Artificial Sequence
<220> FEATURE:
<223> OTHER INFORMATION: 50H17A HC CDR2

<400> SEQUENCE: 189

Val Ile Asn Pro Gly Ser Gly Gly Thr Asn Tyr Asn Glu Lys Phe Lys
1               5                   10                  15
Gly

<210> SEQ ID NO 190
<211> LENGTH: 10
<212> TYPE: PRT
<213> ORGANISM: Artificial Sequence
<220> FEATURE:
<223> OTHER INFORMATION: 50H17A HC CDR3

<400> SEQUENCE: 190

Ala Arg Asp Tyr Tyr Trp Tyr Phe Asp Val
1               5                   10

<210> SEQ ID NO 191
<211> LENGTH: 10
<212> TYPE: PRT
<213> ORGANISM: Artificial Sequence
<220> FEATURE:
<223> OTHER INFORMATION: 50E16A HC CDR1

<400> SEQUENCE: 191

Ala Ile Arg Asp Thr Asn Tyr Trp Met Gln
1               5                   10

<210> SEQ ID NO 192
<211> LENGTH: 17
<212> TYPE: PRT
<213> ORGANISM: Artificial Sequence
<220> FEATURE:
<223> OTHER INFORMATION: 50E16A HC CDR2

<400> SEQUENCE: 192

Ala Ile Tyr Pro Gly Asn Gly Asp Thr Ser Tyr Asn Gln Lys Phe Lys
1               5                   10                  15
Val

<210> SEQ ID NO 193
<211> LENGTH: 13
<212> TYPE: PRT
<213> ORGANISM: Artificial Sequence
<220> FEATURE:
<223> OTHER INFORMATION: 50E16A HC CDR3

<400> SEQUENCE: 193

Ala Thr Tyr Tyr Ser Asn Tyr Gly Gly Ala Met Asp Tyr
1               5                   10

<210> SEQ ID NO 194
<211> LENGTH: 10
<212> TYPE: PRT
<213> ORGANISM: Artificial Sequence
<220> FEATURE:
<223> OTHER INFORMATION: 50F1A HC CDR1

<400> SEQUENCE: 194

Gly Tyr Thr Phe Thr Asp Tyr Ser Met His
1               5                   10
```

<210> SEQ ID NO 195
<211> LENGTH: 17
<212> TYPE: PRT
<213> ORGANISM: Artificial Sequence
<220> FEATURE:
<223> OTHER INFORMATION: 50F1A HC CDR2

<400> SEQUENCE: 195

Trp Ile Asn Thr Glu Thr Gly Glu Pro Thr Tyr Ala Asp Asp Phe Lys
1               5                   10                  15

Gly

<210> SEQ ID NO 196
<211> LENGTH: 10
<212> TYPE: PRT
<213> ORGANISM: Artificial Sequence
<220> FEATURE:
<223> OTHER INFORMATION: 50F1A HC CDR3

<400> SEQUENCE: 196

Ala Arg Asp Ile Phe Trp Ala Met Asp Tyr
1               5                   10

<210> SEQ ID NO 197
<211> LENGTH: 10
<212> TYPE: PRT
<213> ORGANISM: Artificial Sequence
<220> FEATURE:
<223> OTHER INFORMATION: 54I14A HC CDR1

<400> SEQUENCE: 197

Gly Tyr Thr Phe Thr Ser Tyr Asn Met His
1               5                   10

<210> SEQ ID NO 198
<211> LENGTH: 17
<212> TYPE: PRT
<213> ORGANISM: Artificial Sequence
<220> FEATURE:
<223> OTHER INFORMATION: 54I14A HC CDR2

<400> SEQUENCE: 198

Ala Ile Tyr Pro Gly Asn Gly Asp Thr Ser Tyr Asn Gln Lys Phe Lys
1               5                   10                  15

Gly

<210> SEQ ID NO 199
<211> LENGTH: 10
<212> TYPE: PRT
<213> ORGANISM: Artificial Sequence
<220> FEATURE:
<223> OTHER INFORMATION: 54I14A HC CDR3

<400> SEQUENCE: 199

Ala Arg Tyr Asp Tyr Asp Ala Met Asp Tyr
1               5                   10

<210> SEQ ID NO 200
<211> LENGTH: 10
<212> TYPE: PRT
<213> ORGANISM: Artificial Sequence
<220> FEATURE:
<223> OTHER INFORMATION: 52K11A HC CDR1

<400> SEQUENCE: 200

```
Gly Tyr Ser Phe Thr Gly Tyr Asn Met Asn
1               5                   10

<210> SEQ ID NO 201
<211> LENGTH: 17
<212> TYPE: PRT
<213> ORGANISM: Artificial Sequence
<220> FEATURE:
<223> OTHER INFORMATION: 52K11A HC CDR2

<400> SEQUENCE: 201

Asn Ile Asn Pro Tyr Tyr Gly Ser Thr Ser Tyr Asn Gln Lys Phe Lys
1               5                   10                  15

Gly

<210> SEQ ID NO 202
<211> LENGTH: 12
<212> TYPE: PRT
<213> ORGANISM: Artificial Sequence
<220> FEATURE:
<223> OTHER INFORMATION: 52K11A HC CDR3

<400> SEQUENCE: 202

Ala Gly Ser Ser Tyr Val Asp Tyr Ala Met Asp Tyr
1               5                   10

<210> SEQ ID NO 203
<211> LENGTH: 10
<212> TYPE: PRT
<213> ORGANISM: Artificial Sequence
<220> FEATURE:
<223> OTHER INFORMATION: 53H21A HC CDR1

<400> SEQUENCE: 203

Gly Tyr Thr Phe Thr Ser Tyr Val Met His
1               5                   10

<210> SEQ ID NO 204
<211> LENGTH: 17
<212> TYPE: PRT
<213> ORGANISM: Artificial Sequence
<220> FEATURE:
<223> OTHER INFORMATION: 53H21A HC CDR2

<400> SEQUENCE: 204

Tyr Ile Ile Pro Tyr Asn Asp Gly Thr Lys Tyr Asn Glu Lys Phe Glu
1               5                   10                  15

Gly

<210> SEQ ID NO 205
<211> LENGTH: 11
<212> TYPE: PRT
<213> ORGANISM: Artificial Sequence
<220> FEATURE:
<223> OTHER INFORMATION: 53H21A HC CDR3

<400> SEQUENCE: 205

Ala Arg Trp Gly Asn Trp Asp Tyr Phe Asp Tyr
1               5                   10

<210> SEQ ID NO 206
<211> LENGTH: 10
<212> TYPE: PRT
<213> ORGANISM: Artificial Sequence
<220> FEATURE:
```

<223> OTHER INFORMATION: 53I12A HC CDR1

<400> SEQUENCE: 206

Gly Tyr Thr Phe Thr Ser Tyr Trp Ile Asn
1               5                   10

<210> SEQ ID NO 207
<211> LENGTH: 17
<212> TYPE: PRT
<213> ORGANISM: Artificial Sequence
<220> FEATURE:
<223> OTHER INFORMATION: 53I12A HC CDR2

<400> SEQUENCE: 207

Asn Ile Tyr Ala Gly Ser Ser Ser Asn Tyr Asn Glu Lys Phe Lys
1               5                   10                  15

Ser

<210> SEQ ID NO 208
<211> LENGTH: 12
<212> TYPE: PRT
<213> ORGANISM: Artificial Sequence
<220> FEATURE:
<223> OTHER INFORMATION: 53I12A HC CDR3

<400> SEQUENCE: 208

Ala Arg Ser Gly His Gly Tyr Asp Gly Phe Ala Tyr
1               5                   10

<210> SEQ ID NO 209
<211> LENGTH: 10
<212> TYPE: PRT
<213> ORGANISM: Artificial Sequence
<220> FEATURE:
<223> OTHER INFORMATION: 60A9A HC CDR1

<400> SEQUENCE: 209

Gly Tyr Ala Phe Ser Ser Tyr Trp Met Asn
1               5                   10

<210> SEQ ID NO 210
<211> LENGTH: 17
<212> TYPE: PRT
<213> ORGANISM: Artificial Sequence
<220> FEATURE:
<223> OTHER INFORMATION: 60A9A HC CDR2

<400> SEQUENCE: 210

Gln Ile Tyr Pro Gly Asp Gly Asp Thr Tyr Tyr Ser Gly Lys Phe Lys
1               5                   10                  15

Gly

<210> SEQ ID NO 211
<211> LENGTH: 14
<212> TYPE: PRT
<213> ORGANISM: Artificial Sequence
<220> FEATURE:
<223> OTHER INFORMATION: 60A9A HC CDR3

<400> SEQUENCE: 211

Ala Arg Glu Ala Ile Tyr Tyr Gly Asn Tyr Val Phe Thr Tyr
1               5                   10

<210> SEQ ID NO 212
<211> LENGTH: 10

```
<212> TYPE: PRT
<213> ORGANISM: Artificial Sequence
<220> FEATURE:
<223> OTHER INFORMATION: 39J9A HC CDR1

<400> SEQUENCE: 212

Gly Tyr Ala Phe Thr Asn Tyr Leu Ile Glu
1               5                   10

<210> SEQ ID NO 213
<211> LENGTH: 17
<212> TYPE: PRT
<213> ORGANISM: Artificial Sequence
<220> FEATURE:
<223> OTHER INFORMATION: 39J9A HC CDR2

<400> SEQUENCE: 213

Leu Ile Asn Pro Gly Ser Gly Gly Thr Asn Tyr Ile Glu Lys Phe Lys
1               5                   10                  15

Gly

<210> SEQ ID NO 214
<211> LENGTH: 13
<212> TYPE: PRT
<213> ORGANISM: Artificial Sequence
<220> FEATURE:
<223> OTHER INFORMATION: 39J9A HC CDR3

<400> SEQUENCE: 214

Ala Arg Arg Gly Asp Tyr Tyr Gly Asn Pro Phe Asp Tyr
1               5                   10

<210> SEQ ID NO 215
<211> LENGTH: 10
<212> TYPE: PRT
<213> ORGANISM: Artificial Sequence
<220> FEATURE:
<223> OTHER INFORMATION: 49H8A HC CDR1

<400> SEQUENCE: 215

Gly Tyr Thr Phe Thr Asn Tyr Trp Met Gln
1               5                   10

<210> SEQ ID NO 216
<211> LENGTH: 17
<212> TYPE: PRT
<213> ORGANISM: Artificial Sequence
<220> FEATURE:
<223> OTHER INFORMATION: 49H8A HC CDR2

<400> SEQUENCE: 216

Glu Ile Asp Pro Ser Asp Asn Tyr Thr His Tyr Asn Gln Lys Phe Lys
1               5                   10                  15

Gly

<210> SEQ ID NO 217
<211> LENGTH: 14
<212> TYPE: PRT
<213> ORGANISM: Artificial Sequence
<220> FEATURE:
<223> OTHER INFORMATION: 49H8A HC CDR3

<400> SEQUENCE: 217

Ala Arg Gly Tyr Tyr Gly Tyr Ser Pro Ser Trp Phe Ala Tyr
1               5                   10
```

```
<210> SEQ ID NO 218
<211> LENGTH: 10
<212> TYPE: PRT
<213> ORGANISM: Artificial Sequence
<220> FEATURE:
<223> OTHER INFORMATION: 51B10A HC CDR1

<400> SEQUENCE: 218

Gly Tyr Ser Phe Thr Gly Tyr Tyr Met His
1               5                   10

<210> SEQ ID NO 219
<211> LENGTH: 17
<212> TYPE: PRT
<213> ORGANISM: Artificial Sequence
<220> FEATURE:
<223> OTHER INFORMATION: 51B10A HC CDR2

<400> SEQUENCE: 219

Arg Ile Asn Pro Tyr Ser Gly Ala Thr Asn Ser Asn Gln Asn Phe Lys
1               5                   10                  15

Asp

<210> SEQ ID NO 220
<211> LENGTH: 10
<212> TYPE: PRT
<213> ORGANISM: Artificial Sequence
<220> FEATURE:
<223> OTHER INFORMATION: 51B10A HC CDR3

<400> SEQUENCE: 220

Ala Arg Ser Tyr Tyr Gly Ala Met Asp Tyr
1               5                   10

<210> SEQ ID NO 221
<211> LENGTH: 16
<212> TYPE: PRT
<213> ORGANISM: Artificial Sequence
<220> FEATURE:
<223> OTHER INFORMATION: 37C7A LC CDR1

<400> SEQUENCE: 221

Arg Ser Ser Gln Asn Leu Val His Ser Tyr Gly Asn Thr Tyr Leu His
1               5                   10                  15

<210> SEQ ID NO 222
<211> LENGTH: 7
<212> TYPE: PRT
<213> ORGANISM: Artificial Sequence
<220> FEATURE:
<223> OTHER INFORMATION: 37C7A LC CDR2

<400> SEQUENCE: 222

Lys Val Ser Asn Arg Phe Ser
1               5

<210> SEQ ID NO 223
<211> LENGTH: 9
<212> TYPE: PRT
<213> ORGANISM: Artificial Sequence
<220> FEATURE:
<223> OTHER INFORMATION: 37C7A LC CDR3

<400> SEQUENCE: 223

Ser Gln Asn Thr His Val Pro Trp Thr
1               5
```

<210> SEQ ID NO 224
<211> LENGTH: 16
<212> TYPE: PRT
<213> ORGANISM: Artificial Sequence
<220> FEATURE:
<223> OTHER INFORMATION: 38C16A LC CDR1

<400> SEQUENCE: 224

Lys Ser Ser Gln Ser Leu Leu Asp Ser Asp Gly Arg Thr Tyr Leu Asn
1               5                   10                  15

<210> SEQ ID NO 225
<211> LENGTH: 7
<212> TYPE: PRT
<213> ORGANISM: Artificial Sequence
<220> FEATURE:
<223> OTHER INFORMATION: 38C16A LC CDR2

<400> SEQUENCE: 225

Leu Val Ser Lys Leu Asp Ser
1               5

<210> SEQ ID NO 226
<211> LENGTH: 9
<212> TYPE: PRT
<213> ORGANISM: Artificial Sequence
<220> FEATURE:
<223> OTHER INFORMATION: 38C16A LC CDR3

<400> SEQUENCE: 226

Trp Gln Gly Thr His Phe Pro His Thr
1               5

<210> SEQ ID NO 227
<211> LENGTH: 17
<212> TYPE: PRT
<213> ORGANISM: Artificial Sequence
<220> FEATURE:
<223> OTHER INFORMATION: 39G8A LC CDR1

<400> SEQUENCE: 227

Lys Ser Ser Gln Ser Leu Leu Asn Ser Ser Asn Gln Lys Asn Tyr Leu
1               5                   10                  15

Ala

<210> SEQ ID NO 228
<211> LENGTH: 7
<212> TYPE: PRT
<213> ORGANISM: Artificial Sequence
<220> FEATURE:
<223> OTHER INFORMATION: 39G8A LC CDR2

<400> SEQUENCE: 228

Phe Ala Ser Thr Arg Glu Ser
1               5

<210> SEQ ID NO 229
<211> LENGTH: 9
<212> TYPE: PRT
<213> ORGANISM: Artificial Sequence
<220> FEATURE:
<223> OTHER INFORMATION: 39G8A LC CDR3

<400> SEQUENCE: 229

Gln Gln His Tyr Ser Thr Pro Tyr Thr

<210> SEQ ID NO 230
<211> LENGTH: 15
<212> TYPE: PRT
<213> ORGANISM: Artificial Sequence
<220> FEATURE:
<223> OTHER INFORMATION: 43E8A LC CDR1

<400> SEQUENCE: 230

Arg Ala Ser Glu Ser Val Asp Asn Tyr Gly Ile Ser Phe Met Asn
1               5                   10                  15

<210> SEQ ID NO 231
<211> LENGTH: 7
<212> TYPE: PRT
<213> ORGANISM: Artificial Sequence
<220> FEATURE:
<223> OTHER INFORMATION: 43E8A LC CDR2

<400> SEQUENCE: 231

Ala Ala Ser Asn Gln Gly Ser
1               5

<210> SEQ ID NO 232
<211> LENGTH: 9
<212> TYPE: PRT
<213> ORGANISM: Artificial Sequence
<220> FEATURE:
<223> OTHER INFORMATION: 43E8A LC CDR3

<400> SEQUENCE: 232

Gln Gln Ser Lys Glu Val Pro Phe Thr
1               5

<210> SEQ ID NO 233
<211> LENGTH: 11
<212> TYPE: PRT
<213> ORGANISM: Artificial Sequence
<220> FEATURE:
<223> OTHER INFORMATION: 46J3A LC CDR1

<400> SEQUENCE: 233

Arg Ala Ser Lys Asn Ile Ser Lys Tyr Leu Ala
1               5                   10

<210> SEQ ID NO 234
<211> LENGTH: 7
<212> TYPE: PRT
<213> ORGANISM: Artificial Sequence
<220> FEATURE:
<223> OTHER INFORMATION: 46J3A LC CDR2

<400> SEQUENCE: 234

Ser Gly Ser Thr Leu Gln Ser
1               5

<210> SEQ ID NO 235
<211> LENGTH: 9
<212> TYPE: PRT
<213> ORGANISM: Artificial Sequence
<220> FEATURE:
<223> OTHER INFORMATION: 46J3A LC CDR3

<400> SEQUENCE: 235

Gln Gln His Asn Glu Tyr Pro Phe Thr
1               5

```
<210> SEQ ID NO 236
<211> LENGTH: 17
<212> TYPE: PRT
<213> ORGANISM: Artificial Sequence
<220> FEATURE:
<223> OTHER INFORMATION: 46O19A LC CDR1

<400> SEQUENCE: 236

Lys Ser Ser Gln Ser Leu Leu Asn Ser Gly Asn Gln Lys Asn Tyr Leu
1               5                   10                  15

Thr

<210> SEQ ID NO 237
<211> LENGTH: 7
<212> TYPE: PRT
<213> ORGANISM: Artificial Sequence
<220> FEATURE:
<223> OTHER INFORMATION: 46O19A LC CDR2

<400> SEQUENCE: 237

Trp Ala Ser Thr Arg Glu Ser
1               5

<210> SEQ ID NO 238
<211> LENGTH: 9
<212> TYPE: PRT
<213> ORGANISM: Artificial Sequence
<220> FEATURE:
<223> OTHER INFORMATION: 46O19A LC CDR3

<400> SEQUENCE: 238

Gln Asn Asp Tyr Ser Tyr Pro Leu Thr
1               5

<210> SEQ ID NO 239
<211> LENGTH: 11
<212> TYPE: PRT
<213> ORGANISM: Artificial Sequence
<220> FEATURE:
<223> OTHER INFORMATION: 47H24A LC CDR1

<400> SEQUENCE: 239

Arg Ala Ser Gln Asp Ile Gly Ser Arg Leu Thr
1               5                   10

<210> SEQ ID NO 240
<211> LENGTH: 7
<212> TYPE: PRT
<213> ORGANISM: Artificial Sequence
<220> FEATURE:
<223> OTHER INFORMATION: 47H24A LC CDR2

<400> SEQUENCE: 240

Ala Thr Ser Ser Leu Asp Ser
1               5

<210> SEQ ID NO 241
<211> LENGTH: 9
<212> TYPE: PRT
<213> ORGANISM: Artificial Sequence
<220> FEATURE:
<223> OTHER INFORMATION: 47H24A LC CDR3

<400> SEQUENCE: 241

Leu Gln Tyr Ala Ser Ser Pro Phe Thr
```

```
<210> SEQ ID NO 242
<211> LENGTH: 11
<212> TYPE: PRT
<213> ORGANISM: Artificial Sequence
<220> FEATURE:
<223> OTHER INFORMATION: 49O5A LC CDR1

<400> SEQUENCE: 242

Glu Ala Ser Asp His Ile Asp Asn Trp Leu Ala
1               5                   10

<210> SEQ ID NO 243
<211> LENGTH: 7
<212> TYPE: PRT
<213> ORGANISM: Artificial Sequence
<220> FEATURE:
<223> OTHER INFORMATION: 49O5A LC CDR2

<400> SEQUENCE: 243

Gly Ala Thr Ser Leu Glu Thr
1               5

<210> SEQ ID NO 244
<211> LENGTH: 9
<212> TYPE: PRT
<213> ORGANISM: Artificial Sequence
<220> FEATURE:
<223> OTHER INFORMATION: 49O5A LC CDR3

<400> SEQUENCE: 244

Gln Gln Tyr Trp Ser Ser Pro Phe Thr
1               5

<210> SEQ ID NO 245
<211> LENGTH: 11
<212> TYPE: PRT
<213> ORGANISM: Artificial Sequence
<220> FEATURE:
<223> OTHER INFORMATION: 50B10A LC CDR1

<400> SEQUENCE: 245

Arg Ala Ser Gln Asp Ile Ser Asn Tyr Leu Asn
1               5                   10

<210> SEQ ID NO 246
<211> LENGTH: 7
<212> TYPE: PRT
<213> ORGANISM: Artificial Sequence
<220> FEATURE:
<223> OTHER INFORMATION: 50B10A LC CDR2

<400> SEQUENCE: 246

Tyr Thr Ser Arg Leu His Ser
1               5

<210> SEQ ID NO 247
<211> LENGTH: 9
<212> TYPE: PRT
<213> ORGANISM: Artificial Sequence
<220> FEATURE:
<223> OTHER INFORMATION: 50B10A LC CDR3

<400> SEQUENCE: 247

Gln Gln Gly Asn Thr Leu Pro Trp Thr
1               5
```

<210> SEQ ID NO 248
<211> LENGTH: 17
<212> TYPE: PRT
<213> ORGANISM: Artificial Sequence
<220> FEATURE:
<223> OTHER INFORMATION: 50H17A LC CDR1

<400> SEQUENCE: 248

Lys Ser Ser Gln Ser Leu Leu Asn Ser Gly Asn Gln Lys Asn Tyr Leu
1               5                   10                  15

Thr

<210> SEQ ID NO 249
<211> LENGTH: 7
<212> TYPE: PRT
<213> ORGANISM: Artificial Sequence
<220> FEATURE:
<223> OTHER INFORMATION: 50H17A LC CDR2

<400> SEQUENCE: 249

Trp Ala Ser Thr Arg Glu Ser
1               5

<210> SEQ ID NO 250
<211> LENGTH: 9
<212> TYPE: PRT
<213> ORGANISM: Artificial Sequence
<220> FEATURE:
<223> OTHER INFORMATION: 50H17A LC CDR3

<400> SEQUENCE: 250

Gln Asn Asp Tyr Ser Tyr Pro Leu Thr
1               5

<210> SEQ ID NO 251
<211> LENGTH: 11
<212> TYPE: PRT
<213> ORGANISM: Artificial Sequence
<220> FEATURE:
<223> OTHER INFORMATION: 50E16A LC CDR1

<400> SEQUENCE: 251

Lys Ala Ser Gln Asp Val Gly Thr Ala Val Ala
1               5                   10

<210> SEQ ID NO 252
<211> LENGTH: 7
<212> TYPE: PRT
<213> ORGANISM: Artificial Sequence
<220> FEATURE:
<223> OTHER INFORMATION: 50E16A LC CDR2

<400> SEQUENCE: 252

Trp Ala Ser Thr Arg His Thr
1               5

<210> SEQ ID NO 253
<211> LENGTH: 9
<212> TYPE: PRT
<213> ORGANISM: Artificial Sequence
<220> FEATURE:
<223> OTHER INFORMATION: 50E16A LC CDR3

<400> SEQUENCE: 253

Gln Gln Tyr Ser Ser Tyr Pro Tyr Thr

<210> SEQ ID NO 254
<211> LENGTH: 17
<212> TYPE: PRT
<213> ORGANISM: Artificial Sequence
<220> FEATURE:
<223> OTHER INFORMATION: 50F1A LC CDR1

<400> SEQUENCE: 254

Lys Ser Ser Gln Ser Leu Leu Asn Ser Gly Asn Gln Lys Asn Tyr Leu
1               5                   10                  15

Thr

<210> SEQ ID NO 255
<211> LENGTH: 7
<212> TYPE: PRT
<213> ORGANISM: Artificial Sequence
<220> FEATURE:
<223> OTHER INFORMATION: 50F1A LC CDR2

<400> SEQUENCE: 255

Trp Ala Ser Thr Arg Glu Ser
1               5

<210> SEQ ID NO 256
<211> LENGTH: 9
<212> TYPE: PRT
<213> ORGANISM: Artificial Sequence
<220> FEATURE:
<223> OTHER INFORMATION: 50F1A LC CDR3

<400> SEQUENCE: 256

Gln Asn Asp Tyr Ser Tyr Pro Leu Thr
1               5

<210> SEQ ID NO 257
<211> LENGTH: 11
<212> TYPE: PRT
<213> ORGANISM: Artificial Sequence
<220> FEATURE:
<223> OTHER INFORMATION: 54I14A LC CDR1

<400> SEQUENCE: 257

Arg Ala Ser Glu Asn Ile Tyr Ser Tyr Phe Ala
1               5                   10

<210> SEQ ID NO 258
<211> LENGTH: 7
<212> TYPE: PRT
<213> ORGANISM: Artificial Sequence
<220> FEATURE:
<223> OTHER INFORMATION: 54I14A LC CDR2

<400> SEQUENCE: 258

Asn Ala Lys Thr Leu Ala Glu
1               5

<210> SEQ ID NO 259
<211> LENGTH: 9
<212> TYPE: PRT
<213> ORGANISM: Artificial Sequence
<220> FEATURE:
<223> OTHER INFORMATION: 54I14A LC CDR3

<400> SEQUENCE: 259

Gln His His Tyr Gly Thr Pro Phe Thr
1               5

<210> SEQ ID NO 260
<211> LENGTH: 16
<212> TYPE: PRT
<213> ORGANISM: Artificial Sequence
<220> FEATURE:
<223> OTHER INFORMATION: 52K11A LC CDR1

<400> SEQUENCE: 260

Ser Ser Asn Lys Ser Leu Leu His Ser Asn Asp Ile Thr Tyr Leu Tyr
1               5                   10                  15

<210> SEQ ID NO 261
<211> LENGTH: 7
<212> TYPE: PRT
<213> ORGANISM: Artificial Sequence
<220> FEATURE:
<223> OTHER INFORMATION: 52K11A LC CDR2

<400> SEQUENCE: 261

Arg Met Ser Asn Leu Ala Ser
1               5

<210> SEQ ID NO 262
<211> LENGTH: 9
<212> TYPE: PRT
<213> ORGANISM: Artificial Sequence
<220> FEATURE:
<223> OTHER INFORMATION: 52K11A LC CDR3

<400> SEQUENCE: 262

Ala Gln Met Leu Glu Arg Pro Trp Thr
1               5

<210> SEQ ID NO 263
<211> LENGTH: 10
<212> TYPE: PRT
<213> ORGANISM: Artificial Sequence
<220> FEATURE:
<223> OTHER INFORMATION: 53H21A LC CDR1

<400> SEQUENCE: 263

Ser Ala Ser Ser Ser Val Ser Tyr Met Tyr
1               5                   10

<210> SEQ ID NO 264
<211> LENGTH: 7
<212> TYPE: PRT
<213> ORGANISM: Artificial Sequence
<220> FEATURE:
<223> OTHER INFORMATION: 53H21A LC CDR2

<400> SEQUENCE: 264

Leu Thr Ser Asn Leu Ala Ser
1               5

<210> SEQ ID NO 265
<211> LENGTH: 9
<212> TYPE: PRT
<213> ORGANISM: Artificial Sequence
<220> FEATURE:
<223> OTHER INFORMATION: 53H21A LC CDR3

<400> SEQUENCE: 265

Gln Gln Trp Ser Ser Asn Pro Trp Thr

```
1               5

<210> SEQ ID NO 266
<211> LENGTH: 11
<212> TYPE: PRT
<213> ORGANISM: Artificial Sequence
<220> FEATURE:
<223> OTHER INFORMATION: 53I12A LC CDR1

<400> SEQUENCE: 266

Ser Ala Ser Gln Gly Ile Ser Asn Tyr Leu Asn
1               5                   10

<210> SEQ ID NO 267
<211> LENGTH: 7
<212> TYPE: PRT
<213> ORGANISM: Artificial Sequence
<220> FEATURE:
<223> OTHER INFORMATION: 53I12A LC CDR2

<400> SEQUENCE: 267

Tyr Thr Ser Ser Leu His Ser
1               5

<210> SEQ ID NO 268
<211> LENGTH: 9
<212> TYPE: PRT
<213> ORGANISM: Artificial Sequence
<220> FEATURE:
<223> OTHER INFORMATION: 53I12A LC CDR3

<400> SEQUENCE: 268

Gln Gln Tyr Ser Lys Leu Pro Arg Thr
1               5

<210> SEQ ID NO 269
<211> LENGTH: 17
<212> TYPE: PRT
<213> ORGANISM: Artificial Sequence
<220> FEATURE:
<223> OTHER INFORMATION: 60A9A LC CDR1

<400> SEQUENCE: 269

Lys Ser Ser Gln Ser Leu Leu Asn Ser Ser Asn Gln Lys Asn Tyr Leu
1               5                   10                  15

Ala

<210> SEQ ID NO 270
<211> LENGTH: 7
<212> TYPE: PRT
<213> ORGANISM: Artificial Sequence
<220> FEATURE:
<223> OTHER INFORMATION: 60A9A LC CDR2

<400> SEQUENCE: 270

Phe Ala Ser Thr Arg Asp Ser
1               5

<210> SEQ ID NO 271
<211> LENGTH: 9
<212> TYPE: PRT
<213> ORGANISM: Artificial Sequence
<220> FEATURE:
<223> OTHER INFORMATION: 60A9A LC CDR3

<400> SEQUENCE: 271
```

Gln Gln His Tyr Ser Thr Pro Leu Thr
1               5

<210> SEQ ID NO 272
<211> LENGTH: 11
<212> TYPE: PRT
<213> ORGANISM: Artificial Sequence
<220> FEATURE:
<223> OTHER INFORMATION: 39J9A LC CDR1

<400> SEQUENCE: 272

Arg Ala Ser Glu Asn Ile Tyr Tyr Ser Leu Ala
1               5                   10

<210> SEQ ID NO 273
<211> LENGTH: 7
<212> TYPE: PRT
<213> ORGANISM: Artificial Sequence
<220> FEATURE:
<223> OTHER INFORMATION: 39J9A LC CDR2

<400> SEQUENCE: 273

Asn Ala Asp Thr Leu Glu Asp
1               5

<210> SEQ ID NO 274
<211> LENGTH: 9
<212> TYPE: PRT
<213> ORGANISM: Artificial Sequence
<220> FEATURE:
<223> OTHER INFORMATION: 39J9A LC CDR3

<400> SEQUENCE: 274

Lys Gln Ala Tyr Asp Val Pro Leu Thr
1               5

<210> SEQ ID NO 275
<211> LENGTH: 10
<212> TYPE: PRT
<213> ORGANISM: Artificial Sequence
<220> FEATURE:
<223> OTHER INFORMATION: 49H8A LC CDR1

<400> SEQUENCE: 275

Ser Ala Ser Ser Ser Val Ser Tyr Met Tyr
1               5                   10

<210> SEQ ID NO 276
<211> LENGTH: 7
<212> TYPE: PRT
<213> ORGANISM: Artificial Sequence
<220> FEATURE:
<223> OTHER INFORMATION: 49H8A LC CDR2

<400> SEQUENCE: 276

Leu Thr Ser Asn Leu Ala Ser
1               5

<210> SEQ ID NO 277
<211> LENGTH: 9
<212> TYPE: PRT
<213> ORGANISM: Artificial Sequence
<220> FEATURE:
<223> OTHER INFORMATION: 49H8A LC CDR3

<400> SEQUENCE: 277

Gln Gln Trp Ser Ser Asn Pro Pro Thr

-continued

<210> SEQ ID NO 278
<211> LENGTH: 11
<212> TYPE: PRT
<213> ORGANISM: Artificial Sequence
<220> FEATURE:
<223> OTHER INFORMATION: 51B10A LC CDR1

<400> SEQUENCE: 278

Lys Ala Ser Gln Asp Ile Asn Ser Tyr Leu Ser
1               5                   10

<210> SEQ ID NO 279
<211> LENGTH: 7
<212> TYPE: PRT
<213> ORGANISM: Artificial Sequence
<220> FEATURE:
<223> OTHER INFORMATION: 51B10A LC CDR2

<400> SEQUENCE: 279

Arg Ala Asn Arg Leu Val Asp
1               5

<210> SEQ ID NO 280
<211> LENGTH: 9
<212> TYPE: PRT
<213> ORGANISM: Artificial Sequence
<220> FEATURE:
<223> OTHER INFORMATION: 51B10A LC CDR3

<400> SEQUENCE: 280

Leu Gln Tyr Asp Glu Phe Pro Leu Thr
1               5

<210> SEQ ID NO 281
<211> LENGTH: 574
<212> TYPE: PRT
<213> ORGANISM: Homo sapiens

<400> SEQUENCE: 281

Met Cys Pro Arg Ala Ala Arg Ala Pro Ala Thr Leu Leu Leu Ala Leu
1               5                   10                  15

Gly Ala Val Leu Trp Pro Ala Ala Gly Ala Trp Glu Leu Thr Ile Leu
                20                  25                  30

His Thr Asn Asp Val His Ser Arg Leu Glu Gln Thr Ser Glu Asp Ser
            35                  40                  45

Ser Lys Cys Val Asn Ala Ser Arg Cys Met Gly Gly Val Ala Arg Leu
        50                  55                  60

Phe Thr Lys Val Gln Gln Ile Arg Arg Ala Glu Pro Asn Val Leu Leu
65                  70                  75                  80

Leu Asp Ala Gly Asp Gln Tyr Gln Gly Thr Ile Trp Phe Thr Val Tyr
                85                  90                  95

Lys Gly Ala Glu Val Ala His Phe Met Asn Ala Leu Arg Tyr Asp Ala
                100                 105                 110

Met Ala Leu Gly Asn His Glu Phe Asp Asn Gly Val Glu Gly Leu Ile
            115                 120                 125

Glu Pro Leu Leu Lys Glu Ala Lys Phe Pro Ile Leu Ser Ala Asn Ile
        130                 135                 140

Lys Ala Lys Gly Pro Leu Ala Ser Gln Ile Ser Gly Leu Tyr Leu Pro
145                 150                 155                 160

```
Tyr Lys Val Leu Pro Val Gly Asp Glu Val Gly Ile Val Gly Tyr
            165                 170                 175

Thr Ser Lys Glu Thr Pro Phe Leu Ser Asn Pro Gly Thr Asn Leu Val
            180                 185                 190

Phe Glu Asp Glu Ile Thr Ala Leu Gln Pro Glu Val Asp Lys Leu Lys
            195                 200                 205

Thr Leu Asn Val Asn Lys Ile Ala Leu Gly His Ser Gly Phe Glu
    210                 215                 220

Met Asp Lys Leu Ile Ala Gln Lys Val Arg Gly Val Asp Val Val Val
225                 230                 235                 240

Gly Gly His Ser Asn Thr Phe Leu Tyr Thr Gly Asn Pro Pro Ser Lys
                245                 250                 255

Glu Val Pro Ala Gly Lys Tyr Pro Phe Ile Val Thr Ser Asp Asp Gly
            260                 265                 270

Arg Lys Val Pro Val Gln Ala Tyr Ala Phe Gly Lys Tyr Leu Gly
    275                 280                 285

Tyr Leu Lys Ile Glu Phe Asp Glu Arg Gly Asn Val Ile Ser Ser His
        290                 295                 300

Gly Asn Pro Ile Leu Leu Asn Ser Ser Ile Pro Glu Asp Pro Ser Ile
305                 310                 315                 320

Lys Ala Asp Ile Asn Lys Trp Arg Ile Lys Leu Asp Asn Tyr Ser Thr
                325                 330                 335

Gln Glu Leu Gly Lys Thr Ile Val Tyr Leu Asp Gly Ser Ser Gln Ser
                340                 345                 350

Cys Arg Phe Arg Glu Cys Asn Met Gly Asn Leu Ile Cys Asp Ala Met
            355                 360                 365

Ile Asn Asn Asn Leu Arg His Thr Asp Glu Met Phe Trp Asn His Val
    370                 375                 380

Ser Met Cys Ile Leu Asn Gly Gly Ile Arg Ser Pro Ile Asp Glu
385                 390                 395                 400

Arg Asn Asn Gly Thr Ile Thr Trp Glu Asn Leu Ala Ala Val Leu Pro
                405                 410                 415

Phe Gly Gly Thr Phe Asp Leu Val Gln Leu Lys Gly Ser Thr Leu Lys
            420                 425                 430

Lys Ala Phe Glu His Ser Val His Arg Tyr Gly Gln Ser Thr Gly Glu
            435                 440                 445

Phe Leu Gln Val Gly Gly Ile His Val Val Tyr Asp Leu Ser Arg Lys
    450                 455                 460

Pro Gly Asp Arg Val Val Lys Leu Asp Val Leu Cys Thr Lys Cys Arg
465                 470                 475                 480

Val Pro Ser Tyr Asp Pro Leu Lys Met Asp Glu Val Tyr Lys Val Ile
                485                 490                 495

Leu Pro Asn Phe Leu Ala Asn Gly Gly Asp Gly Phe Gln Met Ile Lys
            500                 505                 510

Asp Glu Leu Leu Arg His Asp Ser Gly Asp Gln Asp Ile Asn Val Val
            515                 520                 525

Ser Thr Tyr Ile Ser Lys Met Lys Val Ile Tyr Pro Ala Val Glu Gly
    530                 535                 540

Arg Ile Lys Phe Ser Thr Gly Ser His Cys His Gly Ser Phe Ser Leu
545                 550                 555                 560

Ile Phe Leu Ser Leu Trp Ala Val Ile Phe Val Leu Tyr Gln
                565                 570
```

<210> SEQ ID NO 282
<211> LENGTH: 121
<212> TYPE: PRT
<213> ORGANISM: Artificial Sequence
<220> FEATURE:
<223> OTHER INFORMATION: 60A9-H1 Heavy Chain Variable Region

<400> SEQUENCE: 282

```
Glu Val Gln Leu Val Glu Ser Gly Gly Gly Leu Val Gln Pro Gly Gln
1               5                   10                  15

Ser Leu Lys Leu Ser Cys Lys Ala Ser Gly Tyr Ala Phe Ser Ser Tyr
            20                  25                  30

Trp Met Asn Trp Val Arg Gln Ala Pro Gly Lys Gly Leu Glu Trp Met
        35                  40                  45

Gly Gln Ile Tyr Pro Gly Asp Gly Asp Thr Tyr Tyr Asn Pro Ser Val
    50                  55                  60

Lys Gly Arg Phe Thr Ile Ser Ala Asp Thr Ser Lys Asn Thr Ala Tyr
65                  70                  75                  80

Leu Gln Leu Asn Asn Leu Arg Ala Glu Asp Thr Ala Val Tyr Tyr Cys
                85                  90                  95

Ala Arg Glu Ala Ile Tyr Tyr Gly Asn Tyr Val Phe Thr Tyr Trp Gly
            100                 105                 110

Gln Gly Thr Leu Val Thr Val Ser Ser
        115                 120
```

<210> SEQ ID NO 283
<211> LENGTH: 121
<212> TYPE: PRT
<213> ORGANISM: Artificial Sequence
<220> FEATURE:
<223> OTHER INFORMATION: 60A9-H2 Heavy Chain Variable Region

<400> SEQUENCE: 283

```
Glu Val Gln Leu Val Glu Ser Gly Gly Gly Leu Val Gln Pro Gly Gly
1               5                   10                  15

Ser Leu Arg Leu Ser Cys Lys Ala Ser Gly Tyr Ala Phe Ser Ser Tyr
            20                  25                  30

Trp Met Asn Trp Val Arg Gln Ala Pro Gly Lys Gly Leu Glu Trp Val
        35                  40                  45

Gly Gln Ile Tyr Pro Gly Asp Gly Asp Thr Tyr Tyr Asn Pro Ser Val
    50                  55                  60

Lys Gly Arg Phe Thr Ile Ser Ala Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Ile Tyr Tyr Gly Asn Tyr Val Phe Thr Tyr Trp Gly
            100                 105                 110

Gln Gly Thr Leu Val Thr Val Ser Ser
        115                 120
```

<210> SEQ ID NO 284
<211> LENGTH: 121
<212> TYPE: PRT
<213> ORGANISM: Artificial Sequence
<220> FEATURE:
<223> OTHER INFORMATION: 60A9-H3 Heavy Chain Variable Region

<400> SEQUENCE: 284

```
Glu Val Gln Leu Val Glu Ser Gly Gly Gly Leu Val Gln Pro Gly Gln
1               5                   10                  15
```

```
Ser Leu Lys Leu Ser Cys Lys Ala Ser Gly Tyr Ala Phe Ser Ser Tyr
        20                  25                  30

Trp Met Asn Trp Val Arg Gln Ala Pro Gly Lys Gly Leu Glu Trp Ile
        35                  40                  45

Gly Gln Ile Tyr Pro Gly Asp Gly Asp Thr Tyr Tyr Asn Pro Ser Val
50                  55                  60

Lys Gly Arg Ala Thr Leu Ser Ala Asp Lys Ser Lys Asn Thr Ala Tyr
65                  70                  75                  80

Leu Gln Leu Asn Asn Leu Arg Ala Glu Asp Thr Ala Val Tyr Tyr Cys
                85                  90                  95

Ala Arg Glu Ala Ile Tyr Tyr Gly Asn Tyr Val Phe Thr Tyr Trp Gly
            100                 105                 110

Gln Gly Thr Leu Val Thr Val Ser Ser
            115                 120

<210> SEQ ID NO 285
<211> LENGTH: 121
<212> TYPE: PRT
<213> ORGANISM: Artificial Sequence
<220> FEATURE:
<223> OTHER INFORMATION: 60A9-H4 Heavy Chain Variable Region

<400> SEQUENCE: 285

Glu Val Gln Leu Val Glu Ser Gly Gly Gly Leu Val Gln Pro Gly Gln
1               5                   10                  15

Ser Leu Lys Leu Ser Cys Lys Ala Ser Gly Tyr Ala Phe Ser Ser Tyr
            20                  25                  30

Trp Met Asn Trp Val Arg Gln Ala Pro Gly Lys Gly Leu Glu Trp Ile
        35                  40                  45

Gly Gln Ile Tyr Pro Gly Asp Gly Asp Thr Tyr Tyr Ser Gly Ser Val
50                  55                  60

Lys Gly Arg Ala Thr Leu Ser Ala Asp Lys Ser Lys Asn Thr Ala Tyr
65                  70                  75                  80

Leu Gln Leu Asn Asn Leu Arg Ala Glu Asp Thr Ala Val Tyr Tyr Cys
                85                  90                  95

Ala Arg Glu Ala Ile Tyr Tyr Gly Asn Tyr Val Phe Thr Tyr Trp Gly
            100                 105                 110

Gln Gly Thr Leu Val Thr Val Ser Ser
            115                 120

<210> SEQ ID NO 286
<211> LENGTH: 121
<212> TYPE: PRT
<213> ORGANISM: Artificial Sequence
<220> FEATURE:
<223> OTHER INFORMATION: 60A9-H5 Heavy Chain Variable Region

<400> SEQUENCE: 286

Glu Val Gln Leu Val Glu Ser Gly Gly Gly Leu Val Gln Pro Gly Gln
1               5                   10                  15

Ser Leu Lys Leu Ser Cys Lys Ala Ser Gly Tyr Ala Phe Ser Ser Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asp Gly Asp Thr Tyr Tyr Ser Gly Lys Phe
50                  55                  60

Lys Gly Arg Ala Thr Leu Ser Ala Asp Lys Ser Lys Asn Thr Ala Tyr
```

```
            65                  70                  75                  80
Leu Gln Leu Asn Asn Leu Arg Ala Glu Asp Thr Ala Val Tyr Tyr Cys
                85                  90                  95

Ala Arg Glu Ala Ile Tyr Tyr Gly Asn Tyr Val Phe Thr Tyr Trp Gly
            100                 105                 110

Gln Gly Thr Leu Val Thr Val Ser Ser
            115                 120

<210> SEQ ID NO 287
<211> LENGTH: 121
<212> TYPE: PRT
<213> ORGANISM: Artificial Sequence
<220> FEATURE:
<223> OTHER INFORMATION: 39G8-H1 Heavy Chain Variable Region

<400> SEQUENCE: 287

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Glu Ile Asp Pro Ser Gly Gly Tyr Thr Asn Tyr Ala Gln Lys Phe
    50                  55                  60

Gln Gly Arg Ser Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Tyr Tyr Tyr Gly Ser Ser Gly Thr Met Asp Tyr Trp Gly
            100                 105                 110

Gln Gly Thr Leu Val Thr Val Ser Ser
            115                 120

<210> SEQ ID NO 288
<211> LENGTH: 121
<212> TYPE: PRT
<213> ORGANISM: Artificial Sequence
<220> FEATURE:
<223> OTHER INFORMATION: 39G8-H2 Heavy Chain Variable Region

<400> SEQUENCE: 288

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45

Gly Glu Ile Asp Pro Ser Gly Gly Tyr Thr Asn Tyr Ala Gln Lys Phe
    50                  55                  60

Gln Gly Arg Ser Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Tyr Tyr Tyr Gly Ser Ser Gly Thr Met Asp Tyr Trp Gly
            100                 105                 110

Gln Gly Thr Leu Val Thr Val Ser Ser
            115                 120
```

<210> SEQ ID NO 289
<211> LENGTH: 121
<212> TYPE: PRT
<213> ORGANISM: Artificial Sequence
<220> FEATURE:
<223> OTHER INFORMATION: 39G8-H3 Heavy Chain Variable Region

<400> SEQUENCE: 289

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Glu Ile Asp Pro Ser Gly Gly Tyr Thr Asn Tyr Asn Gln Lys Phe
    50                  55                  60

Gln Gly Arg Ser Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asn Tyr Tyr Tyr Gly Ser Ser Gly Met Asp Tyr Trp Gly
            100                 105                 110

Gln Gly Thr Leu Val Thr Val Ser Ser
        115                 120
```

<210> SEQ ID NO 290
<211> LENGTH: 113
<212> TYPE: PRT
<213> ORGANISM: Artificial Sequence
<220> FEATURE:
<223> OTHER INFORMATION: 60A9-L1 Light Chain Variable Region

<400> SEQUENCE: 290

```
Asp Ile Gln Met Thr Gln Ser Pro Ser Leu Leu Ser Ala Ser Leu Gly
1               5                   10                  15

Asp Arg Val Thr Ile Thr Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Phe Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Glu Pro Glu Asp Phe Ala Thr Tyr Tyr Cys Gln Gln
                85                  90                  95

His Tyr Ser Thr Pro Leu Thr Phe Gly Gly Gly Thr Lys Leu Glu Ile
            100                 105                 110

Lys
```

<210> SEQ ID NO 291
<211> LENGTH: 113
<212> TYPE: PRT
<213> ORGANISM: Artificial Sequence
<220> FEATURE:
<223> OTHER INFORMATION: 60A9-L2 Light Chain Variable Region

<400> SEQUENCE: 291

```
Asp Ile Val Met Thr Gln Ser Pro Ser Ser Leu Ser Ala Ser Leu Gly
1               5                   10                  15
```

Asp Arg Val Thr Ile Thr Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Phe Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Glu Pro Glu Asp Phe Ala Thr Tyr Tyr Cys Gln Gln
                85                  90                  95

His Tyr Ser Thr Pro Leu Thr Phe Gly Gly Gly Thr Lys Leu Glu Ile
            100                 105                 110

Lys

<210> SEQ ID NO 292
<211> LENGTH: 113
<212> TYPE: PRT
<213> ORGANISM: Artificial Sequence
<220> FEATURE:
<223> OTHER INFORMATION: 60A9-L3 Light Chain Variable Region

<400> SEQUENCE: 292

Asp Ile Gln Met Thr Gln Ser Pro Ser Leu Leu Ser Ala Ser Leu Gly
1               5                   10                  15

Asp Arg Val Thr Ile Thr Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Glu Pro Glu Asp Phe Ala Thr Tyr Tyr Cys Gln Gln
                85                  90                  95

His Tyr Ser Thr Pro Leu Thr Phe Gly Gly Gly Thr Lys Leu Glu Ile
            100                 105                 110

Lys

<210> SEQ ID NO 293
<211> LENGTH: 113
<212> TYPE: PRT
<213> ORGANISM: Artificial Sequence
<220> FEATURE:
<223> OTHER INFORMATION: 60A9-L4 Light Chain Variable Region

<400> SEQUENCE: 293

Asp Ile Val Met Thr Gln Ser Pro Ser Leu Leu Ser Ala Ser Leu Gly
1               5                   10                  15

Asp Arg Val Thr Ile Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Glu Pro Glu Asp Phe Ala Thr Tyr Phe Cys Gln Gln
                85                  90                  95

His Tyr Ser Thr Pro Leu Thr Phe Gly Ala Gly Thr Lys Leu Glu Ile
            100                 105                 110

Lys

<210> SEQ ID NO 294
<211> LENGTH: 113
<212> TYPE: PRT
<213> ORGANISM: Artificial Sequence
<220> FEATURE:
<223> OTHER INFORMATION: 39G8-L3 Light Chain Variable Region

<400> SEQUENCE: 294

Asp Ile Val Met Thr Gln Ser Pro Asp Ser Leu Ala Val Ser Leu Gly
1               5                   10                  15

Glu Arg Ala Thr Met Ser Cys Lys Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Pro Pro Lys Leu Leu Val Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

His Tyr Ser Thr Pro Tyr Thr Phe Gly Gly Gly Thr Lys Val Glu Ile
            100                 105                 110

Lys

<210> SEQ ID NO 295
<211> LENGTH: 121
<212> TYPE: PRT
<213> ORGANISM: Artificial Sequence
<220> FEATURE:
<223> OTHER INFORMATION: 60A9-H6 Heavy Chain Variable Region

<400> SEQUENCE: 295

Gln Val Gln Leu Val Gln Ser Gly Ala Glu Val Lys Arg Pro Gly Ser
1               5                   10                  15

Ser Val Thr Val Ser Cys Lys Ala Ser Gly Tyr Ala Phe Ser Ser Tyr
            20                  25                  30

Trp Met Asn Trp Val Arg Gln Ala Pro Gly Arg Gly Leu Glu Trp Ile
        35                  40                  45

Gly Gln Ile Tyr Pro Gly Asp Gly Asp Thr Tyr Tyr Ala Pro Arg Phe
    50                  55                  60

Gln Gly Arg Ala Thr Leu Thr Ala Asp Lys Ser Thr Ser Thr Ala Tyr
65                  70                  75                  80

Leu Glu Leu Asn Ser Leu Arg Pro Glu Asp Thr Ala Val Tyr Phe Cys
                85                  90                  95

Ala Arg Glu Ala Ile Tyr Tyr Gly Asn Tyr Val Phe Thr Tyr Trp Gly
            100                 105                 110

Gln Gly Thr Leu Val Thr Val Ser Ser
        115                 120

<210> SEQ ID NO 296
<211> LENGTH: 121
<212> TYPE: PRT

<213> ORGANISM: Artificial Sequence
<220> FEATURE:
<223> OTHER INFORMATION: 60A9-H7 Heavy Chain Variable Region

<400> SEQUENCE: 296

Gln Val Gln Leu Val Gln Ser Gly Ala Glu Val Lys Lys Pro Gly Ser
1               5                   10                  15

Ser Val Thr Val Ser Cys Lys Ala Ser Gly Tyr Ala Phe Ser Ser Tyr
            20                  25                  30

Trp Met Asn Trp Val Arg Gln Ala Pro Gly Arg Gly Leu Glu Trp Ile
        35                  40                  45

Gly Gln Ile Tyr Pro Gly Asp Gly Asp Thr Tyr Tyr Ala Pro Lys Phe
    50                  55                  60

Gln Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Glu Ala Ile Tyr Tyr Gly Asn Tyr Val Phe Thr Tyr Trp Gly
            100                 105                 110

Gln Gly Thr Leu Val Thr Val Ser Ser
        115                 120

<210> SEQ ID NO 297
<211> LENGTH: 121
<212> TYPE: PRT
<213> ORGANISM: Artificial Sequence
<220> FEATURE:
<223> OTHER INFORMATION: 60A9-H8 Heavy Chain Variable Region

<400> SEQUENCE: 297

Gln Val Gln Leu Val Gln Ser Gly Ala Glu Val Lys Lys Pro Gly Ser
1               5                   10                  15

Ser Val Thr Val Ser Cys Lys Ala Ser Gly Tyr Ala Phe Ser Ser Tyr
            20                  25                  30

Trp Met Asn Trp Val Arg Gln Ala Pro Gly Arg Gly Leu Glu Trp Ile
        35                  40                  45

Gly Gln Ile Tyr Pro Gly Asp Gly Asp Thr Tyr Tyr Ser Gly Lys Phe
    50                  55                  60

Gln Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Glu Ala Ile Tyr Tyr Gly Asn Tyr Val Phe Thr Tyr Trp Gly
            100                 105                 110

Gln Gly Thr Leu Val Thr Val Ser Ser
        115                 120

<210> SEQ ID NO 298
<211> LENGTH: 121
<212> TYPE: PRT
<213> ORGANISM: Artificial Sequence
<220> FEATURE:
<223> OTHER INFORMATION: 60A9-H9 Heavy Chain Variable Region

<400> SEQUENCE: 298

Gln Val Gln Leu Val Gln Ser Gly Ala Glu Val Lys Arg Pro Gly Ser
1               5                   10                  15

Ser Val Thr Val Ser Cys Lys Ala Ser Gly Tyr Ala Phe Ser Ser Tyr
            20                  25                  30

-continued

```
Trp Met Asn Trp Val Arg Gln Ala Pro Gly Arg Gly Leu Glu Trp Ile
        35                  40                  45

Gly Gln Ile Tyr Pro Gly Asp Gly Asp Thr Tyr Tyr Ser Gly Lys Phe
        50                  55                  60

Lys Gly Arg Ala Thr Leu Ser Ala Asp Lys Ser Lys Asn Thr Ala Tyr
 65                  70                  75                  80

Leu Gln Leu Asn Asn Leu Arg Ala Glu Asp Thr Ala Val Tyr Tyr Cys
                 85                  90                  95

Ala Arg Glu Ala Ile Tyr Tyr Gly Asn Tyr Val Phe Thr Tyr Trp Gly
                100                 105                 110

Gln Gly Thr Leu Val Thr Val Ser Ser
        115                 120

<210> SEQ ID NO 299
<211> LENGTH: 113
<212> TYPE: PRT
<213> ORGANISM: Artificial Sequence
<220> FEATURE:
<223> OTHER INFORMATION: 60A9-L5  Light Chain Variable Region

<400> SEQUENCE: 299

Glu Ile Val Met Thr Gln Ser Pro Gly Thr Gln Ser Leu Ser Pro Gly
 1               5                  10                  15

Glu Arg Ala Thr Leu Ser Cys Lys Ser Ser Gln Ser Leu Leu Asn Ser
                20                  25                  30

Ser Asn Gln Lys Asn Tyr Leu Ala Trp Tyr Gln Gln Arg Pro Gly Gln
                35                  40                  45

Ala Pro Arg Leu Leu Val Tyr Phe Ala Ser Thr Arg Asp Ser Gly Val
 50                  55                  60

Ala Asp Arg Phe Ser Gly Ser Gly Ser Gly Thr Asp Phe Thr Leu Thr
 65                  70                  75                  80

Ile Ser Arg Leu Glu Pro Glu Asp Phe Ala Val Tyr Phe Cys Gln Gln
                85                  90                  95

His Tyr Ser Thr Pro Leu Thr Phe Gly Gln Gly Thr Lys Val Glu Val
                100                 105                 110

Lys
```

ANTI-CD73 ANTIBODIES AND USES THEREOF

CROSS REFERENCE TO RELATED APPLICATIONS

This application is a Section 371 of International Application No. PCT/US2019/020688, filed Mar. 5, 2019, which published in the English language on Sep. 12, 2019 under International Publication No. WO 2019/173291 A1, which claims priority to U.S. Provisional Application No. 62/640,955, filed Mar. 9, 2018; U.S. Provisional Application No. 62/721,044, filed Aug. 22, 2018; and U.S. Provisional Application No. 62/786,598, filed Dec. 31, 2018. Each disclosure is incorporated herein by reference in its entirety.

FIELD OF THE INVENTION

This invention relates to monoclonal anti-CD73 antibodies, nucleic acids and expression vectors encoding the antibodies, recombinant cells containing the vectors, and compositions comprising the antibodies. Methods of making the antibodies, and methods of using the antibodies to treat diseases associated with CD73 such as cancer and inflammatory diseases and/or associated complications are also provided.

REFERENCE TO SEQUENCE LISTING SUBMITTED ELECTRONICALLY

This application contains a sequence listing, which is submitted electronically via EFS-Web as an ASCII formatted sequence listing with a file name "065799_10US2_Sequence_Listing" and a creation date of Aug. 18, 2020 and having a size of 115 kb. The sequence listing submitted via EFS-Web is part of the specification and is herein incorporated by reference in its entirety.

BACKGROUND OF THE INVENTION

CD73, also known as ecto-5'-nucleotidase (ecto-5'-NT or EC 3.1.3.5), is a cell surface phosphatase that catalyzes the dephosphorylation of extracellular AMP to produce adenosine. Although it's a glycophosphatidylinositol (GPI)-anchored protein, CD73 can also be shed to yield a catalytically active form (Arias et al., J Cell Biol. 1997; 136(2): 421-31). Physiologically, CD73 is induced by hypoxia to control inflammation at injury sites (Bours et al., Pharmacol Ther 2006; 112:358-404). Pathologically, CD73 is often found overexpressed on regulatory T cells (Tregs) and tumor cells (Paul et al., Trends Immunol 2012; 33:231-237). Elevated CD73 activity leads to the accumulation of adenosine in the tumor microenvironment (TME).

Accumulating evidence indicates that CD73 activity in tumor sites is one of the major factors shaping a pro-tumor TME that is critical for tumor growth and survival (Whiteside, Expert Rev. Anticancer Ther. 2017; 17(6):527-35). Extracellular ATP-adenosine homeostasis is determined by the activities of CD39, which converts ATP to AMP, and CD73, which uses AMP to produce adenosine. Through binding to adenosine receptors A2a and A2b, adenosine suppresses both innate and adaptive immunities by regulating many immune cells such as macrophages (Csoka et al., FASEB J 2012; 26:376-386), dendritic cells (Panther et al., Blood 2003; 101:3985-3990), natural killer cells (Hausler et al., Cancer Immunol Immunother 2011; 60:1405-1418), and T effector cells (Hoskin et al., Int J Oncol 2008; 32:527-535). Therefore, it has been hypothesized that immune suppression by adenosine may be alleviated by inhibiting the enzymatic activity of CD73 in the TME. Indeed, in vivo animal studies (Jin et al., Cancer Res 2010; 70:2245-2255; Stagg et al., Cancer Res 2011; 71:2890-2900) indicate that inhibiting the enzymatic activity of CD73 suppresses tumor formation and growth, suggesting that CD73 is a promising target for cancer therapy. Monoclonal antibodies that inhibit CD73 enzymatic activity and/or reduce CD73 content on cell surface (i.e., by inducing CD73 internalization) can be efficacious in treating cancer alone as monotherapy or in combination with other immuno-oncology drugs and/or other types of anti-cancer therapies.

BRIEF SUMMARY OF THE INVENTION

In one general aspect, the invention relates to isolated monoclonal antibodies or antigen-binding fragments thereof that bind CD73.

Provided are isolated monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of:

(1) SEQ ID NOs:89, 90, 91, 149, 150 and 151, respectively;
(2) SEQ ID NOs:41, 42, 43, 101, 102 and 103, respectively;
(3) SEQ ID NOs:44, 45, 46, 104, 105 and 106, respectively;
(4) SEQ ID NOs:47, 48, 49, 107, 108 and 109, respectively;
(5) SEQ ID NOs:50, 51, 52, 110, 111 and 112, respectively;
(6) SEQ ID NOs:53, 54, 55, 113, 114 and 115, respectively;
(7) SEQ ID NOs:56, 57, 58, 116, 117 and 118, respectively;
(8) SEQ ID NOs:59, 60, 61, 119, 120 and 121, respectively;
(9) SEQ ID NOs:62, 63, 64, 122, 123 and 124, respectively;
(10) SEQ ID NOs:65, 66, 67, 125, 126 and 127, respectively;
(11) SEQ ID NOs:68, 69, 70, 128, 129 and 130, respectively;
(12) SEQ ID NOs:71, 72, 73, 131, 132 and 133, respectively;
(13) SEQ ID NOs:74, 75, 76, 134, 135 and 136, respectively;
(14) SEQ ID NOs:77, 78, 79, 137, 138 and 139, respectively;
(15) SEQ ID NOs:80, 81, 82, 140, 141 and 142, respectively;
(16) SEQ ID NOs:83, 84, 85, 143, 144 and 145, respectively;
(17) SEQ ID NOs:86, 87, 88, 146, 147 and 148, respectively;
(18) SEQ ID NOs:92, 93, 94, 152, 153 and 154, respectively;
(19) SEQ ID NOs:95, 96, 97, 155, 156 and 157, respectively; or
(20) SEQ ID NOs:98, 99, 100, 158, 159 and 160, respectively;
wherein the antibody or antigen-binding fragment thereof specifically binds to CD73, preferably human CD73.

Provided are isolated monoclonal antibodies or antigen-binding fragments thereof comprising a heavy chain complementarity determining region 1 (HCDR1), HCDR2, HCDR3, a light chain complementarity determining region 1 (LCDR1), LCDR2, and LCDR3, having the polypeptide sequences of:
- (1) SEQ ID NOs:209, 210, 211, 269, 270 and 271, respectively;
- (2) SEQ ID NOs:161, 162, 163, 221, 222 and 223, respectively;
- (3) SEQ ID NOs:164, 165, 166, 224, 225 and 226, respectively;
- (4) SEQ ID NOs:167, 168, 169, 227, 228 and 229, respectively;
- (5) SEQ ID NOs:170, 171, 172, 230, 231 and 232, respectively;
- (6) SEQ ID NOs:173, 174, 175, 233, 234 and 235, respectively;
- (7) SEQ ID NOs:176, 177, 178, 236, 237 and 238, respectively;
- (8) SEQ ID NOs:179, 180, 181, 239, 240 and 241, respectively;
- (9) SEQ ID NOs:182, 183, 184, 242, 243 and 244, respectively;
- (10) SEQ ID NOs:185, 186, 187, 245, 246 and 247, respectively;
- (11) SEQ ID NOs:188, 189, 190, 248, 249 and 250, respectively;
- (12) SEQ ID NOs:191, 192, 193, 251, 252 and 253, respectively;
- (13) SEQ ID NOs:194, 195, 196, 254, 255 and 256, respectively;
- (14) SEQ ID NOs:197, 198, 199, 257, 258 and 259, respectively;
- (15) SEQ ID NOs:200, 201, 202, 260, 261 and 262, respectively;
- (16) SEQ ID NOs:203, 204, 205, 263, 264 and 265, respectively;
- (17) SEQ ID NOs:206, 207, 208, 266, 267 and 268, respectively;
- (18) SEQ ID NOs:212, 213, 214, 272, 273 and 274, respectively;
- (19) SEQ ID NOs:215, 216, 217, 275, 276 and 277, respectively; or
- (20) SEQ ID NOs:218, 219, 220, 278, 279 and 280, respectively;

wherein the antibody or antigen-binding fragment thereof specifically binds to CD73, preferably human CD73.

In certain embodiments, the isolated monoclonal antibody or antigen-binding fragment thereof comprises a heavy chain variable region having a polypeptide sequence at least 95%, at least 96%, at least 97%, at least 98%, or at least 99% identical to SEQ ID NO:33, 1, 3, 5, 7, 9, 11, 13, 15, 17, 19, 21, 23, 25, 27, 29, 31, 35, 37 or 39, or a light chain variable region having a polypeptide sequence at least 95%, at least 96%, at least 97%, at least 98%, or at least 99% identical to SEQ ID NO:34, 2, 4, 6, 8, 10, 12, 14, 16, 18, 20, 22, 24, 26, 28, 30, 32, 36, 38 or 40.

In certain embodiments, the isolated monoclonal antibody or antigen-binding fragment thereof comprises:
- (a) a heavy chain variable region having the polypeptide sequence of SEQ ID NO:33, and a light chain variable region having the polypeptide sequence of SEQ ID NO:34;
- (b) a heavy chain variable region having the polypeptide sequence of SEQ ID NO:1, and a light chain variable region having the polypeptide sequence of SEQ ID NO:2;
- (c) a heavy chain variable region having the polypeptide sequence of SEQ ID NO:3, and a light chain variable region having the polypeptide sequence of SEQ ID NO:4;
- (d) a heavy chain variable region having the polypeptide sequence of SEQ ID NO:5, and a light chain variable region having the polypeptide sequence of SEQ ID NO:6;
- (e) a heavy chain variable region having the polypeptide sequence of SEQ ID NO:7, and a light chain variable region having the polypeptide sequence of SEQ ID NO:8;
- (f) a heavy chain variable region having the polypeptide sequence of SEQ ID NO:9, and a light chain variable region having the polypeptide sequence of SEQ ID NO:10;
- (g) a heavy chain variable region having the polypeptide sequence of SEQ ID NO:11, and a light chain variable region having the polypeptide sequence of SEQ ID NO:12;
- (h) a heavy chain variable region having the polypeptide sequence of SEQ ID NO:13, and a light chain variable region having the polypeptide sequence of SEQ ID NO:14;
- (i) a heavy chain variable region having the polypeptide sequence of SEQ ID NO:15, and a light chain variable region having the polypeptide sequence of SEQ ID NO:16;
- (j) a heavy chain variable region having the polypeptide sequence of SEQ ID NO:17, and a light chain variable region having the polypeptide sequence of SEQ ID NO:18;
- (k) a heavy chain variable region having the polypeptide sequence of SEQ ID NO:19, and a light chain variable region having the polypeptide sequence of SEQ ID NO:20;
- (l) a heavy chain variable region having the polypeptide sequence of SEQ ID NO:21, and a light chain variable region having the polypeptide sequence of SEQ ID NO:22;
- (m) a heavy chain variable region having the polypeptide sequence of SEQ ID NO:23, and a light chain variable region having the polypeptide sequence of SEQ ID NO:24;
- (n) a heavy chain variable region having the polypeptide sequence of SEQ ID NO:25, and a light chain variable region having the polypeptide sequence of SEQ ID NO:26;
- (o) a heavy chain variable region having the polypeptide sequence of SEQ ID NO:27, and a light chain variable region having the polypeptide sequence of SEQ ID NO:28;
- (p) a heavy chain variable region having the polypeptide sequence of SEQ ID NO:29, and a light chain variable region having the polypeptide sequence of SEQ ID NO:30;
- (q) a heavy chain variable region having the polypeptide sequence of SEQ ID NO:31, and a light chain variable region having the polypeptide sequence of SEQ ID NO:32;

(r) a heavy chain variable region having the polypeptide sequence of SEQ ID NO:35, and a light chain variable region having the polypeptide sequence of SEQ ID NO:36;

(s) a heavy chain variable region having the polypeptide sequence of SEQ ID NO:37, and a light chain variable region having the polypeptide sequence of SEQ ID NO:38; or (t) a heavy chain variable region having the polypeptide sequence of SEQ ID NO:39, and a light chain variable region having the polypeptide sequence of SEQ ID NO:40.

In certain embodiments, the isolated monoclonal antibody or antigen-binding fragment thereof inhibits the enzyme activity of soluble and/or cell-surface CD73.

In certain embodiments, the isolated monoclonal antibody or antigen-binding fragment thereof prevents the dimerization of CD73.

In certain embodiments, the isolated monoclonal antibody or antigen-binding fragment thereof induces the internalization of CD73.

In certain embodiments, the isolated monoclonal antibody or antigen-binding fragment thereof is chimeric.

In certain embodiments, the isolated monoclonal antibody or antigen-binding fragment thereof is human or humanized.

In certain embodiments, the humanized monoclonal antibody or antigen-binding fragment thereof comprises:

(1) a heavy chain variable region having the polypeptide sequence of SEQ ID NO:286, and a light chain variable region having the polypeptide sequence of SEQ ID NO:293;

(2) a heavy chain variable region having the polypeptide sequence of SEQ ID NO:282, and a light chain variable region having the polypeptide sequence of SEQ ID NO:290;

(3) a heavy chain variable region having the polypeptide sequence of SEQ ID NO:282, and a light chain variable region having the polypeptide sequence of SEQ ID NO:291;

(4) a heavy chain variable region having the polypeptide sequence of SEQ ID NO:282, and a light chain variable region having the polypeptide sequence of SEQ ID NO:292;

(5) a heavy chain variable region having the polypeptide sequence of SEQ ID NO:283, and a light chain variable region having the polypeptide sequence of SEQ ID NO:290;

(6) a heavy chain variable region having the polypeptide sequence of SEQ ID NO:283, and a light chain variable region having the polypeptide sequence of SEQ ID NO:291;

(7) a heavy chain variable region having the polypeptide sequence of SEQ ID NO:283, and a light chain variable region having the polypeptide sequence of SEQ ID NO:292;

(8) a heavy chain variable region having the polypeptide sequence of SEQ ID NO:284, and a light chain variable region having the polypeptide sequence of SEQ ID NO:290;

(9) a heavy chain variable region having the polypeptide sequence of SEQ ID NO:284, and a light chain variable region having the polypeptide sequence of SEQ ID NO:291;

(10) a heavy chain variable region having the polypeptide sequence of SEQ ID NO:284, and a light chain variable region having the polypeptide sequence of SEQ ID NO:292;

(11) a heavy chain variable region having the polypeptide sequence of SEQ ID NO:285, and a light chain variable region having the polypeptide sequence of SEQ ID NO:290;

(12) a heavy chain variable region having the polypeptide sequence of SEQ ID NO:285, and a light chain variable region having the polypeptide sequence of SEQ ID NO:291;

(13) a heavy chain variable region having the polypeptide sequence of SEQ ID NO:285, and a light chain variable region having the polypeptide sequence of SEQ ID NO:292;

(14) a heavy chain variable region having the polypeptide sequence of SEQ ID NO:283, and a light chain variable region having the polypeptide sequence of SEQ ID NO:293;

(15) a heavy chain variable region having the polypeptide sequence of SEQ ID NO:284, and a light chain variable region having the polypeptide sequence of SEQ ID NO:293;

(16) a heavy chain variable region having the polypeptide sequence of SEQ ID NO:285, and a light chain variable region having the polypeptide sequence of SEQ ID NO:293;

(17) a heavy chain variable region having the polypeptide sequence of SEQ ID NO:286, and a light chain variable region having the polypeptide sequence of SEQ ID NO:290;

(18) a heavy chain variable region having the polypeptide sequence of SEQ ID NO:286, and a light chain variable region having the polypeptide sequence of SEQ ID NO:291;

(19) a heavy chain variable region having the polypeptide sequence of SEQ ID NO:286, and a light chain variable region having the polypeptide sequence of SEQ ID NO:292;

(20) a heavy chain variable region having the polypeptide sequence of SEQ ID NO:287, and a light chain variable region having the polypeptide sequence of SEQ ID NO:294;

(21) a heavy chain variable region having the polypeptide sequence of SEQ ID NO:288, and a light chain variable region having the polypeptide sequence of SEQ ID NO:294;

(22) a heavy chain variable region having the polypeptide sequence of SEQ ID NO:289, and a light chain variable region having the polypeptide sequence of SEQ ID NO:294;

(23) a heavy chain variable region having the polypeptide sequence of SEQ ID NO:284, and a light chain variable region having the polypeptide sequence of SEQ ID NO:299;

(24) a heavy chain variable region having the polypeptide sequence of SEQ ID NO:295, and a light chain variable region having the polypeptide sequence of SEQ ID NO:299;

(25) a heavy chain variable region having the polypeptide sequence of SEQ ID NO:296, and a light chain variable region having the polypeptide sequence of SEQ ID NO:299;

(26) a heavy chain variable region having the polypeptide sequence of SEQ ID NO:297, and a light chain variable region having the polypeptide sequence of SEQ ID NO:299; or

(27) a heavy chain variable region having the polypeptide sequence of SEQ ID NO:298, and a light chain variable region having the polypeptide sequence of SEQ ID NO:299.

In certain embodiments, the isolated monoclonal antibody or antigen-binding fragment thereof is capable of activating T cells.

Also provided are isolated nucleic acids encoding the monoclonal antibodies or antigen-binding fragments thereof of the invention disclosed herein.

Also provided are vectors comprising the isolated nucleic acids encoding a monoclonal antibody or antigen-binding fragment thereof of the invention.

Also provided are host cells comprising the vectors comprising the isolated nucleic acids encoding a monoclonal antibody or antigen-binding fragment thereof of the invention.

In certain embodiments, provided is a pharmaceutical composition comprising the isolated monoclonal antibody or antigen-binding fragment thereof of the invention and a pharmaceutically acceptable carrier.

Also provided are methods of inhibiting the nucleotidase activity of CD73 in a subject in need thereof, comprising administering to the subject a pharmaceutical composition of the invention.

Also provided are methods of preventing the dimerization of CD73 in a subject in need thereof, comprising administering to the subject a pharmaceutical composition of the invention.

Also provided are methods of inducing the internalization of CD73 in a subject in need thereof, comprising administering to the subject a pharmaceutical composition of the invention.

Also provided are methods of treating cancer in a subject in need thereof, comprising administering to the subject a pharmaceutical composition of the invention. The cancer can be any liquid or solid cancer, for example, it can be selected from, but not limited to, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

Also provided are methods of producing the monoclonal antibody or antigen-binding fragment thereof of the invention, comprising culturing a cell comprising a nucleic acid encoding the monoclonal antibody or antigen-binding fragment thereof under conditions to produce the monoclonal antibody or antigen-binding fragment thereof, and recovering the antibody or antigen-binding fragment thereof from the cell or culture.

Also provided are methods of producing a pharmaceutical composition comprising the monoclonal antibody or antigen-binding fragment thereof of the invention, comprising combining the monoclonal antibody or antigen-binding fragment thereof with a pharmaceutically acceptable carrier to obtain the pharmaceutical composition.

Also provided are methods of determining a level of CD73 in a subject. The methods comprise (a) obtaining a sample from the subject; (b) contacting the sample with an antibody or antigen-binding fragment thereof of the invention; and (c) determining the level of CD73 in the subject.

In certain embodiments, the sample is a tissue sample. The tissue sample can, for example, be a cancer tissue sample. In certain embodiments, the sample is a blood sample.

Also provided are methods of determining the ecto-5'-nucleotidase activity of CD73 in a subject, wherein the enzyme activity can be fully inhibited by the monoclonal antibody or antigen-binding fragment thereof of the invention. The methods comprise (a) obtaining a sample from the subject; (b) contacting the sample with an antibody or antigen-binding fragment thereof of the invention; and (c) determining the ecto-5'-nucleotidase activity of CD73 in the subject. In certain embodiments, the sample is a tissue sample. The tissue sample can, for example, be a cancer tissue sample. In certain embodiments, the sample is a blood sample.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 4A shows the binding of humanized mAb 60A9-H5L4/IgG4 to human CD73 in an ELISA assay; chimeric mAb 60A9A/IgG4 was used as control. FIG. 4B shows the inhibition of the nucleotidase activity of soluble human CD73 by humanized mAb 60A9-H5L4/IgG4. No mAb, enzyme reaction with no mAb added; No CD73, enzyme reaction with no CD73 added. FIG. 4C shows the inhibition of the nucleotidase activity of human CD73 expressed on the surface of A375 cells by humanized mAb 60A9-H5L4/IgG4; chimeric mAb 60A9A/IgG4 was used as control. No mAb, enzyme reaction with no mAb added; No AMP, enzyme reaction with no AMP added; No Cells, enzyme reaction with no cells added. FIG. 4D shows the inhibition of the nucleotidase activity of human CD73 expressed on the surface of A375 cells by humanized mAbs 60A9-H3L5/IgG4, 60A9-H5L5/IgG4, 60A9-H6L5/IgG4, 60A9-H7L5/IgG4, 60A9-H8L5/IgG4 and 60A9-H9L5/IgG4; chimeric mAb 60A9A/IgG4 was used as control. No mAb, enzyme reaction with no mAb added; No AMP, enzyme reaction with no AMP added; No cells, enzyme reaction with no cells added.

DETAILED DESCRIPTION OF THE INVENTION

Figure 1A:
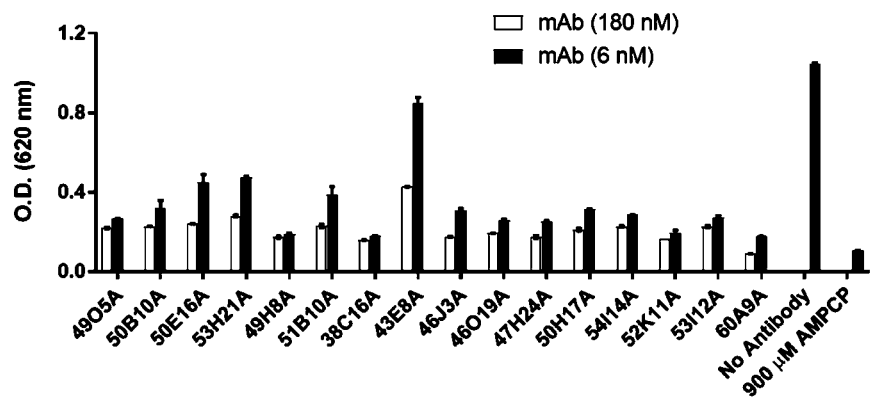
FIGS. 1A and 1B show the inhibition of the nucleotidase activity of human CD73 immobilized on a plate by chimeric anti-CD73 mAbs. No Antibody, enzyme reaction with no antibody added; AMPCP (adenosine 5' ($\alpha$, $\beta$-methylene) diphosphate) was used as a control for inhibition of enzyme activity.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "consists of," or variations such as "consist of" or "consisting of," as used throughout the specification and claims, indicate the inclusion of any recited integer or group of integers, but that no additional integer or group of integers can be added to the specified method, structure, or composition.

As used herein, the term "consists essentially of," or variations such as "consist essentially of" or "consisting essentially of," as used throughout the specification and claims, indicate the inclusion of any recited integer or group of integers, and the optional inclusion of any recited integer or group of integers that do not materially change the basic or novel properties of the specified method, structure or composition. See M.P.E.P. § 2111.03.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The words "right," "left," "lower," and "upper" designate directions in the drawings to which reference is made.

It should also be understood that the terms "about," "approximately," "generally," "substantially," and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., anti-CD73 antibodies and polynucleotides that encode them, CD73 polypeptides and CD73 polynucleotides that encode them), refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased.

Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions.

As used herein, the terms "inhibit," "inhibiting," and "inhibition," mean to decrease an activity, response, condition, disease or other biological parameter. This can include, but is not limited to, complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between, as compared to native or control levels. By way of a non-limiting example, an antibody of the invention can inhibit the nucleotidase activity of a CD73 protein. The activity of the CD73 protein can be reduced or ablated relative to the native CD73 protein activity. By way of another non-limiting example, an antibody of the invention can inhibit or prevent the dimerization of a CD73 protein in a subject. The dimerization of CD73 can be reduced or ablated relative to the native CD73 dimerization.

Antibodies

The invention generally relates to isolated anti-CD73 antibodies, nucleic acids and expression vectors encoding the antibodies, recombinant cells containing the vectors, and compositions comprising the antibodies. The invention also generally relates to methods of making the antibodies and methods of using the antibodies to treat diseases, including cancer. The antibodies of the invention possess one or more desirable functional properties, including but not limited to, high-affinity binding to CD73, high specificity to CD73, the ability to inhibit the nucleotidase activity of CD73, the ability to prevent the dimerization of CD73, the ability to induce the internalization of CD73 into cells, which results in a decrease in the cell surface content of CD73, and the ability to inhibit tumor growth in subjects in need thereof and in animal models when administered alone or in combination with other anti-cancer therapies.

In a general aspect, the invention relates to isolated monoclonal antibodies or antigen-binding fragments thereof that specifically bind CD73.

As used herein, the term "antibody" is used in a broad sense and includes immunoglobulin or antibody molecules including human, humanized, composite and chimeric antibodies and antibody fragments that are monoclonal or polyclonal. In general, antibodies are proteins or peptide chains that exhibit binding specificity to a specific antigen. Antibody structures are well known. Immunoglobulins can be assigned to five major classes (i.e., IgA, IgD, IgE, IgG and IgM), depending on the heavy chain constant domain amino acid sequence. IgA and IgG are further sub-classified as the isotypes IgA1, IgA2, IgG1, IgG2, IgG3 and IgG4. Accordingly, the antibodies of the invention can be of any of the five major classes or corresponding sub-classes. Preferably, the antibodies of the invention are IgG1, IgG2, IgG3 or IgG4. Antibody light chains of vertebrate species can be assigned to one of two clearly distinct types, namely kappa and lambda, based on the amino acid sequences of their constant domains. Accordingly, the antibodies of the invention can contain a kappa or lambda light chain constant domain. According to particular embodiments, the antibodies of the invention include heavy and/or light chain constant regions from rat or human antibodies. In addition to the heavy and light constant domains, antibodies contain an antigen-binding region that is made up of a light chain variable region and a heavy chain variable region, each of which contains three domains (i.e., complementarity determining regions 1-3; CDR1, CDR2, and CDR3). The light chain variable region domains are alternatively referred to as LCDR1, LCDR2, and LCDR3, and the heavy chain variable region domains are alternatively referred to as HCDR1, HCDR2, and HCDR3.

As used herein, the term an "isolated antibody" refers to an antibody which is substantially free of other antibodies having different antigenic specificities (e.g., an isolated antibody that specifically binds to CD73 is substantially free of antibodies that do not bind to CD73). In addition, an isolated antibody is substantially free of other cellular material and/or chemicals.

As used herein, the term "monoclonal antibody" refers to an antibody obtained from a population of substantially homogeneous antibodies, i.e., the individual antibodies comprising the population are identical except for possible naturally occurring mutations that may be present in minor amounts. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

As used herein, the term "antigen-binding fragment" refers to an antibody fragment such as, for example, a diabody, a Fab, a Fab', a F(ab')2, an Fv fragment, a disulfide stabilized Fv fragment (dsFv), a $(dsFv)_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment of the heavy chain. According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

As used herein, the term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide.

As used herein, the term "humanized antibody" refers to a non-human antibody that is modified to increase the sequence homology to that of a human antibody, such that the antigen-binding properties of the antibody are retained, but its antigenicity in the human body is reduced.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., different proteins (or different subunits of a multimeric protein). In an embodiment, a multispecific antibody comprises a third, fourth, or fifth immunoglobulin variable domain. In an embodiment, a multispecific antibody is a bispecific antibody molecule, a trispecific antibody molecule, or a tetraspecific antibody molecule.

As used herein, the term "bispecifc antibody" refers to a multispecific antibody that binds no more than two epitopes or two antigens. A bispecific antibody is characterized by a first immunoglobulin variable domain sequence which has binding specificity for a first epitope and a second immunoglobulin variable domain sequence that has binding specificity for a second epitope. In an embodiment, the first and second epitopes are on the same antigen, e.g., the same protein (or subunit of a multimeric protein). In an embodiment, the first and second epitopes overlap or substantially overlap. In an embodiment, the first and second epitopes are on different antigens, e.g., different proteins (or different subunits of a multimeric protein). In an embodiment, a bispecific antibody comprises a heavy chain variable domain sequence and a light chain variable domain sequence which have binding specificity for a first epitope and a heavy chain variable domain sequence and a light chain variable domain sequence which have binding specificity for a second epitope. In an embodiment, a bispecific antibody comprises a half antibody, or fragment thereof, having binding specificity for a first epitope and a half antibody, or fragment thereof, having binding specificity for a second epitope. In an embodiment, a bispecific antibody comprises a scFv, or fragment thereof, having binding specificity for a first epitope, and a scFv, or fragment thereof, having binding specificity for a second epitope. In an embodiment, the first epitope is located on CD73 and the second epitope is located on PD-1, PD-L1, TIM-3, LAG-3, CD47, CD3, apelin, claudin18.2, DLL3, folate receptor alpha (FRα), TIP-1, CTLA-4, EGFR, HER-2, CD19, CD20, CD33 and/or other tumor associated immune suppressors or surface antigens.

As used herein, the term "CD73" refers to the ecto-5'-nucleotidase (ecto-5'-NT or EC 3.1.3.5), a cell surface phosphatase that catalyzes the dephosphorylation of extracellular AMP to produce adenosine. Physiologically, CD73 is induced by hypoxia to control inflammation at injury sites (Bours et al., Pharmacol Ther 2006; 112:358-404). Pathologically, CD73 is often found overexpressed on regulatory T cells (Tregs) and tumor cells (Paul et al., Trends Immunol 2012; 33:231-237). The elevated CD73 activity leads to the accumulation of adenosine in the tumor microenvironment (TME). Through binding to adenosine receptors A2a and A2b, adenosine suppresses both innate and adaptive immunities by regulating many immune cells such as macrophages (Csoka et al., FASEB J 2012; 26:376-386), dendritic cells (Panther et al., Blood 2003; 101:3985-3990), natural killer cells (Hausler et al., Cancer Immunol Immunother 2011; 60:1405-1418), and T effector cells (Hoskin et al., Int J Oncol 2008; 32:527-535). Therefore, it has been postulated that immune suppression by adenosine may be alleviated by inhibiting the activity of CD73 in the TME. Indeed, in vivo animal studies (Jin et al., Cancer Res 2010; 70:2245-2255; Stagg et al., Cancer Res 2011; 71:2890-2900) indicate that inhibiting the activity of CD73 inhibits tumor formation and growth, suggesting that CD73 is a promising target for cancer therapy. The term "human CD73" refers to a CD73 originated from a human. An exemplary amino acid sequence of a human CD73 is represented in GenBank Accession No. P21589.1 (SEQ ID NO:281).

As used herein, an antibody that "specifically binds to CD73" refers to an antibody that binds to a CD73, preferably a human CD73, with a KD of $1 \times 10^{-7}$M or less, preferably $1 \times 10^{-8}$M or less, more preferably $5 \times 10^{-9}$ M or less, $1 \times 10^{-9}$M or less, $5 \times 10^{-10}$ M or less, or $1 \times 10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a Biacore® system, or by using bio-layer interferometry technology, such as an Octet RED96 system.

The smaller the value of the KD of an antibody, the higher affinity that the antibody binds to a target antigen.

According to a particular aspect, the invention relates to an isolated monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:

(1) SEQ ID NOs:89, 90, 91, 149, 150 and 151, respectively;
(2) SEQ ID NOs:41, 42, 43, 101, 102 and 103, respectively;
(3) SEQ ID NOs:44, 45, 46, 104, 105 and 106, respectively;
(4) SEQ ID NOs:47, 48, 49, 107, 108 and 109, respectively;
(5) SEQ ID NOs:50, 51, 52, 110, 111 and 112, respectively;
(6) SEQ ID NOs:53, 54, 55, 113, 114 and 115, respectively;
(7) SEQ ID NOs:56, 57, 58, 116, 117 and 118, respectively;
(8) SEQ ID NOs:59, 60, 61, 119, 120 and 121, respectively;
(9) SEQ ID NOs:62, 63, 64, 122, 123 and 124, respectively;
(10) SEQ ID NOs:65, 66, 67, 125, 126 and 127, respectively;
(11) SEQ ID NOs:68, 69, 70, 128, 129 and 130, respectively;
(12) SEQ ID NOs:71, 72, 73, 131, 132 and 133, respectively;
(13) SEQ ID NOs:74, 75, 76, 134, 135 and 136, respectively;
(14) SEQ ID NOs:77, 78, 79, 137, 138 and 139, respectively;
(15) SEQ ID NOs:80, 81, 82, 140, 141 and 142, respectively;
(16) SEQ ID NOs:83, 84, 85, 143, 144 and 145, respectively;
(17) SEQ ID NOs:86, 87, 88, 146, 147 and 148, respectively;
(18) SEQ ID NOs:92, 93, 94, 152, 153 and 154, respectively;
(19) SEQ ID NOs:95, 96, 97, 155, 156 and 157, respectively; or
(20) SEQ ID NOs:98, 99, 100, 158, 159 and 160, respectively;
wherein the antibody or antigen-binding fragment thereof specifically binds to CD73, preferably human CD73.

According to a particular aspect, the invention relates to an isolated monoclonal antibody or antigen-binding fragment thereof comprising a heavy chain complementarity determining region 1 (HCDR1), a HCDR2, a HCDR3, a light chain complementarity determining region 1 (LCDR1), a LCDR2, and a LCDR3, having the polypeptide sequences of:

(1) SEQ ID NOs:209, 210, 211, 269, 270 and 271, respectively;
(2) SEQ ID NOs:161, 162, 163, 221, 222 and 223, respectively;
(3) SEQ ID NOs:164, 165, 166, 224, 225 and 226, respectively;
(4) SEQ ID NOs:167, 168, 169, 227, 228 and 229, respectively;
(5) SEQ ID NOs:170, 171, 172, 230, 231 and 232, respectively;
(6) SEQ ID NOs:173, 174, 175, 233, 234 and 235, respectively;
(7) SEQ ID NOs:176, 177, 178, 236, 237 and 238, respectively;
(8) SEQ ID NOs:179, 180, 181, 239, 240 and 241, respectively;
(9) SEQ ID NOs:182, 183, 184, 242, 243 and 244, respectively;
(10) SEQ ID NOs:185, 186, 187, 245, 246 and 247, respectively;
(11) SEQ ID NOs:188, 189, 190, 248, 249 and 250, respectively;
(12) SEQ ID NOs:191, 192, 193, 251, 252 and 253, respectively;
(13) SEQ ID NOs:194, 195, 196, 254, 255 and 256, respectively;
(14) SEQ ID NOs:197, 198, 199, 257, 258 and 259, respectively;
(15) SEQ ID NOs:200, 201, 202, 260, 261 and 262, respectively;
(16) SEQ ID NOs:203, 204, 205, 263, 264 and 265, respectively;
(17) SEQ ID NOs:206, 207, 208, 266, 267 and 268, respectively;
(18) SEQ ID NOs:212, 213, 214, 272, 273 and 274, respectively;
(19) SEQ ID NOs:215, 216, 217, 275, 276 and 277, respectively; or
(20) SEQ ID NOs:218, 219, 220, 278, 279 and 280, respectively;
wherein the antibody or antigen-binding fragment thereof specifically binds to CD73, preferably human CD73.

According to another particular aspect, the invention relates to an isolated monoclonal antibody or antigen-binding fragment thereof comprising a heavy chain variable region having a polypeptide sequence at least 85%, preferably 90%, more preferably 95% or more, such as 95%, 96%, 97%, 98%, or 99% identical to one of SEQ ID NOs:33, 1, 3, 5, 7, 9, 11, 13, 15, 17, 19, 21, 23, 25, 27, 29, 31, 35, 37 or 39, or a light chain variable region having a polypeptide sequence at least 85%, preferably 90%, more preferably 95% or more, such as 95%, 96%, 97%, 98%, or 99% identical to one of SEQ ID NOs:34, 2, 4, 6, 8, 10, 12, 14, 16, 18, 20, 22, 24, 26, 28, 30, 32, 36, 38 or 40. According to one preferred embodiment, the isolated monoclonal antibody or antigen-binding fragment thereof of the invention comprises a heavy chain variable region having the polypeptide sequence at least 85%, preferably 90%, more preferably 95% or more, such as 95%, 96%, 97%, 98%, or 99% identical to SEQ ID NO:33, 1, 3, 5, 7, 9, 11, 13, 15, 17, 19, 21, 23, 25, 27, 29, 31, 35, 37 or 39, and a light chain variable region having a polypeptide sequence at least 85%, preferably 90%, more preferably 95% or more, such as 95%, 96%, 97%, 98%, or 99% identical to SEQ ID NO:34, 2, 4, 6, 8, 10, 12, 14, 16, 18, 20, 22, 24, 26, 28, 30, 32, 36, 38 or 40, respectively.

According to another particular aspect, the invention relates to an isolated monoclonal antibody or antigen-binding fragment thereof of the invention, comprising:

(1) a heavy chain variable region having the polypeptide sequence of SEQ ID NO:33, and a light chain variable region having the polypeptide sequence of SEQ ID NO:34;
(2) a heavy chain variable region having the polypeptide sequence of SEQ ID NO:1, and a light chain variable region having the polypeptide sequence of SEQ ID NO:2;
(3) a heavy chain variable region having the polypeptide sequence of SEQ ID NO:3, and a light chain variable region having the polypeptide sequence of SEQ ID NO:4;
(4) a heavy chain variable region having the polypeptide sequence of SEQ ID NO:5, and a light chain variable region having the polypeptide sequence of SEQ ID NO:6;
(5) a heavy chain variable region having the polypeptide sequence of SEQ ID NO:7, and a light chain variable region having the polypeptide sequence of SEQ ID NO:8;
(6) a heavy chain variable region having the polypeptide sequence of SEQ ID NO:9, and a light chain variable region having the polypeptide sequence of SEQ ID NO:10;
(7) a heavy chain variable region having the polypeptide sequence of SEQ ID NO:11, and a light chain variable region having the polypeptide sequence of SEQ ID NO:12;
(8) a heavy chain variable region having the polypeptide sequence of SEQ ID NO:13, and a light chain variable region having the polypeptide sequence of SEQ ID NO:14;
(9) a heavy chain variable region having the polypeptide sequence of SEQ ID NO:15, and a light chain variable region having the polypeptide sequence of SEQ ID NO:16;
(10) a heavy chain variable region having the polypeptide sequence of SEQ ID NO:17, and a light chain variable region having the polypeptide sequence of SEQ ID NO:18;
(11) a heavy chain variable region having the polypeptide sequence of SEQ ID NO:19, and a light chain variable region having the polypeptide sequence of SEQ ID NO:20;
(12) a heavy chain variable region having the polypeptide sequence of SEQ ID NO:21, and a light chain variable region having the polypeptide sequence of SEQ ID NO:22;
(13) a heavy chain variable region having the polypeptide sequence of SEQ ID NO:23, and a light chain variable region having the polypeptide sequence of SEQ ID NO:24;
(14) a heavy chain variable region having the polypeptide sequence of SEQ ID NO:25, and a light chain variable region having the polypeptide sequence of SEQ ID NO:26;
(15) a heavy chain variable region having the polypeptide sequence of SEQ ID NO:27, and a light chain variable region having the polypeptide sequence of SEQ ID NO:28;
(16) a heavy chain variable region having the polypeptide sequence of SEQ ID NO:29, and a light chain variable region having the polypeptide sequence of SEQ ID NO:30;
(17) a heavy chain variable region having the polypeptide sequence of SEQ ID NO:31, and a light chain variable region having the polypeptide sequence of SEQ ID NO:32;
(18) a heavy chain variable region having the polypeptide sequence of SEQ ID NO:35, and a light chain variable region having the polypeptide sequence of SEQ ID NO:36;
(19) a heavy chain variable region having the polypeptide sequence of SEQ ID NO:37, and a light chain variable region having the polypeptide sequence of SEQ ID NO:38; or
(20) a heavy chain variable region having the polypeptide sequence of SEQ ID NO:39, and a light chain variable region having the polypeptide sequence of SEQ ID NO:40.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 41, 42, 43, 101, 102 and 103, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 44, 45, 46, 104, 105 and 106, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:3, and a light chain variable region having a polypeptide sequence at least 85%, preferably 90%, more preferably 95% or more, such as 95%, 96%, 97%, 98%, or 99% identical to SEQ ID NO:4. Preferably, the isolated monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 47, 48, 49, 107, 108 and 109, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:5, and a light chain variable region having a polypeptide sequence at least 85%, preferably 90%, more preferably 95% or more, such as 95%, 96%, 97%, 98%, or 99% identical to SEQ ID NO:6. Preferably, the isolated monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 50, 51, 52, 110, 111 and 112, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:7, and a light chain variable region having a polypeptide sequence at least 85%, preferably 90%, more preferably 95% or more, such as 95%, 96%, 97%, 98%, or 99% identical to SEQ ID NO:8. Preferably, the isolated monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 53, 54, 55, 113, 114 and 115, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:9, and a light chain variable region having a polypeptide sequence at least 85%, preferably 90%, more preferably 95% or more, such as 95%, 96%, 97%, 98%, or 99% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 56, 57, 58, 116, 117 and 118, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:11, and a light chain variable region having a polypeptide sequence at least 85%, preferably 90%, more preferably 95% or more, such as 95%, 96%, 97%, 98%, or 99% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 59, 60, 61, 119, 120 and 121, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:13, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 62, 63, 64, 122, 123 and 124, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:15, and a light chain variable region having a polypeptide sequence at least 85%, preferably 90%, more preferably 95% or more, such as 95%, 96%, 97%, 98%, or 99% identical to SEQ ID NO:16. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 65, 66, 67, 125, 126 and 127, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:17, and a light chain variable region having a polypeptide sequence at least 85%, preferably 90%, more preferably 95% or more, such as 95%, 96%, 97%, 98%, or 99% identical to SEQ ID NO:18. Preferably, the isolated monoclonal antibody or antigen-binding fragment thereof comprises a heavy chain variable region having the polypeptide sequence of SEQ ID NO:17; and a light chain variable region having the polypeptide sequence of SEQ ID NO:18.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 68, 69, 70, 128, 129 and 130, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:19, and a light chain variable region having a polypeptide sequence at least 85%, preferably 90%, more preferably 95% or more, such as 95%, 96%, 97%, 98%, or 99% identical to SEQ ID NO:20. Preferably, the isolated monoclonal antibody or antigen-binding fragment thereof comprises a heavy chain variable region having the polypeptide sequence of SEQ ID NO:19; and a light chain variable region having the polypeptide sequence of SEQ ID NO:20.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 71, 72, 73, 131, 132 and 133, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:21, and a light chain variable region having a polypeptide sequence at least 85%, preferably 90%, more preferably 95% or more, such as 95%, 96%, 97%, 98%, or 99% identical to SEQ ID NO:22. Preferably, the isolated monoclonal antibody or antigen-binding fragment thereof comprises a heavy chain variable region having the polypeptide sequence of SEQ ID NO:21; and a light chain variable region having the polypeptide sequence of SEQ ID NO:22.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 74, 75, 76, 134, 135 and 136, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:23, and a light chain variable region having a polypeptide sequence at least 85%, preferably 90%, more preferably 95% or more, such as 95%, 96%, 97%, 98%, or 99% identical to SEQ ID NO:24. Preferably, the isolated monoclonal antibody or antigen-binding fragment thereof comprises a heavy chain variable region having the polypeptide sequence of SEQ ID NO:23; and a light chain variable region having the polypeptide sequence of SEQ ID NO:24.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 77, 78, 79, 137, 138 and 139, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:25, and a light chain variable region having a polypeptide sequence at least 85%, preferably 90%, more preferably 95% or more, such as 95%, 96%, 97%, 98%, or 99% identical to SEQ ID NO:26. Preferably, the isolated monoclonal antibody or antigen-binding fragment thereof comprises a heavy chain variable region having the polypeptide sequence of SEQ ID NO:25; and a light chain variable region having the polypeptide sequence of SEQ ID NO:26.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 80, 81, 82, 140, 141 and 142, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:27, and a light chain variable region having a polypeptide sequence at least 85%, preferably 90%, more preferably 95% or more, such as 95%, 96%, 97%, 98%, or 99% identical to SEQ ID NO:28. Preferably, the isolated monoclonal antibody or antigen-binding fragment thereof comprises a heavy chain variable region having the polypeptide sequence of SEQ ID NO:27; and a light chain variable region having the polypeptide sequence of SEQ ID NO:28.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 83, 84, 85, 143, 144 and 145, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:29, and a light chain variable region having a polypeptide sequence at least 85%, preferably 90%, more preferably 95% or more, such as 95%, 96%, 97%, 98%, or 99% identical to SEQ ID NO:30. Preferably, the isolated monoclonal antibody or antigen-binding fragment thereof comprises a heavy chain variable region having the polypeptide sequence of SEQ ID NO:29; and a light chain variable region having the polypeptide sequence of SEQ ID NO:30.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 86, 87, 88, 146, 147 and 148, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:31, and a light chain variable region having a polypeptide sequence at least 85%, preferably 90%, more preferably 95% or more, such as 95%, 96%, 97%, 98%, or 99% identical to SEQ ID NO:32. Preferably, the isolated monoclonal antibody or antigen-binding fragment thereof comprises a heavy chain variable region having the polypeptide sequence of SEQ ID NO:31; and a light chain variable region having the polypeptide sequence of SEQ ID NO:32.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 89, 90, 91, 149, 150 and 151, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:33, and a light chain variable region having a polypeptide sequence at least 85%, preferably 90%, more preferably 95% or more, such as 95%, 96%, 97%, 98%, or 99% identical to SEQ ID NO:34. Preferably, the isolated monoclonal antibody or antigen-binding fragment thereof comprises a heavy chain variable region having the polypeptide sequence of SEQ ID NO:33; and a light chain variable region having the polypeptide sequence of SEQ ID NO:34.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 92, 93, 94, 152, 153 and 154, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:35, and a light chain variable region having a polypeptide sequence at least 85%, preferably 90%, more preferably 95% or more, such as 95%, 96%, 97%, 98%, or 99% identical to SEQ ID NO:36. Preferably, the isolated monoclonal antibody or antigen-binding fragment thereof comprises a heavy chain variable region having the polypeptide sequence of SEQ ID NO:35; and a light chain variable region having the polypeptide sequence of SEQ ID NO:36.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 95, 96, 97, 155, 156 and 157, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:37, and a light chain variable region having a polypeptide sequence at least 85%, preferably 90%, more preferably 95% or more, such as 95%, 96%, 97%, 98%, or 99% identical to SEQ ID NO:38. Preferably, the isolated monoclonal antibody or antigen-binding fragment thereof comprises a heavy chain variable region having the polypeptide sequence of SEQ ID NO:37; and a light chain variable region having the polypeptide sequence of SEQ ID NO:38.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 98, 99, 100, 158, 159 and 160, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:39, and a light chain variable region having a polypeptide sequence at least 85%, preferably 90%, more preferably 95% or more, such as 95%, 96%, 97%, 98%, or 99% identical to SEQ ID NO:40. Preferably, the isolated monoclonal antibody or antigen-binding fragment thereof comprises a heavy chain variable region having the polypeptide sequence of SEQ ID NO:39; and a light chain variable region having the polypeptide sequence of SEQ ID NO:40.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 161, 162, 163, 221, 222 and 223, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:1, and a light chain variable region having a polypeptide sequence at least 85%, preferably 90%, more preferably 95% or more, such as 95%, 96%, 97%, 98%, or 99% identical to SEQ ID NO:2. Preferably, the isolated monoclonal antibody or antigen-binding fragment thereof comprises a heavy chain variable region having the polypeptide sequence of SEQ ID NO:1; and a light chain variable region having the polypeptide sequence of SEQ ID NO:2.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 164, 165, 166, 224, 225 and 226, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:3, and a light chain variable region having a polypeptide sequence at least 85%, preferably 90%, more preferably 95% or more, such as 95%, 96%, 97%, 98%, or 99% identical to SEQ ID NO:4. Preferably, the isolated monoclonal antibody or antigen-binding fragment thereof comprises a heavy chain variable region having the polypeptide sequence of SEQ ID NO:3; and a light chain variable region having the polypeptide sequence of SEQ ID NO:4.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 167, 168, 169, 227, 228 and 229, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:5, and a light chain variable region having a polypeptide sequence at least 85%, preferably 90%, more preferably 95% or more, such as 95%, 96%, 97%, 98%, or 99% identical to SEQ ID NO:6. Preferably, the isolated monoclonal antibody or antigen-binding fragment thereof comprises a heavy chain variable region having the polypeptide sequence of SEQ ID NO:5; and a light chain variable region having the polypeptide sequence of SEQ ID NO:6.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 170, 171, 172, 230, 231 and 232, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:7, and a light chain variable region having a polypeptide sequence at least 85%, preferably 90%, more preferably 95% or more, such as 95%, 96%, 97%, 98%, or 99% identical to SEQ ID NO:8. Preferably, the isolated monoclonal antibody or antigen-binding fragment thereof comprises a heavy chain variable region having the polypeptide sequence of SEQ ID NO:7; and a light chain variable region having the polypeptide sequence of SEQ ID NO:8.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 173, 174, 175, 233, 234 and 235, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:9, and a light chain variable region having a polypeptide sequence at least 85%, preferably 90%, more preferably 95% or more, such as 95%, 96%, 97%, 98%, or 99% identical to SEQ ID NO:10. Preferably, the isolated monoclonal antibody or antigen-binding fragment thereof comprises a heavy chain variable region having the polypeptide sequence of SEQ ID NO:9; and a light chain variable region having the polypeptide sequence of SEQ ID NO:10.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 176, 177, 178, 236, 237 and 238, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:11, and a light chain variable region having a polypeptide sequence at least 85%, preferably 90%, more preferably 95% or more, such as 95%, 96%, 97%, 98%, or 99% identical to SEQ ID NO:12. Preferably, the isolated monoclonal antibody or antigen-binding fragment thereof comprises a heavy chain variable region having the polypeptide sequence of SEQ ID NO:11; and a light chain variable region having the polypeptide sequence of SEQ ID NO:12.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 179, 180, 181, 239, 240 and 241, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:13, and a light chain variable region having a polypeptide sequence at least 85%, preferably 90%, more preferably 95% or more, such as 95%, 96%, 97%, 98%, or 99% identical to SEQ ID NO:14. Preferably, the isolated monoclonal antibody or antigen-binding fragment thereof comprises a heavy chain variable region having the polypeptide sequence of SEQ ID NO:13; and a light chain variable region having the polypeptide sequence of SEQ ID NO:14.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 182, 183, 184, 242, 243 and 244, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:15, and a light chain variable region having a polypeptide sequence at least 85%, preferably 90%, more preferably 95% or more, such as 95%, 96%, 97%, 98%, or 99% identical to SEQ ID NO:16. Preferably, the isolated monoclonal antibody or antigen-binding fragment thereof comprises a heavy chain variable region having the polypeptide sequence of SEQ ID NO:15; and a light chain variable region having the polypeptide sequence of SEQ ID NO:16.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 185, 186, 187, 245, 246 and 247, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:17, and a light chain variable region having a polypeptide sequence at least 85%, preferably 90%, more preferably 95% or more, such as 95%, 96%, 97%, 98%, or 99% identical to SEQ ID NO:18. Preferably, the isolated monoclonal antibody or antigen-binding fragment thereof comprises a heavy chain variable region having the polypeptide sequence of SEQ ID NO:17; and a light chain variable region having the polypeptide sequence of SEQ ID NO:18.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 188, 189, 190, 248, 249 and 250, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:19, and a light chain variable region having a polypeptide sequence at least 85%, preferably 90%, more preferably 95% or more, such as 95%, 96%, 97%, 98%, or 99% identical to SEQ ID NO:20. Preferably, the isolated monoclonal antibody or antigen-binding fragment thereof comprises a heavy chain variable region having the polypeptide sequence of SEQ ID NO:19; and a light chain variable region having the polypeptide sequence of SEQ ID NO:20.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 191, 192, 193, 251, 252 and 253, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:21, and a light chain variable region having a polypeptide sequence at least 85%, preferably 90%, more preferably 95% or more, such as 95%, 96%, 97%, 98%, or 99% identical to SEQ ID NO:22. Preferably, the isolated monoclonal antibody or antigen-binding fragment thereof comprises a heavy chain variable region having the polypeptide sequence of SEQ ID NO:21; and a light chain variable region having the polypeptide sequence of SEQ ID NO:22.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 194, 195, 196, 254, 255 and 256, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:23, and a light chain variable region having a polypeptide sequence at least 85%, preferably 90%, more preferably 95% or more, such as 95%, 96%, 97%, 98%, or 99% identical to SEQ ID NO:24. Preferably, the isolated monoclonal antibody or antigen-binding fragment thereof comprises a heavy chain variable region having the polypeptide sequence of SEQ ID NO:23; and a light chain variable region having the polypeptide sequence of SEQ ID NO:24.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 197, 198, 199, 257, 258 and 259, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:25, and a light chain variable region having a polypeptide sequence at least 85%, preferably 90%, more preferably 95% or more, such as 95%, 96%, 97%, 98%, or 99% identical to SEQ ID NO:26. Preferably, the isolated monoclonal antibody or antigen-binding fragment thereof comprises a heavy chain variable region having the polypeptide sequence of SEQ ID NO:25; and a light chain variable region having the polypeptide sequence of SEQ ID NO:26.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 200, 201, 202, 260, 261 and 262, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:27, and a light chain variable region having a polypeptide sequence at least 85%, preferably 90%, more preferably 95% or more, such as 95%, 96%, 97%, 98%, or 99% identical to SEQ ID NO:28. Preferably, the isolated monoclonal antibody or antigen-binding fragment thereof comprises a heavy chain variable region having the polypeptide sequence of SEQ ID NO:27; and a light chain variable region having the polypeptide sequence of SEQ ID NO:28.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 203, 204, 205, 263, 264 and 265, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:29, and a light chain variable region having a polypeptide sequence at least 85%, preferably 90%, more preferably 95% or more, such as 95%, 96%, 97%, 98%, or 99% identical to SEQ ID NO:30. Preferably, the isolated monoclonal antibody or antigen-binding fragment thereof comprises a heavy chain variable region having the polypeptide sequence of SEQ ID NO:29; and a light chain variable region having the polypeptide sequence of SEQ ID NO:30.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 206, 207, 208, 266, 267 and 268, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:31, and a light chain variable region having a polypeptide sequence at least 85%, preferably 90%, more preferably 95% or more, such as 95%, 96%, 97%, 98%, or 99% identical to SEQ ID NO:32. Preferably, the isolated monoclonal antibody or antigen-binding fragment thereof comprises a heavy chain variable region having the polypeptide sequence of SEQ ID NO:31; and a light chain variable region having the polypeptide sequence of SEQ ID NO:32.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 209, 210, 211, 269, 270 and 271, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:33, and a light chain variable region having a polypeptide sequence at least 85%, preferably 90%, more preferably 95% or more, such as 95%, 96%, 97%, 98%, or 99% identical to SEQ ID NO:34. Preferably, the isolated monoclonal antibody or antigen-binding fragment thereof comprises a heavy chain variable region having the polypeptide sequence of SEQ ID NO:33; and a light chain variable region having the polypeptide sequence of SEQ ID NO:34.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 212, 213, 214, 272, 273 and 274, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:35, and a light chain variable region having a polypeptide sequence at least 85%, preferably 90%, more preferably 95% or more, such as 95%, 96%, 97%, 98%, or 99% identical to SEQ ID NO:36. Preferably, the isolated monoclonal antibody or antigen-binding fragment thereof comprises a heavy chain variable region having the polypeptide sequence of SEQ ID NO:35; and a light chain variable region having the polypeptide sequence of SEQ ID NO:36.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 215, 216, 217, 275, 276 and 277, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:37, and a light chain variable region having a polypeptide sequence at least 85%, preferably 90%, more preferably 95% or more, such as 95%, 96%, 97%, 98%, or 99% identical to SEQ ID NO:38. Preferably, the isolated monoclonal antibody or antigen-binding fragment thereof comprises a heavy chain variable region having the polypeptide sequence of SEQ ID NO:37; and a light chain variable region having the polypeptide sequence of SEQ ID NO:38.

In one embodiment, the invention relates to an isolated monoclonal antibody or antigen-binding fragment thereof, comprising HCDR1, HCDR2, HCDR3, LCDR1, LCDR2 and LCDR3, having the polypeptide sequences of SEQ ID NOs: 218, 219, 220, 278, 279 and 280, respectively. In another embodiment, the isolated monoclonal antibody or antigen-binding fragment thereof comprises a heavy chain variable region having a polypeptide sequence at least 85%, preferably 90%, more preferably 95% or more, such as 95%, 96%, 97%, 98%, or 99% identical to SEQ ID NO:39, and a light chain variable region having a polypeptide sequence at least 85%, preferably 90%, more preferably 95% or more, such as 95%, 96%, 97%, 98%, or 99% identical to SEQ ID NO:40. Preferably, the isolated monoclonal antibody or antigen-binding fragment thereof comprises a heavy chain variable region having the polypeptide sequence of SEQ ID NO:39; and a light chain variable region having the polypeptide sequence of SEQ ID NO:40.

According to another particular aspect, the invention relates to an isolated monoclonal antibody or antigen-binding fragment thereof of the invention, wherein the antibody or antigen-binding fragment thereof inhibits the enzyme activity of soluble and/or cell surface CD73. CD73 is a glycophosphatidylinositol (GPI)-anchored protein on the cell surface; it can also be shed to yield a catalytically active form in solution (Arias et al., J Cell Biol. 1997; 136(2):421-31). Here, the cell surface CD73 refers to the CD73 on the cell surface anchored by GPI; the soluble CD73 refers to those that are shed from the cell surface and catalytically active in the solution.

According to another particular aspect, the invention relates to an isolated monoclonal antibody or antigen-binding fragment thereof of the invention, wherein the antibody or antigen-binding fragment thereof prevents the dimerization of CD73. As used herein, "dimerization" refers to the formation of a CD73 dimer by two subunits. Preventing dimerization of CD73 refers to blocking or inhibiting the formation of a CD73 dimer.

According to another particular aspect, the invention relates to an isolated monoclonal antibody or antigen-binding fragment thereof of the invention, wherein the antibody or antigen-binding fragment thereof induces the internalization of CD73. As used herein, "internalization of CD73" refers to the movement of a CD73 protein from the surface of a cell to the inside areas of the cell.

According to another particular aspect, the invention relates to an isolated monoclonal antibody or antigen-binding fragment thereof of the invention, wherein the antibody or antigen-binding fragment thereof is capable of activating T cells by inhibiting the nucleotidase activity of CD73 and therefore reducing adenosine level.

According to another particular aspect, the invention relates to an isolated monoclonal antibody or antigen-binding fragment thereof of the invention, wherein the antibody or antigen-binding fragment thereof is chimeric.

According to another particular aspect, the invention relates to an isolated monoclonal antibody or antigen-binding fragment thereof of the invention, wherein the antibody or antigen-binding fragment thereof is human or humanized.

According to another particular aspect, the invention relates to an isolated humanized monoclonal antibody or antigen-binding fragment thereof, wherein the isolated humanized antibody or antigen-binding fragment thereof comprises:

(1) a heavy chain variable region having the polypeptide sequence of SEQ ID NO:286, and a light chain variable region having the polypeptide sequence of SEQ ID NO:293;

(2) a heavy chain variable region having the polypeptide sequence of SEQ ID NO:282, and a light chain variable region having the polypeptide sequence of SEQ ID NO:290;

(3) a heavy chain variable region having the polypeptide sequence of SEQ ID NO:282, and a light chain variable region having the polypeptide sequence of SEQ ID NO:291;

(4) a heavy chain variable region having the polypeptide sequence of SEQ ID NO:282, and a light chain variable region having the polypeptide sequence of SEQ ID NO:292;

(5) a heavy chain variable region having the polypeptide sequence of SEQ ID NO:283, and a light chain variable region having the polypeptide sequence of SEQ ID NO:290;

(6) a heavy chain variable region having the polypeptide sequence of SEQ ID NO:283, and a light chain variable region having the polypeptide sequence of SEQ ID NO:291;

(7) a heavy chain variable region having the polypeptide sequence of SEQ ID NO:283, and a light chain variable region having the polypeptide sequence of SEQ ID NO:292;

(8) a heavy chain variable region having the polypeptide sequence of SEQ ID NO:284, and a light chain variable region having the polypeptide sequence of SEQ ID NO:290;

(9) a heavy chain variable region having the polypeptide sequence of SEQ ID NO:284, and a light chain variable region having the polypeptide sequence of SEQ ID NO:291;

(10) a heavy chain variable region having the polypeptide sequence of SEQ ID NO:284, and a light chain variable region having the polypeptide sequence of SEQ ID NO:292;

(11) a heavy chain variable region having the polypeptide sequence of SEQ ID NO:285, and a light chain variable region having the polypeptide sequence of SEQ ID NO:290;

(12) a heavy chain variable region having the polypeptide sequence of SEQ ID NO:285, and a light chain variable region having the polypeptide sequence of SEQ ID NO:291;

(13) a heavy chain variable region having the polypeptide sequence of SEQ ID NO:285, and a light chain variable region having the polypeptide sequence of SEQ ID NO:292;

(14) a heavy chain variable region having the polypeptide sequence of SEQ ID NO:283, and a light chain variable region having the polypeptide sequence of SEQ ID NO:293;

(15) a heavy chain variable region having the polypeptide sequence of SEQ ID NO:284, and a light chain variable region having the polypeptide sequence of SEQ ID NO:293;

(16) a heavy chain variable region having the polypeptide sequence of SEQ ID NO:285, and a light chain variable region having the polypeptide sequence of SEQ ID NO:293;

(17) a heavy chain variable region having the polypeptide sequence of SEQ ID NO:286, and a light chain variable region having the polypeptide sequence of SEQ ID NO:290;

(18) a heavy chain variable region having the polypeptide sequence of SEQ ID NO:286, and a light chain variable region having the polypeptide sequence of SEQ ID NO:291;

(19) a heavy chain variable region having the polypeptide sequence of SEQ ID NO:286, and a light chain variable region having the polypeptide sequence of SEQ ID NO:292;

(20) a heavy chain variable region having the polypeptide sequence of SEQ ID NO:287, and a light chain variable region having the polypeptide sequence of SEQ ID NO:294;

(21) a heavy chain variable region having the polypeptide sequence of SEQ ID NO:288, and a light chain variable region having the polypeptide sequence of SEQ ID NO:294;

(22) a heavy chain variable region having the polypeptide sequence of SEQ ID NO:289, and a light chain variable region having the polypeptide sequence of SEQ ID NO:294;

(23) a heavy chain variable region having the polypeptide sequence of SEQ ID NO:284, and a light chain variable region having the polypeptide sequence of SEQ ID NO:299;

(24) a heavy chain variable region having the polypeptide sequence of SEQ ID NO:295, and a light chain variable region having the polypeptide sequence of SEQ ID NO:299;

(25) a heavy chain variable region having the polypeptide sequence of SEQ ID NO:296, and a light chain variable region having the polypeptide sequence of SEQ ID NO:299;

(26) a heavy chain variable region having the polypeptide sequence of SEQ ID NO:297, and a light chain variable region having the polypeptide sequence of SEQ ID NO:299; or

(27) a heavy chain variable region having the polypeptide sequence of SEQ ID NO:298, and a light chain variable region having the polypeptide sequence of SEQ ID NO:299.

In another general aspect, the invention relates to an isolated nucleic acid encoding a monoclonal antibody or antigen-binding fragment thereof of the invention. It will be appreciated by those skilled in the art that the coding sequence of a protein can be changed (e.g., replaced, deleted, inserted, etc.) without changing the amino acid sequence of the protein. Accordingly, it will be understood by those skilled in the art that nucleic acid sequences encoding monoclonal antibodies or antigen-binding fragments thereof of the invention can be altered without changing the amino acid sequences of the proteins.

In another general aspect, the invention relates to a vector comprising an isolated nucleic acid encoding a monoclonal antibody or antigen-binding fragment thereof of the invention. Any vector known to those skilled in the art in view of the present disclosure can be used, such as a plasmid, a cosmid, a phage vector or a viral vector. In some embodiments, the vector is a recombinant expression vector such as a plasmid. The vector can include any element to establish a conventional function of an expression vector, for example, a promoter, ribosome binding element, terminator, enhancer, selection marker, and origin of replication. The promoter can be a constitutive, inducible or repressible promoter. A number of expression vectors capable of delivering nucleic acids to a cell are known in the art and can be used herein for production of an antibody or antigen-binding fragment thereof in the cell. Conventional cloning techniques or artificial gene synthesis can be used to generate a recombinant expression vector according to embodiments of the invention.

In another general aspect, the invention relates to a host cell comprising an isolated nucleic acid encoding a monoclonal antibody or antigen-binding fragment thereof of the invention. Any host cell known to those skilled in the art in view of the present disclosure can be used for recombinant expression of antibodies or antigen-binding fragments thereof of the invention. In some embodiments, the host cells are *E. coli* TG1 or BL21 cells (for expression of, e.g., an scFv or Fab antibody), CHO-DG44 or CHO-K1 cells or HEK293 cells (for expression of, e.g., a full-length IgG antibody). According to particular embodiments, the recombinant expression vector is transformed into host cells by conventional methods such as chemical transfection, heat shock, or electroporation, where it is stably integrated into the host cell genome such that the recombinant nucleic acid is effectively expressed.

In another general aspect, the invention relates to a method of producing a monoclonal antibody or antigen-binding fragment thereof of the invention, comprising culturing a cell comprising a nucleic acid encoding the monoclonal antibody or antigen-binding fragment thereof under conditions to produce a monoclonal antibody or antigen-binding fragment thereof of the invention, and recovering the antibody or antigen-binding fragment thereof from the cell or cell culture (e.g., from the supernatant). Expressed antibodies or antigen-binding fragments thereof can be harvested from the cells and purified according to conventional techniques known in the art and as described herein.

Pharmaceutical Compositions

In another general aspect, the invention relates to a pharmaceutical composition, comprising an isolated monoclonal antibody or antigen-binding fragment thereof of the invention and a pharmaceutically acceptable carrier. The term "pharmaceutical composition" as used herein means a product comprising an antibody of the invention together with a pharmaceutically acceptable carrier. Antibodies of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carrier can be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation can comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition can be formulated as an injectable which can be injected, for example, via an injection device (e.g., a syringe or an infusion pump). The injection can be delivered subcutaneously, intramuscularly, intraperitoneally, intravitreally, or intravenously, for example.

In another embodiment, the pharmaceutical composition is a solid formulation, e.g., a freeze-dried or spray-dried composition, which can be used as is, or whereto the physician or the patient adds solvents, and/or diluents prior to use. Solid dosage forms can include tablets, such as compressed tablets, and/or coated tablets, and capsules (e.g., hard or soft gelatin capsules). The pharmaceutical composition can also be in the form of sachets, dragees, powders, granules, lozenges, or powders for reconstitution, for example.

The dosage forms can be immediate release, in which case they can comprise a water-soluble or dispersible carrier, or they can be delayed release, sustained release, or modified release, in which case they can comprise water-insoluble polymers that regulate the rate of dissolution of the dosage form in the gastrointestinal tract or under the skin.

In other embodiments, the pharmaceutical composition can be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer can be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomersal, and mixtures thereof. The preservative can be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the isotonic agents include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars can be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. The isotonic agent can be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent can be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer can be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant can, for example, be selected from the group consisting of anionic surfactants, cationic surfactants, nonionic surfactants, and/or zwitterionic surfactants. The surfactant can be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA, and/or benzamidine hydrochloric acid (HCl). The protease inhibitor can be present individually or in the aggregate, in a concentration from about 0.1 mg/ml to about 20 mg/ml. Pharmaceutical compositions comprising each one of these specific protease inhibitors constitute alternative embodiments of the invention.

In another general aspect, the invention relates to a method of producing a pharmaceutical composition comprising a monoclonal antibody or antigen-binding fragment thereof of the invention, comprising combining a monoclonal antibody or antigen-binding fragment thereof with a pharmaceutically acceptable carrier to obtain the pharmaceutical composition.

Methods of Use

In another general aspect, the invention relates to a method of inhibiting the nucleotidase activity of CD73 in a subject in need thereof, the method comprising administering to the subject an isolated monoclonal antibody or antigen binding fragment thereof that specifically binds to CD73 or a pharmaceutical composition of the invention.

In another general aspect, the invention relates to a method of preventing the dimerization of CD73 in a subject in need thereof, the method comprising administering to the subject an isolated monoclonal antibody or antigen binding fragment thereof that specifically binds to CD73 or a pharmaceutical composition of the invention.

In another general aspect, the invention relates to a method of inducing the internalization of CD73 in a subject in need thereof, the method comprising administering to the subject an isolated monoclonal antibody or antigen binding fragment thereof that specifically binds to CD73 or a pharmaceutical composition of the invention. Internalization of the CD73 into the cell results in a reduction of the cell surface content of CD73. Levels of CD73 on the cell surface can be measured by methods known in the art, e.g., immunohistochemistry methods.

The functional activity of antibodies and antigen-binding fragments thereof that bind CD73 can be characterized by methods known in the art and as described herein. Cell expressing CD73 can be preincubated with the antibody followed by measuring the CD73 nucleotidase activity on the cell surface in the presence of the antibody. Methods for characterizing antibodies and antigen-binding fragments thereof that bind CD73 include, but are not limited to, affinity and specificity assays including Biacore, ELISA, and OctetRed analysis; the functional activity of an anti-CD73 mAb can also be assessed in a nucleotidase activity assay. According to particular embodiments, the methods for characterizing antibodies and antigen-binding fragments thereof that bind CD73 include those described below.

In another general aspect, the invention relates to a method of treating a cancer in a subject in need thereof, comprising administering to the subject an isolated monoclonal antibody or antigen binding fragment thereof that specifically binds to CD73 or a pharmaceutical composition of the invention. The cancer can, for example, be selected from, but not limited to, a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors.

In another general aspect, the invention relates to a method of treating an inflammatory disease in a subject in need thereof, comprising administering to the subject an isolated monoclonal antibody or antigen binding fragment thereof that specifically binds to CD73 or a pharmaceutical composition of the invention.

According to embodiments of the invention, the pharmaceutical composition comprises a therapeutically effective amount of an anti-CD73 antibody or antigen-binding fragment thereof. As used herein, the term "therapeutically effective amount" refers to an amount of an active ingredient or component that elicits the desired biological or medicinal response in a subject. A therapeutically effective amount can be determined empirically and in a routine manner, in relation to the stated purpose.

As used herein with reference to anti-CD73 antibodies or antigen-binding fragments thereof, a therapeutically effective amount means an amount of the anti-CD73 antibody or antigen-binding fragment thereof that modulates a tumor reduction response in a subject in need thereof. Also, as used herein with reference to anti-CD73 antibodies or antigen-binding fragments thereof, a therapeutically effective amount means an amount of the anti-CD73 antibody or antigen-binding fragment thereof that results in treatment of a disease, disorder, or condition; prevents or slows the progression of the disease, disorder, or condition; or reduces or completely alleviates symptoms associated with the disease, disorder, or condition.

According to particular embodiments, the disease, disorder or condition to be treated is cancer, preferably a cancer selected from the group consisting of a lung cancer, a gastric cancer, a colon cancer, a hepatocellular carcinoma, a renal cell carcinoma, a bladder urothelial carcinoma, a metastatic melanoma, a breast cancer, an ovarian cancer, a cervical cancer, a head and neck cancer, a pancreatic cancer, a glioma, a glioblastoma, and other solid tumors, and a non-Hodgkin's lymphoma (NHL), an acute lymphocytic leukemia (ALL), a chronic lymphocytic leukemia (CLL), a chronic myelogenous leukemia (CML), a multiple myeloma (MM), an acute myeloid leukemia (AML), and other liquid tumors. According to other particular embodiments, the disease, disorder or condition to be treated is an inflammatory disease.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

According to particular embodiments, the compositions described herein are formulated to be suitable for the intended route of administration to a subject. For example, the compositions described herein can be formulated to be suitable for intravenous, subcutaneous, or intramuscular administration.

As used herein, the terms "treat," "treating," and "treatment" are all intended to refer to an amelioration or reversal of at least one measurable physical parameter related to a cancer and/or an inflammatory disease, disorder or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition, such as a tumor or more preferably a cancer. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

According to particular embodiments, a composition of the invention is used in the treatment of a cancer and/or an inflammatory disease, disorder or condition. For cancer therapy, it can be used in combination with another treatment including, but not limited to, a chemotherapy, an anti-CD20 mAb, an anti-TIM-3 mAb, an anti-LAG-3 mAb, an anti-CD47 mAb, an anti-apelin mAb, an anti-claudin18.2 mAb, an anti-DLL3 mAb, an anti-FRα (folate receptor alpha) mAb, an anti-TIP-1 mAb, an anti-CTLA-4 antibody, an anti-PD-L1 antibody, an anti-PD-1 antibody, a PD-1/PD-L1 therapy, other immuno-oncology drugs, an antiangiogenic agent, a radiation therapy, an antibody-drug conjugate (ADC), a targeted therapy, or other anticancer drugs. Anti-CD73 antibodies can be used to construct bispecific antibodies with partner mAbs against PD-1, PD-L1, LAG3, TIM-3, CTLA-4, EGFR, HER-2, CD19, CD20, CD33, CD47, CD3, apelin, claudin18.2, DLL3, TIP-1, folate receptor alpha (FRα), and/or other tumor surface antigens to treat cancers/tumors that express both CD73 and the specific tumor associated antigen.

As used herein, the term "in combination," in the context of the administration of two or more therapies to a subject, refers to the use of more than one therapy. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In another general aspect, the invention relates to a method of determining a level of CD73 in a subject. The methods comprise (a) obtaining a sample from the subject; (b) contacting the sample with a monoclonal antibody or antigen-binding fragment thereof of the invention; and (c) determining a level of CD73 in the subject.

In another general aspect, the invention relates to a method of determining the ecto-5'-nucleotidase activity of CD73 in a subject, wherein the enzyme activity can be fully inhibited by the monoclonal antibody or antigen-binding fragment thereof of the invention. The methods comprise (a) obtaining a sample from the subject; (b) contacting the sample with an antibody or antigen-binding fragment thereof of the invention; and (c) determining the ecto-5'-nucleotidase activity of CD73 in the subject.

As used herein, "sample" refers to a biological sample isolated from a subject and can include, but is not limited to, whole blood, serum, plasma, blood cells, endothelial cells, tissue biopsies (e.g., a cancer tissue), lymphatic fluid, ascites fluid, interstitial fluid, bone marrow, cerebrospinal fluid, saliva, mucous, sputum, sweat, urine, or any other secretion, excretion, or other bodily fluids. A "blood sample" refers to whole blood or any fraction thereof, including blood cells, serum, and plasma.

In certain embodiments, the level of CD73 in the subject can be determined utilizing assays selected from, but not limited to, a Western blot assay, an ELISA assay, and/or immunohistochemistry (IHC). Relative protein levels can be determined by utilizing Western blot analysis and IHC, and absolute protein levels can be determined by utilizing an ELISA assay. When determining the relative levels of CD73, the levels of CD73 can be determined between at least two samples, e.g., between samples from the same subject at different time points, between samples from different tissues in the same subject, and/or between samples from different subjects. Alternatively, when determining absolute levels of CD73, such as by an ELISA assay, the absolute level of CD73 in the sample can be determined by creating a standard for the ELISA assay prior to testing the sample. A person skilled in the art would understand which analytical techniques to utilize to determine the level of CD73 in a sample from the subject utilizing the antibodies or antigen-binding fragments thereof of the invention.

In certain embodiments, the ecto-5'-nucleotidase activity of CD73 in the subject can be determined using assays known in the art, e.g., see Geoghegan et al., MAbs 8:454-67 (2016) and Hay et al., Oncoimmunology August 5(8): e1208875 (2016). A person skilled in the art would understand which analytical techniques to utilize to determine the ecto-5'-nucleotidase activity of CD73 in a sample from the subject.

Utilizing methods of determining a level of CD73 or a level of the ecto-5'-nucleotidase activity of CD73 in a sample from a subject can lead to the diagnosis of abnormal (elevated, reduced, or insufficient) CD73 levels and/or activities in a disease and making appropriate therapeutic decisions. Such a disease can be selected from, but not limited to, a cancer and/or an inflammatory disease. Additionally, by monitoring the levels and/or activity of CD73 in a subject, the risk of developing a disease as indicated above can be determined based on the knowledge of the level and/or activity of CD73 in a particular disease and/or during the progression of the particular disease.

EMBODIMENTS

The invention provides also the following non-limiting embodiments.

Embodiment 1 is an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of
  a. SEQ ID NOs:89, 90, 91, 149, 150 and 151, respectively;
  b. SEQ ID NOs:41, 42, 43, 101, 102 and 103, respectively;
  c. SEQ ID NOs:44, 45, 46, 104, 105 and 106, respectively;
  d. SEQ ID NOs:47, 48, 49, 107, 108 and 109, respectively;
  e. SEQ ID NOs:50, 51, 52, 110, 111 and 112, respectively;
  f. SEQ ID NOs:53, 54, 55, 113, 114 and 115, respectively;
  g. SEQ ID NOs:56, 57, 58, 116, 117 and 118, respectively;
  h. SEQ ID NOs:59, 60, 61, 119, 120 and 121, respectively;
  i. SEQ ID NOs:62, 63, 64, 122, 123 and 124, respectively;
  j. SEQ ID NOs:65, 66, 67, 125, 126 and 127, respectively;
  k. SEQ ID NOs:68, 69, 70, 128, 129 and 130, respectively;
  l. SEQ ID NOs:71, 72, 73, 131, 132 and 133, respectively;
  m. SEQ ID NOs:74, 75, 76, 134, 135 and 136, respectively;
  n. SEQ ID NOs:77, 78, 79, 137, 138 and 139, respectively;
  o. SEQ ID NOs:80, 81, 82, 140, 141 and 142, respectively;
  p. SEQ ID NOs:83, 84, 85, 143, 144 and 145, respectively;
  q. SEQ ID NOs:86, 87, 88, 146, 147 and 148, respectively;
  r. SEQ ID NOs:92, 93, 94, 152, 153 and 154, respectively;
  s. SEQ ID NOs:95, 96, 97, 155, 156 and 157, respectively; or
  t. SEQ ID NOs:98, 99, 100, 158, 159 and 160, respectively;
wherein the antibody or antigen-binding fragment thereof specifically binds to CD73, preferably human CD73.

Embodiment 2 is an isolated monoclonal antibody or antigen-binding fragment thereof comprising a heavy chain complementarity determining region 1 (HCDR1), HCDR2, HCDR3, a light chain complementarity determining region 1 (LCDR1), LCDR2, and LCDR3, having the polypeptide sequences of
  a. SEQ ID NOs:209, 210, 211, 269, 270 and 271, respectively;
  b. SEQ ID NOs:161, 162, 163, 221, 222 and 223, respectively;
  c. SEQ ID NOs:164, 165, 166, 224, 225 and 226, respectively;
  d. SEQ ID NOs:167, 168, 169, 227, 228 and 229, respectively;
  e. SEQ ID NOs:170, 171, 172, 230, 231 and 232, respectively;
  f. SEQ ID NOs:173, 174, 175, 233, 234 and 235, respectively;
  g. SEQ ID NOs:176, 177, 178, 236, 237 and 238, respectively;
  h. SEQ ID NOs:179, 180, 181, 239, 240 and 241, respectively;
  i. SEQ ID NOs:182, 183, 184, 242, 243 and 244, respectively;
  j. SEQ ID NOs:185, 186, 187, 245, 246 and 247, respectively;
  k. SEQ ID NOs:188, 189, 190, 248, 249 and 250, respectively;
  l. SEQ ID NOs:191, 192, 193, 251, 252 and 253, respectively;
  m. SEQ ID NOs:194, 195, 196, 254, 255 and 256, respectively;
  n. SEQ ID NOs:197, 198, 199, 257, 258 and 259, respectively;
  o. SEQ ID NOs:200, 201, 202, 260, 261 and 262, respectively;
  p. SEQ ID NOs:203, 204, 205, 263, 264 and 265, respectively;
  q. SEQ ID NOs:206, 207, 208, 266, 267 and 268, respectively;
  r. SEQ ID NOs:212, 213, 214, 272, 273 and 274, respectively;
  s. SEQ ID NOs:215, 216, 217, 275, 276 and 277, respectively; or
  t. SEQ ID NOs:218, 219, 220, 278, 279 and 280, respectively;
wherein the antibody or antigen-binding fragment thereof specifically binds to CD73, preferably human CD73.

Embodiment 3 is the isolated monoclonal antibody or antigen-binding fragment of embodiment 1 or 2, comprising a heavy chain variable region having a polypeptide sequence at least 95% identical to SEQ ID NO:33, 1, 3, 5, 7, 9, 11, 13, 15, 17, 19, 21, 23, 25, 27, 29, 31, 35, 37 or 39, or a light chain variable region having a polypeptide sequence at least 95% identical to SEQ ID NO:34, 2, 4, 6, 8, 10, 12, 14, 16, 18, 20, 22, 24, 26, 28, 30, 32, 36, 38 or 40.

Embodiment 4 is the isolated monoclonal antibody or antigen-binding fragment of any one of embodiments 1-3, comprising
  (a) a heavy chain variable region having the polypeptide sequence of SEQ ID NO:33, and a light chain variable region having the polypeptide sequence of SEQ ID NO:34;
  (b) a heavy chain variable region having the polypeptide sequence of SEQ ID NO:1, and a light chain variable region having the polypeptide sequence of SEQ ID NO:2;
  (c) a heavy chain variable region having the polypeptide sequence of SEQ ID NO:3, and a light chain variable region having the polypeptide sequence of SEQ ID NO:4;
  (d) a heavy chain variable region having the polypeptide sequence of SEQ ID NO:5, and a light chain variable region having the polypeptide sequence of SEQ ID NO:6;

(e) a heavy chain variable region having the polypeptide sequence of SEQ ID NO:7, and a light chain variable region having the polypeptide sequence of SEQ ID NO:8;
(f) a heavy chain variable region having the polypeptide sequence of SEQ ID NO:9, and a light chain variable region having the polypeptide sequence of SEQ ID NO:10;
(g) a heavy chain variable region having the polypeptide sequence of SEQ ID NO:11, and a light chain variable region having the polypeptide sequence of SEQ ID NO:12;
(h) a heavy chain variable region having the polypeptide sequence of SEQ ID NO:13, and a light chain variable region having the polypeptide sequence of SEQ ID NO:14;
(i) a heavy chain variable region having the polypeptide sequence of SEQ ID NO:15, and a light chain variable region having the polypeptide sequence of SEQ ID NO:16;
(j) a heavy chain variable region having the polypeptide sequence of SEQ ID NO:17, and a light chain variable region having the polypeptide sequence of SEQ ID NO:18;
(k) a heavy chain variable region having the polypeptide sequence of SEQ ID NO:19, and a light chain variable region having the polypeptide sequence of SEQ ID NO:20;
(l) a heavy chain variable region having the polypeptide sequence of SEQ ID NO:21, and a light chain variable region having the polypeptide sequence of SEQ ID NO:22;
(m) a heavy chain variable region having the polypeptide sequence of SEQ ID NO:23, and a light chain variable region having the polypeptide sequence of SEQ ID NO:24;
(n) a heavy chain variable region having the polypeptide sequence of SEQ ID NO:25, and a light chain variable region having the polypeptide sequence of SEQ ID NO:26;
(o) a heavy chain variable region having the polypeptide sequence of SEQ ID NO:27, and a light chain variable region having the polypeptide sequence of SEQ ID NO:28;
(p) a heavy chain variable region having the polypeptide sequence of SEQ ID NO:29, and a light chain variable region having the polypeptide sequence of SEQ ID NO:30;
(q) a heavy chain variable region having the polypeptide sequence of SEQ ID NO:31, and a light chain variable region having the polypeptide sequence of SEQ ID NO:32;
(r) a heavy chain variable region having the polypeptide sequence of SEQ ID NO:35, and a light chain variable region having the polypeptide sequence of SEQ ID NO:36;
(s) a heavy chain variable region having the polypeptide sequence of SEQ ID NO:37, and a light chain variable region having the polypeptide sequence of SEQ ID NO:38; or
(t) a heavy chain variable region having the polypeptide sequence of SEQ ID NO:39, and a light chain variable region having the polypeptide sequence of SEQ ID NO:40.

Embodiment 5 is the isolated monoclonal antibody or antigen-binding fragment thereof of any one of embodiments 1-4, wherein the monoclonal antibody or antigen-binding fragment thereof inhibits the enzyme activity of soluble and/or cell-surface CD73.

Embodiment 6 is the isolated monoclonal antibody or antigen-binding fragment thereof of any one of embodiments 1-4, wherein the monoclonal antibody or antigen-binding fragment thereof prevents the dimerization of CD73.

Embodiment 7 is the isolated monoclonal antibody or antigen-binding fragment thereof of any one of embodiments 1-4, wherein the monoclonal antibody or antigen-binding fragment thereof induces the internalization of CD73.

Embodiment 8 is the isolated monoclonal antibody or antigen-binding fragment of any one of embodiments 1-7, wherein the antibody or antigen-binding fragment thereof is chimeric.

Embodiment 9 is the isolated monoclonal antibody or antigen-binding fragment of any one of embodiments 1-8, wherein the antibody or antigen-binding fragment thereof is human or humanized.

Embodiment 10 is the isolated monoclonal antibody or antigen-binding fragment of any one of embodiments 1-9, wherein the antibody or antigen-binding fragment thereof comprises:
(1) a heavy chain variable region having the polypeptide sequence of SEQ ID NO:286, and a light chain variable region having the polypeptide sequence of SEQ ID NO:293;
(2) a heavy chain variable region having the polypeptide sequence of SEQ ID NO:282, and a light chain variable region having the polypeptide sequence of SEQ ID NO:290;
(3) a heavy chain variable region having the polypeptide sequence of SEQ ID NO:282, and a light chain variable region having the polypeptide sequence of SEQ ID NO:291;
(4) a heavy chain variable region having the polypeptide sequence of SEQ ID NO:282, and a light chain variable region having the polypeptide sequence of SEQ ID NO:292;
(5) a heavy chain variable region having the polypeptide sequence of SEQ ID NO:283, and a light chain variable region having the polypeptide sequence of SEQ ID NO:290;
(6) a heavy chain variable region having the polypeptide sequence of SEQ ID NO:283, and a light chain variable region having the polypeptide sequence of SEQ ID NO:291;
(7) a heavy chain variable region having the polypeptide sequence of SEQ ID NO:283, and a light chain variable region having the polypeptide sequence of SEQ ID NO:292;
(8) a heavy chain variable region having the polypeptide sequence of SEQ ID NO:284, and a light chain variable region having the polypeptide sequence of SEQ ID NO:290;
(9) a heavy chain variable region having the polypeptide sequence of SEQ ID NO:284, and a light chain variable region having the polypeptide sequence of SEQ ID NO:291;
(10) a heavy chain variable region having the polypeptide sequence of SEQ ID NO:284, and a light chain variable region having the polypeptide sequence of SEQ ID NO:292;

(11) a heavy chain variable region having the polypeptide sequence of SEQ ID NO:285, and a light chain variable region having the polypeptide sequence of SEQ ID NO:290;

(12) a heavy chain variable region having the polypeptide sequence of SEQ ID NO:285, and a light chain variable region having the polypeptide sequence of SEQ ID NO:291;

(13) a heavy chain variable region having the polypeptide sequence of SEQ ID NO:285, and a light chain variable region having the polypeptide sequence of SEQ ID NO:292;

(14) a heavy chain variable region having the polypeptide sequence of SEQ ID NO:283, and a light chain variable region having the polypeptide sequence of SEQ ID NO:293;

(15) a heavy chain variable region having the polypeptide sequence of SEQ ID NO:284, and a light chain variable region having the polypeptide sequence of SEQ ID NO:293;

(16) a heavy chain variable region having the polypeptide sequence of SEQ ID NO:285, and a light chain variable region having the polypeptide sequence of SEQ ID NO:293;

(17) a heavy chain variable region having the polypeptide sequence of SEQ ID NO:286, and a light chain variable region having the polypeptide sequence of SEQ ID NO:290;

(18) a heavy chain variable region having the polypeptide sequence of SEQ ID NO:286, and a light chain variable region having the polypeptide sequence of SEQ ID NO:291;

(19) a heavy chain variable region having the polypeptide sequence of SEQ ID NO:286, and a light chain variable region having the polypeptide sequence of SEQ ID NO:292;

(20) a heavy chain variable region having the polypeptide sequence of SEQ ID NO:287, and a light chain variable region having the polypeptide sequence of SEQ ID NO:294;

(21) a heavy chain variable region having the polypeptide sequence of SEQ ID NO:288, and a light chain variable region having the polypeptide sequence of SEQ ID NO:294;

(22) a heavy chain variable region having the polypeptide sequence of SEQ ID NO:289, and a light chain variable region having the polypeptide sequence of SEQ ID NO:294;

(23) a heavy chain variable region having the polypeptide sequence of SEQ ID NO:284, and a light chain variable region having the polypeptide sequence of SEQ ID NO:299;

(24) a heavy chain variable region having the polypeptide sequence of SEQ ID NO:295, and a light chain variable region having the polypeptide sequence of SEQ ID NO:299;

(25) a heavy chain variable region having the polypeptide sequence of SEQ ID NO:296, and a light chain variable region having the polypeptide sequence of SEQ ID NO:299;

(26) a heavy chain variable region having the polypeptide sequence of SEQ ID NO:297, and a light chain variable region having the polypeptide sequence of SEQ ID NO:299; or

(27) a heavy chain variable region having the polypeptide sequence of SEQ ID NO:298, and a light chain variable region having the polypeptide sequence of SEQ ID NO:299.

Embodiment 11 is the isolated monoclonal antibody or antigen-binding fragment of any one of embodiments 1-10, wherein the antibody or antigen-binding fragment thereof is capable of activating T cells.

Embodiment 12 is an isolated nucleic acid encoding the monoclonal antibody or antigen-binding fragment of any one of embodiments 1-11.

Embodiment 13 is a vector comprising the isolated nucleic acid of embodiment 12.

Embodiment 14 is a host cell comprising the vector of embodiment 13.

Embodiment 15 is a pharmaceutical composition, comprising the isolated monoclonal antibody or antigen-binding fragment of any one of embodiments 1-11 and a pharmaceutically acceptable carrier.

Embodiment 16 is a method of inhibiting the nucleotidase activity of CD73 in a subject in need thereof, comprising administering to the subject the pharmaceutical composition of embodiment 15.

Embodiment 17 is a method of preventing the dimerization of CD73 in a subject in need thereof, comprising administering to the subject the pharmaceutical composition of claim 15.

Embodiment 18 is a method of inducing the internalization of CD73 in a subject in need thereof, comprising administering to the subject the pharmaceutical composition of claim 15.

Embodiment 19 is a method of treating cancer in a subject in need thereof, comprising administering to the subject the pharmaceutical composition of embodiment 15.

Embodiment 20 is a method of producing the monoclonal antibody or antigen-binding fragment of any one of embodiments 1-11, comprising culturing a cell comprising a nucleic acid encoding the monoclonal antibody or antigen-binding fragment under conditions to produce the monoclonal antibody or antigen-binding fragment, and recovering the antibody or antigen-binding fragment from the cell or culture.

Embodiment 21 is a method of producing a pharmaceutical composition comprising the monoclonal antibody or antigen-binding fragment of any one of embodiments 1-11, comprising combining the monoclonal antibody or antigen-binding fragment with a pharmaceutically acceptable carrier to obtain the pharmaceutical composition.

Embodiment 22 is a method of determining a level of CD73 in a subject, the method comprising:
  a. obtaining a sample from the subject;
  b. contacting the sample with the isolated monoclonal antibody or antigen-binding fragment thereof of any one of embodiments 1-11; and
  c. determining a level of CD73 in the subject.

Embodiment 23 is the method of embodiment 22, wherein the sample is a tissue sample.

Embodiment 24 is the method of embodiment 23, wherein the tissue sample is a cancer tissue sample.

Embodiment 25 is the method of embodiment 22, wherein the sample is a blood sample.

Embodiment 26 is a method of determining the ecto-5'-nucleotidase activity of CD73 in a subject, the method comprising:
  a. obtaining a sample from the subject;
  b. contacting the sample with an isolated monoclonal antibody or antigen-binding fragment thereof of any one of embodiments 1-11; and c. determining the ecto-5'-nucleotidase activity of CD73 in the subject.

Embodiment 27 is the method of embodiment 26, wherein the sample is a tissue sample.

Embodiment 28 is the method of embodiment 27, wherein the tissue sample is a cancer tissue sample.

Embodiment 29 is the method of embodiment 26, wherein the sample is a blood sample.

EXAMPLES

Example 1: Identification of Anti-CD73 Monoclonal Antibodies

Mice were immunized with a mixture of human CD73 (huCD73-HIS; containing residues 27-547) and mouse CD73 (mCD73-HIS; containing residues 29-549) fusion proteins, both with the HIS tag at the C-terminus. Plasma titer was determined by ELISA. After euthanization, spleens and lymph nodes were collected to produce hybridomas. Hybridomas were grown in 384-well tissue culture plates and supernatants from individual wells were screened by ELISA using huCD73-HIS and fluorescence activated cell sorting (FACS) using MDA-MB-231 cells. Positive clones were further analyzed by a nucleotidase activity assay with CD73 immobilized on the plate. Top positive clones that showed inhibition of the nucleotidase activity were isolated and sequenced.

Sequences of heavy and light chain variable regions for anti-CD73 monoclonal antibodies are provided in Tables 1 and 2, and the CDR regions for the anti-CD73 monoclonal antibodies are provided in Tables 3-6.

TABLE 1

Sequences of heavy chain variable regions for anti-CD73 mAbs

| mAb clones | VH | ID |
|---|---|---|
| 37C7A | QVTLKESGPGILQPSQTLSLTCSFSGFSLSTFGMGVTWIRQPSGKGLEWL AHIWWDDDMYYNPALKSRLTISKDTSKNQVFLKIANVDTADTATYYCARS PITTVVADYWGQGSTLTVSS | 1 |
| 38C16A | QVQLQQSGAELMKPGASVKISCKATGYTFSSYWIEWVKQRPGHGLEWIGE ILPGSGSTNYNEKFKGKATFTADTSSNTAYMQLSSLTSEDSAVYYCARGD YFGSSYRGPYWGQGTLVTVSA | 3 |
| 39G8A | QVQLQQPGAELVMPGASVKLSCKASGYTFTSYWMHWVKQRPGQGLEWIGE IDPSGGYTNYNQKFKGKSTLTVDKSSSTAYMQLSRLTSEDSAVYYCARNY YYGSSGTMDYWGQGTSVTVSS | 5 |
| 43E8A | QVQLQQSGAELMKPGASVKISCKATGYTFSNYWIEWVKQRPGHGLEWIGE ILPGNVITNYNEKFKGKATFTADTSSNTAYMQLSSLTSEDSAVYYCARRG DDGYLYAMDYWGQGTSVTVSS | 7 |
| 46J3A | EVQLQQSGPELVKPGASVKISCKASGYTFTDYYMHWVKQPGQGLEWIGE IYPGSGNTYYNEKFKGKATLTADRSSSTVYMLLSSLTSEDSAVYFCARYW DYYGSTYGYFDVWGAGTTVTVSS | 9 |
| 46O19A | EVQLQQSGPELVKPGASVKMSCKASGYTFTDYNMHWVKQSHGKSLEWIGY INPNNGGTSYNQKFKGKATLTVNKSSSTAYMELRSLTSEDSAVYYCARDY FWYFDVWGTGTTVTVSS | 11 |
| 47H24A | QVQLKQSGPGLVQPSQSLSITCTVSGFSLTSYGVHWVRQSPGKGLEWLGV IWSGGSTDYNAAFISRLSISKDNSKSQVFFKMNSLQANDTAIYYCASQYV AYWGQGTLVTVST | 13 |
| 49O5A | QVQLQQPGTELVKPGASVKLSCKASGYTFTSYWMHWVKQRPGQGLEWIGN INPSNGGTNYNEKFKSKATLTVDKSSSTAYMQLSSLTSEDSAVYYCARSK SNYGYYAMDYWGQGTSVTVSS | 15 |
| 50B10A | QVQLQQPGAELVKPGASVKLSCKSSGYTFTSYWMHWVKQRPGQGLEWIGE INPSNGRTNYNEKFKSKATLTVDKSSSTAYMQLSSLTSEDSAVYYCARSE GRVYYDYFYAMDYWGQGTSVTVSS | 17 |
| 50H17A | QVQLQQSGAELVRPGTSVKVSCKASGYAFTNYLIEWVKQRPGQGLEWIGV INPGSGGTNYNEKFKGKATLTADKSSSTAYMQLSSLTSEDSAVYFCARDY YWYFDVWGTGTTVTVSS | 19 |
| 50E16A | ELARPWASVKISCQAFYTFSRRMHFAIRDTNYWMQWVKQRPGQGLEWIGA IYPGNGDTSYNQKFKVKATLTADKSSSTAYMQLSSLTSEDSAVYYCATYY SNYGGAMDYWGQGTSVTVSS | 21 |
| 50F1A | QIQLVQSGPELKKPGETVKISCKASGYTFTDYSMHWVKQAPGKGLKWMGW INTETGEPTYADDFKGRFAFSLETSASTAYLQINNLKNEDTATYFCARDI FWAMDYWGQGTSVTVSS | 23 |
| 54I14A | QAYLQQSGAELVRPGASVKMSCKASGYTFTSYNMHWVKQTPRQGLEWIGA IYPGNGDTSYNQKFKGKATLTVDKSSSTAYMQLSSLTSEDSAVYFCARYD YDAMDYWGQGTSVTVSS | 25 |

TABLE 1-continued

Sequences of heavy chain variable regions for anti-CD73 mAbs

| mAb clones | VH | ID |
|---|---|---|
| 52K11A | EIQLQQSGAELVKPGASVKISCKASGYSFTGYNMNWVKQSHGKSLEWIGN INPYYGSTSYNQKFKGKATLTVDKSSSTAYMQLNSLTSKDSAVYYCAGSS YVDYAMDYWGQGTSVTVSS | 27 |
| 53H21A | EVQLQQSGPELVKPGASVKMSCKASGYTFTSYVMHWVKQKPGQGLEWIGY IIPYNDGTKYNEKFEGKATLTSDKSSSTAYMELSSLTSEDSAVYYCARWG NWDYFDYWGQGTTLTVSS | 29 |
| 53I12A | QVQLQQPGAELVKPGASVKLSCKAPGYTFTSYWINWVKQRPGQGLEWIGN IYAGSSSSNYNEKFKSKATLTVDTSSSTAYMQLSSLTSDDSAVYYCARSG HGYDGFAYWGQGTLVTVSA | 31 |
| 60A9A | QVQLQQSGAELVKPGASVKISCKASGYAFSSYWMNWVKQRPGKGLEWIGQ IYPGDGDTYYSGKFKGKATLTAAKSSSTAYMQLSSLTSEDSAVYFCAREA IYYGNYVFTYWGQGTLVTVSA | 33 |
| 39J9A | QVQLQQSGAELVRPGTSVKVSCKASGYAFTNYLIEWIKQRPGQGLEWIGL INPGSGGTNYIEKFKGKATLTADKSSSTAYMQLSSLTSEDSAVYFCARRG DYYGNPFDYWGQGTTLTVSS | 35 |
| 49H8A | QVQLQQPGAELVKPGASVKLSCKASGYTFTNYWMQWVRQRPGQGLEWIGE IDPSDNYTHYNQKFKGEATLTVDTSSSTAYMQLSSLTSEDSAVYYCARGY YGYSPSWFAYWGQGTLVTVSA | 37 |
| 51B10A | EVQLQQSGPELVKPGASVKISCKASGYSFTGYYMHWVKQSHVKSLEWIGR INPYSGATNSNQNFKDKASLTVDKSSSTAYMELHSLTSEDSAVYYCARSY YGAMDYWGQGTSVTVSS | 39 |

VH: heavy chain variable region

TABLE 2

Sequences of light chain variable regions for anti-CD73 mAbs

| mAb | VL | ID |
|---|---|---|
| 37C7A | DVVMTQTPLSLPVSLGDQASISCRSSQNLVHSYGNTYLHWYLQKPGQSPK LLIYKVSNRFSGVPDRFSGSGSGTDFTLKISRVEAEDLGVYFCSQNTHVP WTFGGGTKLEIQ | 2 |
| 38C16A | DVVMTQTPLTLSVTIGQPASISCKSSQSLLDSDGRTYLNWLLRPGQSPK RLIYLVSKLDSGVPDRFTGSGSGTDFTLKISRVEAEDLGVYYCWQGTHFP HTFGGGTKLEIK | 4 |
| 39G8A | DIVMTQSPSSLAMSVGQKVTMSCKSSQSLLNSSNQKNYLAWYQQKPGQSP KLLVYFASTRESGVPDRFIGSGSGTDFTLTISSVQAEDLADYFCQQHYST PYTFGGGTKLEIK | 6 |
| 43E8A | DIVLTQSPASLAVSLGQRATISCRASESVDNYGISFMNWFQQKPGQPPKL LIYAASNQGSGVPARFSGSGSGTDFSLNIHPMEEDDTAMYFCQQSKEVPF TFGSGTKLEIK | 8 |
| 46J3A | DVQITQSPSYLAASPGETITINCRASKNISKYLAWYQEIPGKTYNLLIYS GSTLQSGIPSRFSGSGSGTDFTLTISSLEPEDFAMYYCQQHNEYPFTFGS GTKLEIK | 10 |
| 46O19A | DIVMTQSPSSLTVTAGEKVTMSCKSSQSLLNSGNQKNYLTWYQEKPGQPP KVLIYWASTRESGVPDRFTGSGSGTDFTLTISSVQAEDLAVYYCQNDYSY PLTFGAGTKLELK | 12 |
| 47H24A | DIQMTQSPSSLSASLGERVSLTCRASQDIGSRLTWLQQEPDGTIKRLIYA TSSLDSGVPKRFSGSRSGSDYSLTISSLESEDFVDYFCLQYASSPFTFGS GTKLEIK | 14 |
| 49O5A | DIQMTQSSSYLSVSLGGRVTITCEASDHIDNWLAWYQQKPGNAPRLLISG ATSLETGVPSRFSGSGSGKDYTLSITSLQTEDVATYYCQQYWSSPFTFGS GTKLEIK | 16 |
| 50B10A | DIQMTQTTSSLSASLGDRVTISCRASQDISNYLNWYQQKPDGTVKLLIYY TSRLHSGVPSRFSGSGSGTDYSLTISNLEQEDIATYFCQQGNTLPWTFGG GTKLEIK | 18 |

TABLE 2-continued

Sequences of light chain variable regions for anti-CD73 mAbs

| mAb | VL | ID |
|---|---|---|
| 50H17A | DIVMTQSPSSLTVTAGEKVTMSCKSSQSLLNSGNQKNYLTWYQQKPGQPP KVLIYWASTRESGVPDRFTGSGSGTDFTLTISSVQAEDLAVYYCQNDYSY PLTFGAGTKLELK | 20 |
| 50E16A | DIVMTQFHKFMSTSVGDRVSITCKASQDVGTAVAWYQQKPGQSPKWYWAS TRHTGVPDRFTGSGSGTDFTLTISNVQSEDLADYFCQQYSSYPYTFGGGT KLEIK | 22 |
| 50F1A | DIVMTQSPSSLTVTAGEKVTMSCKSSQSLLNSGNQKNYLTWYQQKPGQPP KLLIYWASTRESGVPDRFTGSGSGTDFTLTISSVQAEDLAVYYCQNDYSY PLTFGAGTKLELK | 24 |
| 54I14A | DIQMTQSPASLSASVGETVTITCRASENIYSYFAWYQQKQGKSPQLLVYN AKTLAEGVPSRFSGSGSGTQFSLKINSLQPEDFGSYYCQHHYGTPFTFGS GTKLEIK | 26 |
| 52K11A | DIVMTQAAISNPVTLGTSASISCSSNKSLLHSNDITYLYWYLQRPGQSPQ LLIYRMSNLASGVPDRFSGSGSGTDFTLRISRVEAEDVGVYYCAQMLERP WTFGGGTKLEIK | 28 |
| 53H21A | QIVLTQSPALMSASPGEKVTMTCSASSSVSYMYWYQQKPRSSPKPWIYLT SNLASGVPARFSGSGSGTSYSLTISSMEAEDAATYYCQQWSSNPWTFGGG TKLEIK | 30 |
| 53I12A | DIQMTQTTSSLSASLGDRVTISCSASQGISNYLNWYQQKPDGTVKLLIYY TSSLHSGVPSRFSGSGSGTDYSLTISNLEPEDIATYYCQQYSKLPRTFGG GTKLEIK | 32 |
| 60A9A | DIVMTQSPSSLAMSVGQKVTMSCKSSQSLLNSSNQKNYLAWYQQKPGQSP KLLVYFASTRDSGVPDRFIGGGSGTDFTLTISSVQAEDLADYFCQQHYST PLTFGAGTKLELK | 34 |
| 39J9A | DIQMTQSPASLAASVGETVTITCRASENIYYSLAWYQQKQGKSPQLLIYN ADTLEDGVPSRFSGSGSGTQYSMKINSMQPEDTATYFCKQAYDVPLTFGA GTKLELK | 36 |
| 49H8A | QIVLTQSPALMSASPGEKVTMTCSASSSVSYMYWYQQKPRSSPKPWIYLT SNLASGVPARFSGSGSGTSYSLTISSMEAEDAATYYCQQWSSNPPTFGSG TKLEIK | 38 |
| 51B10A | DIKMTQSPSSMYASLGERVTITCKASQDINSYLSWFQQKPGKSPKTLIYR ANRLVDGVPSRFSGSGSGQDYSLTISSLEYEDMGIYYCLQYDEFPLTFGA GTKLELK | 40 |

VL: light chain variable region

TABLE 3

CDR regions 1-3 of heavy chain for anti-CD73 mAbs

| mAb | HC CDR1 | ID | HC CDR2 | ID | HC CDR3 | ID |
|---|---|---|---|---|---|---|
| 37C7A | GFSLSTFGMG | 41 | IWWDDDM | 42 | ARSPITTVVADY | 43 |
| 38C16A | GYTFSSYW | 44 | ILPGSGST | 45 | ARGDYFGSSYRGPY | 46 |
| 39G8A | GYTFTSYW | 47 | IDPSGGYT | 48 | ARNYYYGSSGTMDY | 49 |
| 43E8A | GYTFSNYW | 50 | ILPGNVIT | 51 | ARRGDDGYLYAMDY | 52 |
| 4613A | GYTFTDYY | 53 | IYPGSGNT | 54 | ARYWDYYGSTYGYFDV | 55 |
| 46O19A | GYTFTDYN | 56 | INPNNGGT | 57 | ARDYFWYFDV | 58 |
| 47H24A | GFSLTSYG | 59 | IWSGGST | 60 | ASQYVAY | 61 |
| 49O5A | GYTFTSYW | 62 | INPSNGGT | 63 | ARSKSNYGYYAMDY | 64 |
| 50B10A | GYTFTSYW | 65 | INPSNGRT | 66 | ARSEGRVYYDYFYAMDY | 67 |
| 50H17A | GYAFTNYL | 68 | INPGSGGT | 69 | ARDYYWYFDV | 70 |
| 50E16A | AIRDTNYW | 71 | IYPGNGDT | 72 | ATYYSNYGGAMDY | 73 |

TABLE 3-continued

CDR regions 1-3 of heavy chain for anti-CD73 mAbs

| mAb | HC CDR1 | ID | HC CDR2 | ID | HC CDR3 | ID |
|---|---|---|---|---|---|---|
| 50F1A | GYTFTDYS | 74 | INTETGEP | 75 | ARDIFWAMDY | 76 |
| 54I14A | GYTFTSYN | 77 | IYPGNGDT | 78 | ARYDYDAMDY | 79 |
| 52K11A | GYSFTGYN | 80 | INPYYGST | 81 | AGSSYVDYAMDY | 82 |
| 53H21A | GYTFTSYV | 83 | IIPYNDGT | 84 | ARWGNWDYFDY | 85 |
| 53I12A | GYTFTSYW | 86 | IYAGSSSS | 87 | ARSGHGYDGFAY | 88 |
| 60A9A | GYAFSSYW | 89 | IYPGDGDT | 90 | AREAIYYGNYVFTY | 91 |
| 39I9A | GYAFTNYL | 92 | INPGSGGT | 93 | ARRGDYYGNPFDY | 94 |
| 49H8A | GYTFTNYW | 95 | IDPSDNYT | 96 | ARGYYGYSPSWFAY | 97 |
| 51B10A | GYSFTGYY | 98 | INPYSGAT | 99 | ARSYYGAMDY | 100 |

HC: heavy chain;
CDR: complementarity determining region;
ID: SEQ ID NO
The HC CDRs for the anti-CD73 mAbs were determined utilizing the IMGT method (Lefranc, M.-P. et al., Nucleic Acids Res. 1999; 27:209-212).

TABLE 4

CDR regions 1-3 of light chain for anti-CD73 mAbs

| mAb | LC CDR1 | ID | LC CDR2 | ID | LC CDR3 | ID |
|---|---|---|---|---|---|---|
| 37C7A | QNLVHSYGNTY | 101 | KVS | 102 | SQNTHVPWT | 103 |
| 38C16A | QSLLDSDGRTY | 104 | LVS | 105 | WQGTHFPHT | 106 |
| 39G8A | QSLLNSSNQKNY | 107 | FAS | 108 | QQHYSTPYT | 109 |
| 43E8A | ESVDNYGISF | 110 | AAS | 111 | QQSKEVPFT | 112 |
| 46J3A | KNISKY | 113 | SGS | 114 | QQHNEYPFT | 115 |
| 46O19A | QSLLNSGNQKNY | 116 | WAS | 117 | QNDYSYPLT | 118 |
| 47H24A | QDIGSR | 119 | ATS | 120 | LQYASSPFT | 121 |
| 49O5A | DHIDNW | 122 | GAT | 123 | QQYWSSPFT | 124 |
| 50B10A | QDISNY | 125 | YTS | 126 | QQGNTLPWT | 127 |
| 50H17A | QSLLNSGNQKNY | 128 | WAS | 129 | QNDYSYPLT | 130 |
| 50E16A | QDVGTAVA | 131 | WAS | 132 | QQYSSYPYT | 133 |
| 50F1A | QSLLNSGNQKNY | 134 | WAS | 135 | QNDYSYPLT | 136 |
| 54I14A | ENIYSY | 137 | NAK | 138 | QHHYGTPFT | 139 |
| 52K11A | KSLLHSNDITY | 140 | RMS | 141 | AQMLERPWT | 142 |
| 53H21A | SSVSY | 143 | LTS | 144 | QQWSSNPWT | 145 |
| 53I12A | QGISNY | 146 | YTS | 147 | QQYSKLPRT | 148 |
| 60A9A | QSLLNSSNQKNY | 149 | FAS | 150 | QQHYSTPLT | 151 |
| 39I9A | ENIYYS | 152 | NAD | 153 | KQAYDVPLT | 154 |

TABLE 4-continued

CDR regions 1-3 of light chain for anti-CD73 mAbs

| mAb | LC CDR1 | ID | LC CDR2 | ID | LC CDR3 | ID |
|---|---|---|---|---|---|---|
| 49H8A | SSVSY | 155 | LTS | 156 | QQWSSNPPT | 157 |
| 51B10A | QDINSY | 158 | RAN | 159 | LQYDEFPLT | 160 |

LC: light chain;
CDR: complementarity determining region
The LC CDRs for the anti-CD73 mAbs were determined utilizing the IMGT method (Lefranc, M.-P. et al., Nucleic Acids Res. 1999; 27:209-212).

CDR regions 1-3 of heavy chain for anti-CD73 mAbs

| mAb | HC CDR1 | ID | HC CDR2 | ID | HC CDR3 | ID |
|---|---|---|---|---|---|---|
| 37C7A | GFSLSTFGMGVT | 161 | HIWWDDDMYYNPALKS | 162 | ARSPITTVVADY | 163 |
| 38C16A | GYTFSSYWIE | 164 | EILPGSGSTNYNEKFKG | 165 | ARGDYFGSSYRGPY | 166 |
| 39G8A | GYTFTSYWMH | 167 | EIDPSGGYTNYNQKFKG | 168 | ARNYYYGSSGTMDY | 169 |
| 43E8A | GYTFSNYWIE | 170 | EILPGNVITNYNEKFKG | 171 | ARRGDDGYLYAMDY | 172 |
| 46J3A | GYTFTDYYMH | 173 | EIYPGSGNTYYNEKFKG | 174 | ARYWDYYGSTYGYFDV | 175 |
| 46O19A | GYTFTDYNMH | 176 | YINPNNGGTSYNQKFKG | 177 | ARDYFWYFDV | 178 |
| 47H24A | GFSLTSYGVH | 179 | VIWSGGSTDYNAAFISR | 180 | ASQYVAY | 181 |
| 49O5A | GYTFTSYWMH | 182 | NINPSNGGTNYNEKFKS | 183 | ARSKSNYGYYAMDY | 184 |
| 50B10A | GYTFTSYWMH | 185 | EINPSNGRTNYNEKFKS | 186 | ARSEGRVYYDYFYAMDY | 187 |
| 50H17A | GYAFTNYLIE | 188 | VINPGSGGTNYNEKFKG | 189 | ARDYWYFDV | 190 |
| 50E16A | AIRDTNYWMQ | 191 | AIYPGNGDTSYNQKFKV | 192 | ATYYSNYGGAMDY | 193 |
| 50F1A | GYTFTDYSMH | 194 | WINTETGEPTYADDFKG | 195 | ARDIFWAMDY | 196 |
| 54I14A | GYTFTSYNMH | 197 | AIYPGNGDTSYNQKFKG | 198 | ARYDYDAMDY | 199 |
| 52K11A | GYSFTGYNMN | 200 | NINPYYGSTSYNQKFKG | 201 | AGSSYVDYAMDY | 202 |
| 53H21A | GYTFTSYVMH | 203 | YIIPYNDGTKYNEKFEG | 204 | ARWGNWDYFDY | 205 |
| 53I12A | GYTFTSYWIN | 206 | NIYAGSSSSNYNEKFKS | 207 | ARSGHGYDGFAY | 208 |
| 60A9A | GYAFSSYWMN | 209 | QIYPGDGDTYYSGKFKG | 210 | AREAIYYGNYVFTY | 211 |
| 39J9A | GYAFTNYLIE | 212 | LINPGSGGTNYIEKFKG | 213 | ARRGDYYGNPFDY | 214 |
| 49H8A | GYTFTNYWMQ | 215 | EIDPSDNYTHYNQKFKG | 216 | ARGYYGYSPSWFAY | 217 |
| 51B10A | GYSFTGYYMH | 218 | RINPYSGATNSNQNFKD | 219 | ARSYYGAMDY | 220 |

HC: heavy chain;
CDR: complementarity determining region
The HC CDRs for the anti-CD73 mAbs were determined utilizing a combination of IMGT (Lefranc, M.-P. et al., Nucleic Acids Res. 1999; 27:209-212) and Kabat (Elvin A. Kabat et al., Sequences of Proteins of Immunological Interest 5th ed. (1991)) methods.

TABLE 6

CDR regions 1-3 of light chain for anti-CD73 mAbs

| mAb | LC CDR1 | ID | LC CDR2 | ID | LC CDR3 | ID |
|---|---|---|---|---|---|---|
| 37C7A | RSSQNLVHSYGNTYLH | 221 | KVSNRFS | 222 | SQNTHVPWT | 223 |
| 38C16A | KSSQSLLDSDGRTYLN | 224 | LVSKLDS | 225 | WQGTHFPHT | 226 |

TABLE 6-continued

CDR regions 1-3 of light chain for anti-CD73 mAbs

| mAb | LC CDR1 | ID | LC CDR2 | ID | LC CDR3 | ID |
|---|---|---|---|---|---|---|
| 39G8A | KSSQSLLNSSNQKNYLA | 227 | FASTRES | 228 | QQHYSTPYT | 229 |
| 43E8A | RASESVDNYGISFMN | 230 | AASNQGS | 231 | QQSKEVPFT | 232 |
| 46J3A | RASKNISKYLA | 233 | SGSTLQS | 234 | QQHNEYPFT | 235 |
| 46O19A | KSSQSLLNSGNQKNYLT | 236 | WASTRES | 237 | QNDYSYPLT | 238 |
| 47H24A | RASQDIGSRLT | 239 | ATSSLDS | 240 | LQYASSPFT | 241 |
| 49O5A | EASDHIDNWLA | 242 | GATSLET | 243 | QQYWSSPFT | 244 |
| 50B10A | RASQDISNYLN | 245 | YTSRLHS | 246 | QQGNTLPWT | 247 |
| 50H17A | KSSQSLLNSGNQKNYLT | 248 | WASTRES | 249 | QNDYSYPLT | 250 |
| 50E16A | KASQDVGTAVA | 251 | WASTRHT | 252 | QQYSSYPYT | 253 |
| 50F1A | KSSQSLLNSGNQKNYLT | 254 | WASTRES | 255 | QNDYSYPLT | 256 |
| 54I14A | RASENIYSYFA | 257 | NAKTLAE | 258 | QHHYGTPFT | 259 |
| 52K11A | SSNKSLLHSNDITYLY | 260 | RMSNLAS | 261 | AQMLERPWT | 262 |
| 53H21A | SASSSVSYMY | 263 | LTSNLAS | 264 | QQWSSNPWT | 265 |
| 53I12A | SASQGISNYLN | 266 | YTSSLHS | 267 | QQYSKLPRT | 268 |
| 60A9A | KSSQSLLNSSNQKNYLA | 269 | FASTRDS | 270 | QQHYSTPLT | 271 |
| 39J9A | RASENIYYSLA | 272 | NADTLED | 273 | KQAYDVPLT | 274 |
| 49H8A | SASSSVSYMY | 275 | LTSNLAS | 276 | QQWSSNPPT | 277 |
| 51B10A | KASQDINSYLS | 278 | RANRLVD | 279 | LQYDEFPLT | 280 |

LC: light chain;
CDR: complementarity determining region
The LC CDRs for the anti-CD73 mAbs were determined utilizing a combination of IMGT (Lefranc, M.-P. et al., Nucleic Acids Res. 1999; 27:209-212) and Kabat (Elvin A. Kabat et al., Sequences of Proteins of Immunological Interest 5th ed. (1991)) methods.

Example 2: Production and Purification of mAbs from Culture Media of Transfected 293E Cells To obtain the recombinant anti-CD73 chimeric mAbs, the expression vectors containing the mouse variable regions (VH and VL) fused to the constant regions of human IgG1 heavy chain with LALA mutations (L234A/L235A) and kappa light chain, respectively, were transiently transfected into 293E cells. The recombinant antibodies produced in the suspension of the 293E cells were purified using Protein A affinity chromatography.

Figure 1B:
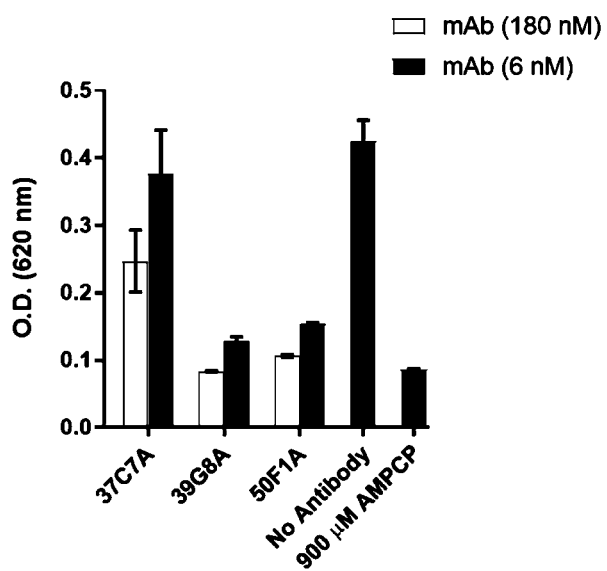
Figure 2A:
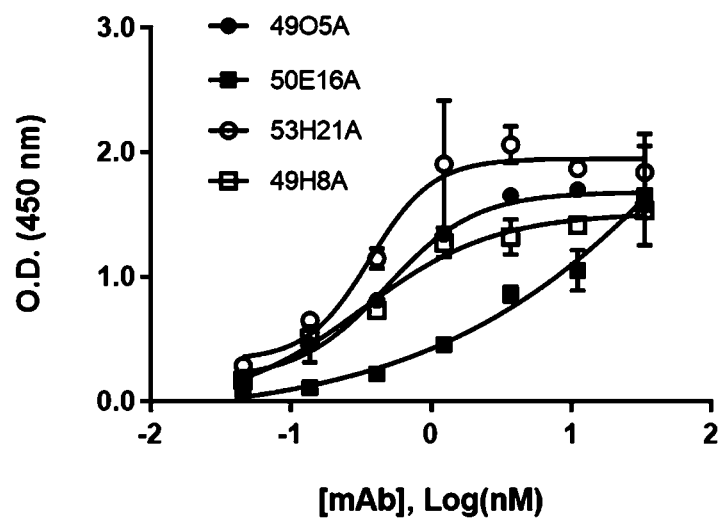
FIGS. 2A-2E show the binding of chimeric anti-CD73 mAbs to human CD73 in an ELISA assay.
Figure 2B:
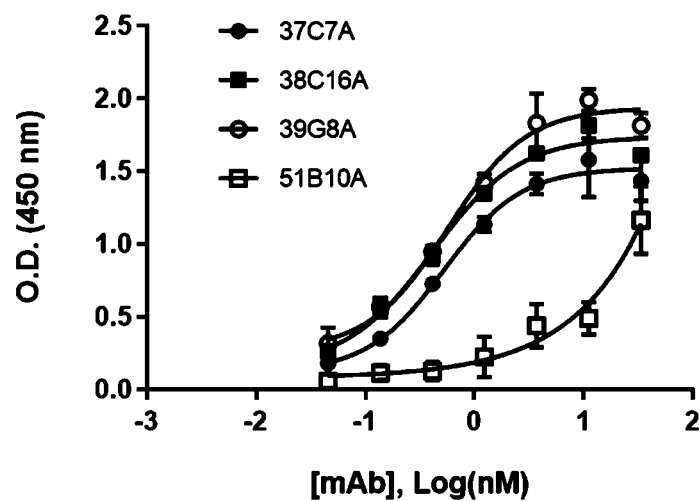
Figure 2C:
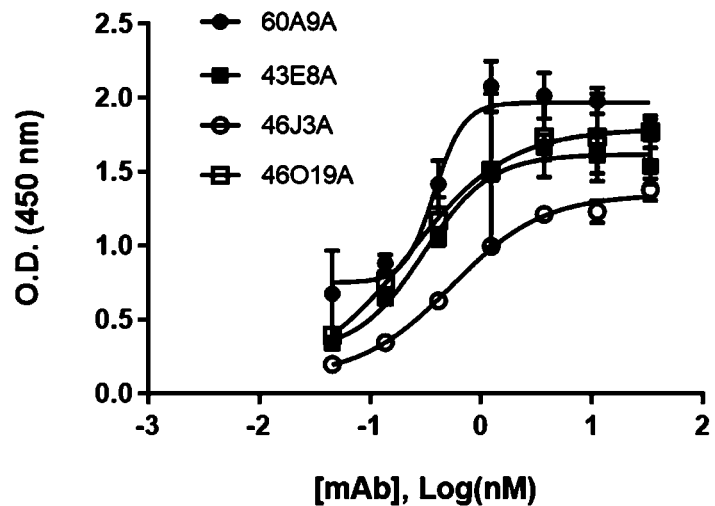
Figure 2D:
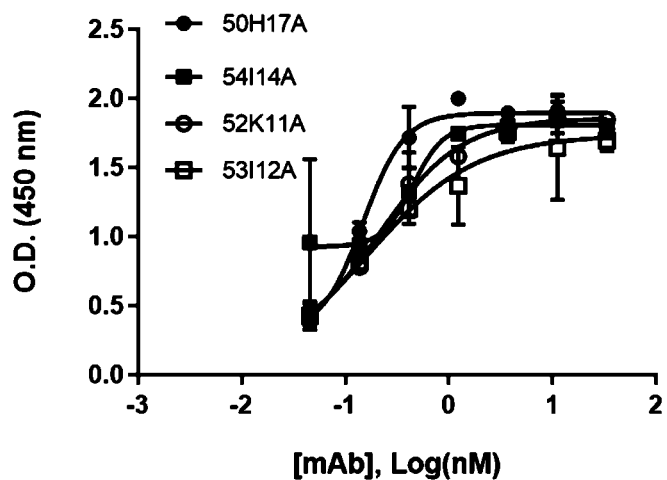
Figure 2E:
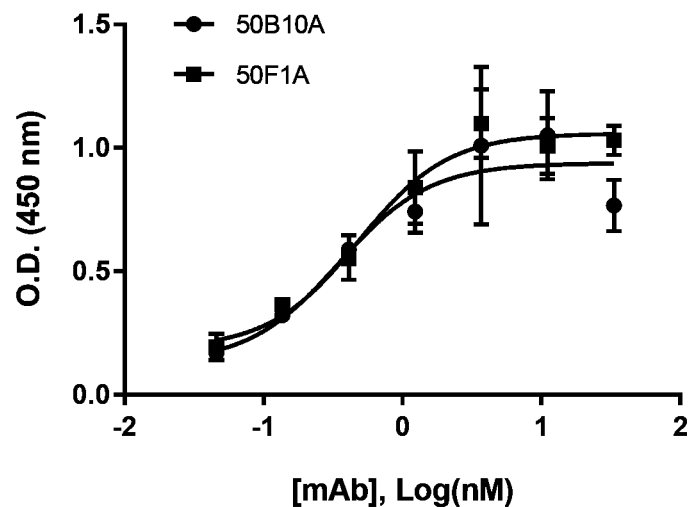

Example 3: Inhibition of the Nucleotidase Activity of Immobilized CD73 by Purified Anti-CD73 Chimeric mAbs HIS-tagged human CD73 (huCD73-HIS, 60 μL/well at 0.15 μg/mL) in assay buffer (25 mM Tris-HCl, pH7.5, and 5 mM MgCl$_2$) was coated on nickel coated plates (ThermoFisher Scientific, Cat #: 15242) at 4° C. overnight. After washing, anti-CD73 chimeric mAbs were added and incubated at room temperature for 1 hour. The enzymatic reaction measuring the nucleotidase activity of CD73 was initiated by adding 100 μM AMP to the plate. The reaction proceeded for 20 min at 37° C. The free phosphate was detected and quantified by Malachite Green Phosphate Detection Kit (R&D Systems, Cat #: DY996). Inhibition of the nucleotidase activity of immobilized CD73 by anti-CD73 chimeric mAbs is shown in FIGS. 1A and 1B. No Antibody, enzyme reaction with no inhibitor; AMPCP (adenosine 5'(α, β-methylene)diphosphate) was used as a control for inhibition of enzyme activity.

Example 4: ELISA Binding Assay with Chimeric mAbs

HIS-tagged human CD73 (huCD73-HIS, 50 μL/well at 5 μg/mL (85 nM)) (BPS Bioscience, Cat #: 71184) in carbonate coating buffer was coated on an ELISA plate at 4° C. overnight. After washing by TBST buffer (TBS buffer with 0.05% Tween 20), the ELISA plate was blocked by 5% BSA in TBST at room temperature for 1 hour and washed again. Chimeric anti-CD73 antibodies were added, mixed and incubated for 1 hour at room temperature. The plate was washed and the binding of anti-CD73 antibodies to the immobilized huCD73-HIS was detected by adding anti-human IgG conjugated to horseradish peroxidase (anti-hIgG-HRP) (ThermoFisher Scientific, Cat #: H10007) and incubating for 1 hour. The plate was washed, and the ELISA was developed using One-step Detection Solution (ThermoFisher Scientific, Cat #: 34029) and measured as the absorbance at 450 nm. The results for the binding of anti-CD73 mAbs to CD73 are shown in FIGS. 2A-2E.

Figure 3:
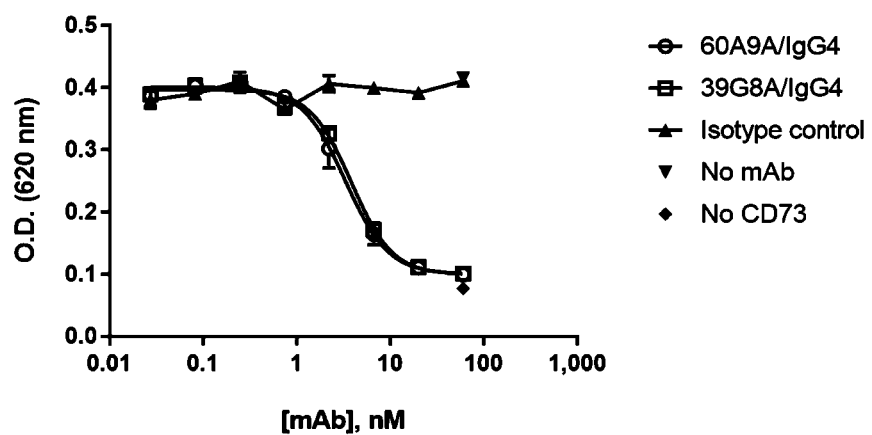
FIG. 3 shows the inhibition of the nucleotidase activity of soluble human CD73 by chimeric mAbs 60A9A/IgG4 and 39G8A/IgG4. No mAb, enzyme reaction with no antibody added; No CD73, negative control reaction with neither antibody nor CD73 added.

Example 5: Inhibition of the Nucleotidase Activity of Soluble CD73 by Anti-CD73 mAbs This assay was carried out using recombinant human CD73 in solution rather than immobilized on a plate. HIS-tagged human CD73 (huCD73-HIS) (BPS Bioscience, Cat #: 71184) at final concentration of 0.5 nM and various concentrations of anti-CD73 antibodies were incubated in assay buffer (25 mM Tris-HCl, pH7.5, 5 mM $MgCl_2$, 140 mM NaCl, and 0.1% BSA) for 20 minutes at 37° C. The enzymatic reaction was initiated by adding AMP (Sigma Aldrich, Cat #: A2252) to the final concentration of 400 µM. After incubating the plate at 37° C. for 20 min, the concentration of inorganic phosphate was determined by Malachite Green Phosphate Detection Kit (R&D Systems, Cat #: DY996). Two chimeric anti-CD73 mAbs 60A9A/IgG4 and 39G8A/IgG4 were made by fusing the VH and VL regions of mouse mAbs 60A9A and 39G8A to the constant regions of human IgG4 heavy chain and kappa light chain, respectively. The chimeric antibodies were expressed in CHO cells and purified using Protein A affinity chromatography and tested in this assay. The results for the inhibition of the nucleotidase activity of soluble CD73 by 60A9A/IgG4 and 39G8A/IgG4 are shown in FIG. 3.

Example 6: Humanization of Anti-CD73 mAbs

The mouse anti-CD73 mAbs 60A9A and 39G8A were humanized to reduce the potential of immunogenicity when used in human patients. The sequences of the variable regions of the heavy and light chains (VH and VL) were compared with the human antibody sequences in the Protein Data Bank (PDB) database and homology models were built. The CDRs in both the heavy and light chains of the mouse mAbs were grafted into human frameworks that have the highest possibility of maintaining the proper structure likely required for antigen binding. The sequences of the humanized VH and VL regions are shown in Tables 7 and 8.

The humanized VH and VL regions were fused to the constant regions of human IgG1 heavy chain with LALA mutations (L234A/L235A) and kappa light chain, respectively. Constructs corresponding to the mAb sequences were used for transient transfection in 293E cells and the humanized mAbs were purified using Protein A chromatography. The humanized mAbs were tested in an enzyme activity assay with soluble human CD73. In this assay, 0.4 nM huCD73 was incubated with the mAbs for 1 hour on ice before the enzyme reaction was initiated by adding AMP to a final concentration of 100 µM. The IC50 values for the humanized mAbs are shown in Table 9.

Figure 4A:
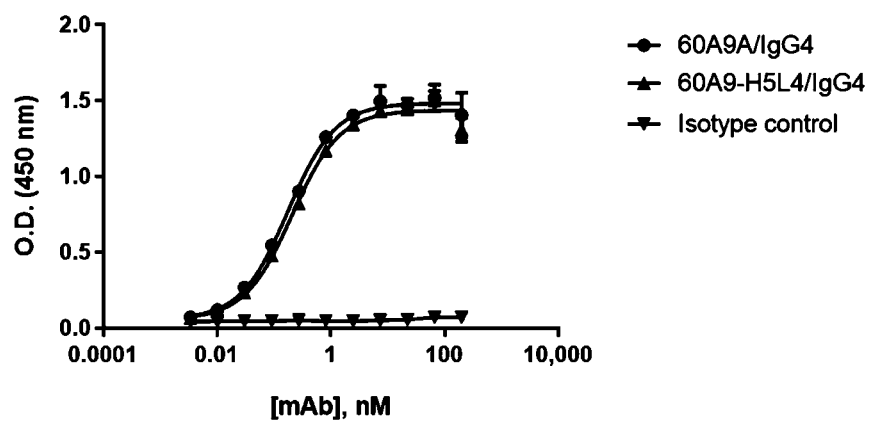
FIGS. 4A-4D show the binding to human CD73 and inhibition of nucleotidase activity of human CD73 by the humanized mAb 60A9-H5L4/IgG4.
Figure 4B:
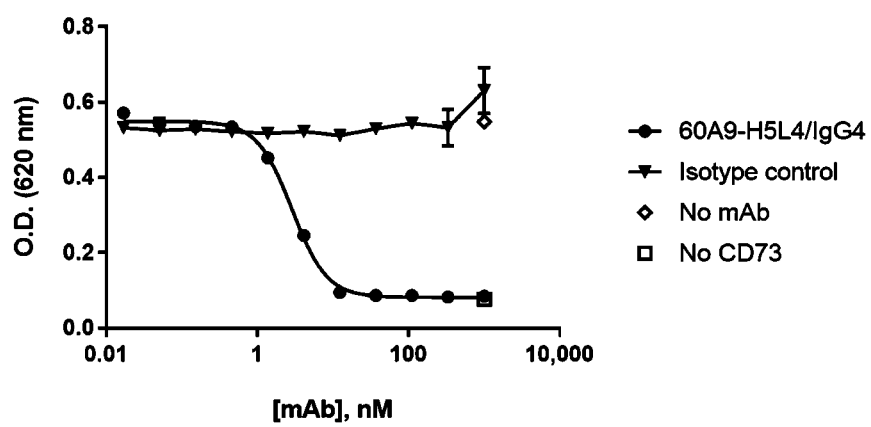

Humanized mAb 60A9-H5L4 on human IgG4/kappa backbone (60A9-H5L4/IgG4) was analyzed in the ELISA binding assay; the IgG4 chimeric version of 60A9A (60A9A/IgG4) was used as control. The ELISA binding result is shown in FIG. 4A. 60A9-H5L4/IgG4 was also analyzed for its ability to inhibit the nucleotidase activity of soluble CD73 under the conditions in Example 5. The result is shown in FIG. 4B.

TABLE 7

Sequences of humanized heavy chain variable regions for anti-CD73 mAbs

| VH | Sequence | ID |
|---|---|---|
| 60A9-H1 | EVQLVESGGGLVQPGQSLKLSCKASGYAFSSYWMNWVRQAPGKGLEWMGQ IYPGDGDTYYNPSVKGRFTISADTSKNTAYLQLNNLRAEDTAVYYCAREA IYYGNYVFTYWGQGTLVTVSS | 282 |
| 60A9-H2 | EVQLVESGGGLVQPGGSLRLSCKASGYAFSSYWMNWVRQAPGKGLEWVGQ IYPGDGDTYYNPSVKGRFTISADTSKNTLYLQMNSLRAEDTAVYYCAREA IYYGNYVFTYWGQGTLVTVSS | 283 |
| 60A9-H3 | EVQLVESGGGLVQPGQSLKLSCKASGYAFSSYWMNWVRQAPGKGLEWIGQ IYPGDGDTYYNPSVKGRATLSADKSKNTAYLQLNNLRAEDTAVYYCAREA IYYGNYVFTYWGQGTLVTVSS | 284 |
| 60A9-H4 | EVQLVESGGGLVQPGQSLKLSCKASGYAFSSYWMNWVRQAPGKGLEWIGQ IYPGDGDTYYSGSVKGRATLSADKSKNTAYLQLNNLRAEDTAVYYCAREA IYYGNYVFTYWGQGTLVTVSS | 285 |
| 60A9-H5 | EVQLVESGGGLVQPGQSLKLSCKASGYAFSSYWMNWVKQRPGKGLEWIGQ IYPGDGDTYYSGKFKGRATLSADKSKNTAYLQLNNLRAEDTAVYYCAREA IYYGNYVFTYWGQGTLVTVSS | 286 |
| 60A9-H6 | QVQLVQSGAEVKRPGSSVTVSCKASGYAFSSYWMNWVRQAPGRGLEWIGQ IYPGDGDTYYAPRFQGRATLTADKSTSTAYLELNSLRPEDTAVYFCAREA IYYGNYVFTYWGQGTLVTVSS | 295 |
| 60A9-H7 | QVQLVQSGAEVKKPGSSVTVSCKASGYAFSSYWMNWVRQAPGRGLEWIGQ IYPGDGDTYYAPKFQGRATLTADKSTSTAYMELSSLRSEDTAVYFCAREA IYYGNYVFTYWGQGTLVTVSS | 296 |
| 60A9-H8 | QVQLVQSGAEVKKPGSSVTVSCKASGYAFSSYWMNWVRQAPGRGLEWIGQ IYPGDGDTYYSGKFQGRATLTADKSTSTAYMELSSLRSEDTAVYFCAREA IYYGNYVFTYWGQGTLVTVSS | 297 |
| 60A9-H9 | QVQLVQSGAEVKRPGSSVTVSCKASGYAFSSYWMNWVRQAPGRGLEWIGQ IYPGDGDTYYSGKFKGRATLSADKSKNTAYLQLNNLRAEDTAVYYCAREA IYYGNYVFTYWGQGTLVTVSS | 298 |

TABLE 7-continued

Sequences of humanized heavy chain variable regions for anti-CD73 mAbs

| VH | Sequence | ID |
|---|---|---|
| 39G8-H1 | QVQLVQSGAEVKKPGASVKVSCKASGYTFTSYWMHWVRQAPGQGLEWIGE IDPSGGYTNYAQKFQGRSTLTVDKSISTAYMELSRLRSDDTAVYYCARNY YYGSSGTMDYWGQGTLVTVSS | 287 |
| 39G8-H2 | QVQLVQSGAEVKKPGASVKVSCKASGYTFTSYWMHWVRQAPGQGLEWIGE IDPSGGYTNYAQKFQGRSTLTVDTSISTAYMELSRLRSDDTAVYYCARNY YYGSSGTMDYWGQGTLVTVSS | 288 |
| 39G8-H3 | QVQLVQSGAEVKKPGASVKVSCKASGYTFTSYWMHWVRQAPGQGLEWIGE IDPSGGYTNYNQKFQGRSTLTVDKSISTAYMELSRLRSDDTAVYYCARNY YYGSSGTMDYWGQGTLVTVSS | 289 |

TABLE 8

Sequences of humanized light chain variable regions for anti-CD73 mAbs

| VL | Sequence | ID |
|---|---|---|
| 60A9-L1 | DIQMTQSPSSLLSASLGDRVTITCKSSQSLLNSSNQKNYLAWYQQKPGQSP KLLIYFASTRDSGVPDRFSGSGSGTDFTLTISSLEPEDFATYYCQQHYST PLTFGGGTKLEIK | 290 |
| 60A9-L2 | DIVMTQSPSSLSASLGDRVTITCKSSQSLLNSSNQKNYLAWYQQKPGQSP KLLIYFASTRDSGVPDRFSGSGSGTDFTLTISSLEPEDFATYYCQQHYST PLTFGGGTKLEIK | 291 |
| 60A9-L3 | DIQMTQSPSSLLSASLGDRVTITCKSSQSLLNSSNQKNYLAWYQQKPGQSP KLLVYFASTRDSGVPDRFSGSGSGTDFTLTISSLEPEDFATYYCQQHYST PLTFGGGTKLEIK | 292 |
| 60A9-L4 | DIVMTQSPSLLSASLGDRVTISCKSSQSLLNSSNQKNYLAWYQQKPGQSP KLLVYFASTRDSGVPDRFSGSGSGTDFTLTISSLEPEDFATYFCQQHYST PLTFGAGTKLEIK | 293 |
| 60A9-L5 | EIVMTQSPGTQSLSPGERATLSCKSSQSLLNSSNQKNYLAWYQQRPGQAP RLLVYFASTRDSGVADRFSGSGSGTDFTLTISRLEPEDFAVYFCQQHYST PLTFGQGTKVEVK | 299 |
| 39G8-L3 | DIVMTQSPDSLAVSLGERATMSCKSSQSLLNSSNQKNYLAWYQQKPGQPP KLLVYFASTRESGVPDRFSGSGSGTDFTLTISSLQAEDVAVYFCQQHYST PYTFGGGTKVEIK | 294 |

TABLE 9

IC50 values for humanized mAbs in huCD73 enzymatic assay in solution

| Name | IC50 (nM) |
|---|---|
| 60A9-H1L1 | 3.34 |
| 60A9-H1L2 | 6.17 |
| 60A9-H1L3 | 4.96 |
| 60A9-H2L1 | 4.13 |
| 60A9-H2L2 | 11.20 |
| 60A9-H2L3 | 4.57 |
| 60A9-H3L1 | 2.94 |
| 60A9-H3L2 | 4.97 |
| 60A9-H3L3 | 2.09 |
| 60A9-H4L1 | 3.10 |
| 60A9-H4L2 | 4.97 |
| 60A9-H4L3 | 2.74 |

The name 60A9-H1L1 refers to the mAb constructed using VH 60A9-H1 and VL 60A9-L1.
All the other humanized mAbs adopt the same naming rule.

Example 7: Inhibition of the Nucleotidase Activity of Cell Surface CD73 by Anti-CD73 mAbs A375 cells were harvested with PBS-EDTA (2 mM EDTA in PBS) and washed twice in PBS buffer supplemented with 0.1% BSA. 100,000 cells were plated in the presence of various concentrations of anti-CD73 antibodies and incubated for 20 min at 37° C. AMP was then added to the final concentration of 125 µM (Sigma Aldrich, Cat #: A2252) in a final volume of 60 µL and the reaction was kept at 37° C. for 60 min. Plates were then centrifuged and 40 µL of supernatant was transferred to a new plate. ATP (Sigma Aldrich, Cat #: A9187) was added to make the final concentration of 100 µM in a final volume of 50 µL and the mixture was incubated at 37° C. for 15 min. CellTiter-Glo® 2.0 reagent (Promega, Cat #: G9242) was added in a 1:1 ratio to determine the AMP level in the mixture and the enzyme activity in a given reaction was calculated based on the AMP concentration at the end of reaction. The results for the inhibition of CD73 activity by the humanized anti-CD73 mAbs (on human IgG1 LALA/kappa backbone) in the cell-based assay are shown in Table 10.

Figure 4C:
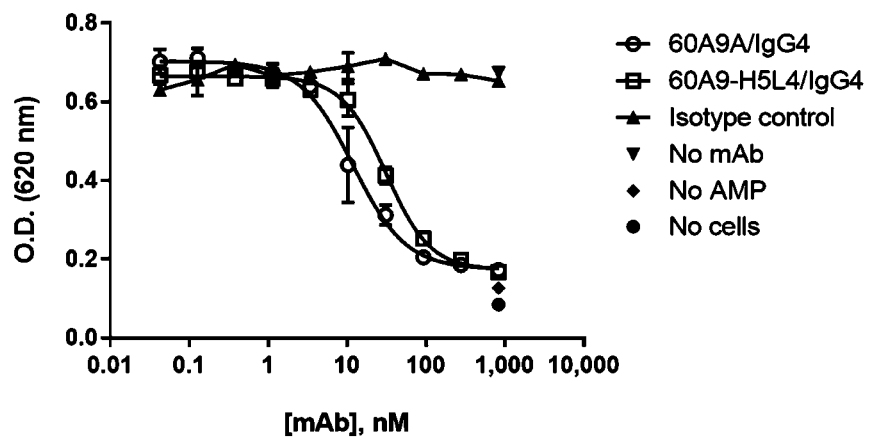
Figure 4D:
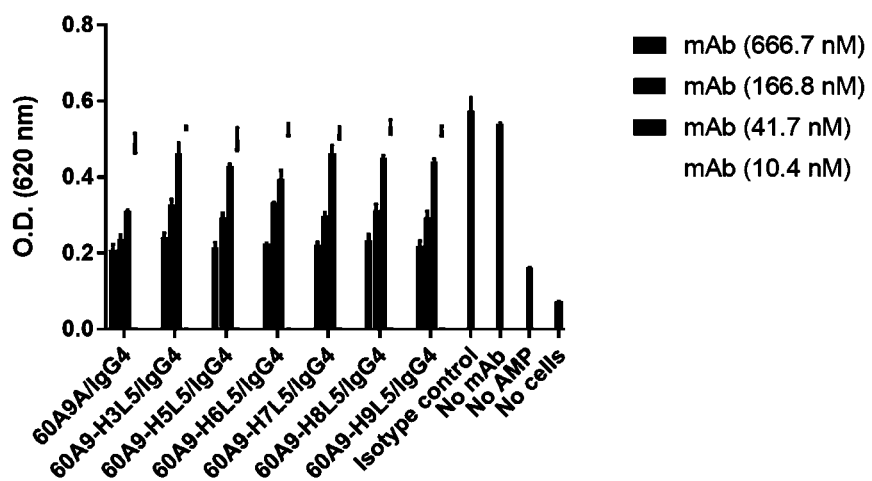

Humanized anti-CD73 mAb 60A9-H5L4/IgG4, 60A9-H3L5/IgG4, 60A9-H5L5/IgG4, 60A9-H6L5/IgG4, 60A9-H7L5/IgG4, 60A9-H8L5/IgG4 and 60A9-H9L5/IgG4 were also tested in a cell-based assay using a phosphate detection method. In this assay, 50,000 A375 cells were washed and plated in assay buffer (25 mM Tris-HCl, pH7.5, 5 mM MgCl$_2$, 140 mM NaCl, and 0.1% BSA) and the enzyme reaction with a final AMP concentration of 400 µM lasted 20 min at 37° C. Free phosphate produced by the hydrolysis of AMP was quantified using Malachite Green Phosphate Detection Kit (R&D Systems, Cat #: DY996). The assay results are shown in FIGS. 4C and 4D.

TABLE 10

IC50 values for humanized mAbs in cell-based CD73 activity assay

| Name | IC50 (nM) |
|---|---|
| 60A9-H2L4 | 46.03 |
| 60A9-H3L4 | 133.67 |
| 60A9-H3L3 | 65.65 |
| 60A9-H4L4 | 134.67 |
| 60A9-H5L1 | 61.02 |
| 60A9-H5L2 | 57.31 |
| 60A9-H5L3 | 36.41 |
| 60A9-H5L4 | 30.12 |
| 39G8-H1L3 | 49.62 |
| 39G8-H2L3 | 66.33 |
| 39G8-H3L3 | 56.12 |

Example 8: Inhibition of the Nucleotidase Activity of CD73 in Patient Serum Samples by Anti-CD73 mAbs Serum samples from patients with colorectal cancer were used to assess the inhibitory activity of the humanized anti-CD73 mAb 60A9-H5L4/IgG4. 20 µL of serum and 10 µL of the anti-CD73 mAb in PBS buffer supplemented with 0.1% BSA were incubated at 37° C. for 30 min. 10 µL of 500 µM AMP (Sigma Aldrich, Cat #: A2252) was added and the reaction mixture was incubated at 37° C. for 30 min. ATP (Sigma Aldrich, Cat #: A9187) was then added to the final concentration of 100 µM. 25 µL of the reaction mixture was transferred to a white half-area 96-well plate. CellTiter-Glo® 2.0 reagent (Promega, Cat #: G9242) was added in a 1:1 ratio to the mixture and the residual AMP level was determined by measuring its inhibitory effect on ATP detection. Samples containing 100 µM AMP and 100 µM ATP were used to establish assay background and samples containing only 100 µM ATP were used as positive control.

Figure 5:
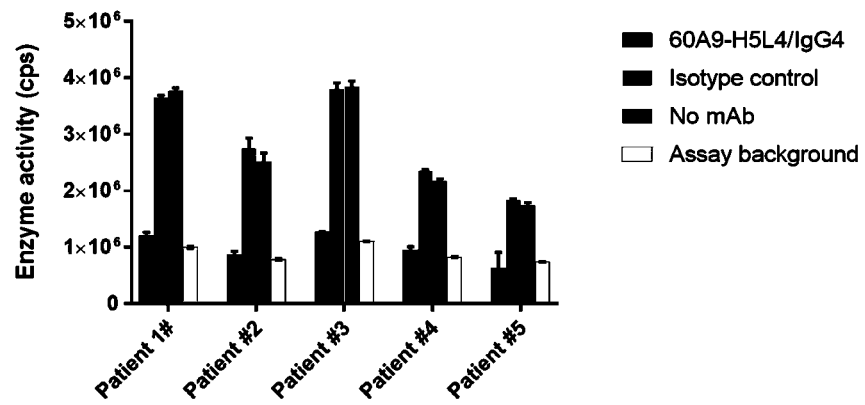
FIG. 5 shows the inhibition of the nucleotidase activity of CD73 in patient serum samples by humanized anti-CD73 mAb 60A9-H5L4/IgG4. No mAb, enzyme reaction with no antibody added; Assay background, enzyme reaction with 100 µM AMP and 100 µM ATP added; cps, counts/second.

The inhibition of the nucleotidase activity of CD73 in patient serum samples by humanized anti-CD73 mAb 60A9-H5L4/IgG4 was analyzed at 1000 nM. The results are shown in FIG. 5.

Example 9: Activation of T Cell Proliferation by Humanized Anti-CD73 mAb 60A9-H5L4/IgG4

Figure 6:
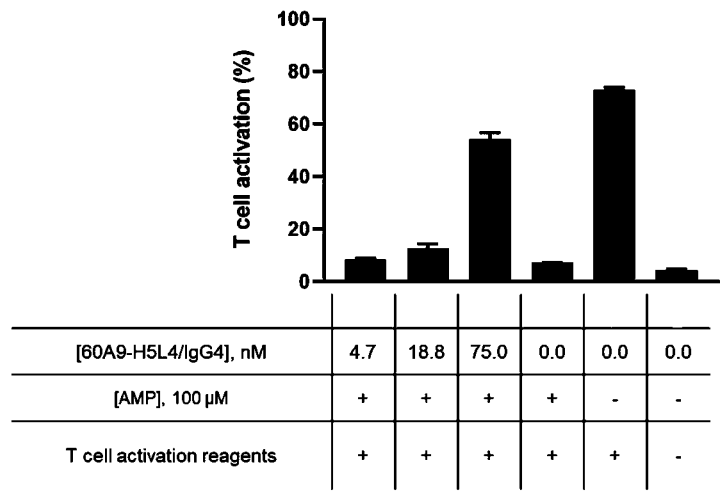
FIG. 6 shows the activation of T cell proliferation by humanized anti-CD73 mAb 60A9-H5L4/IgG4.

Primary human CD4+ T cells were isolated from frozen peripheral blood mononuclear cells using CD4+ T cell isolation kit (Miltenyi Biotec, Cat #: 130-096-533). Isolated CD4+ T cells at a density of 1,000,000 cells per mL in DPBS were labeled using CellTrace™ CFSE cell proliferation kit (Invitrogen, Cat #: C34554) at 37° C. for 30 min. Cells were washed three times with cold DPBS and resuspended in AIM V media (Gibco, Cat #: 12055083). 100,000 cells per well were pre-incubated with various concentrations of 60A9-H5L4/IgG4 for 1 hour at 37° C. T cells were activated by the addition of T cell activation reagents, a combination of Dynabeads human T-activator CD3/CD28 (Gibco, Cat #: 11131D) at 1:1 bead-to-cell ratio and human IL-2 to the final concentration of 60 IU/mL. Thereafter, AMP (Sigma Aldrich, Cat #: A2252) was added to the final concentration of 100 µM. After 72 hours of incubation at 37° C., cells were stained with PE/Cy7 anti-human CD4 antibody (BioLegend, Cat #: 357409). Both PE/Cy7 and CFSE signals were analyzed on a Attune NxT flow cytometer. For the assay window, CFSE CD4+ cells in the absence of the T cell activation reagents had undergone no cell divisions and therefore were used to define the baseline while activated CFSE CD4+ cells (treated with the T cell activation reagents) in the absence of AMP had undergone uninhibited cell division and therefore were used to define the maximum proliferation. The effect of 60A9-H5L4/IgG4 on the activation of T cell proliferation is shown in FIG. 6. The cells treated with AMP were suppressed as expected, presumably due to the production of adenosine by cell surface CD73, and the addition of the anti-CD73 mAb 60A9-H5L4/IgG4 at 75 nM activated the cells, suggesting the mAb has functional activity in T cell activation.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

It is claimed:

1. An isolated monoclonal antibody or antigen-binding fragment thereof comprising a heavy chain complementarity determining region 1 (HCDR1), HCDR2, and HCDR3, a light chain complementarity determining region 1 (LCDR1), LCDR2, and LCDR3, having the polypeptide sequences of:

a. SEQ ID NOs:89, 90, 91, 149, 150 and 151, respectively, or SEQ ID NOs:209, 210, 211, 269, 270 and 271, respectively;

b. SEQ ID NOs:41, 42, 43, 101, 102 and 103, respectively, or SEQ ID NOs:161, 162, 163, 221, 222 and 223, respectively;

c. SEQ ID NOs:44, 45, 46, 104, 105 and 106, respectively, or SEQ ID NOs:164, 165, 166, 224, 225 and 226, respectively;

d. SEQ ID NOs:47, 48, 49, 107, 108 and 109, respectively, or SEQ ID NOs:167, 168, 169, 227, 228 and 229, respectively;

e. SEQ ID NOs:50, 51, 52, 110, 111 and 112, respectively, or SEQ ID NOs:170, 171, 172, 230, 231 and 232, respectively;

f. SEQ ID NOs:53, 54, 55, 113, 114 and 115, respectively, or SEQ ID NOs:173, 174, 175, 233, 234 and 235, respectively;

g. SEQ ID NOs:56, 57, 58, 116, 117 and 118, respectively, or SEQ ID NOs:176, 177, 178, 236, 237 and 238, respectively;

h. SEQ ID NOs:59, 60, 61, 119, 120 and 121, respectively, or SEQ ID NOs:179, 180, 181, 239, 240 and 241, respectively;

i. SEQ ID NOs:62, 63, 64, 122, 123 and 124, respectively, or SEQ ID NOs:182, 183, 184, 242, 243 and 244, respectively;

j. SEQ ID NOs:65, 66, 67, 125, 126 and 127, respectively, or SEQ ID NOs:185, 186, 187, 245, 246 and 247, respectively;

k. SEQ ID NOs:68, 69, 70, 128, 129 and 130, respectively, or SEQ ID NOs:188, 189, 190, 248, 249 and 250, respectively;

l. SEQ ID NOs:71, 72, 73, 131, 132 and 133, respectively, or SEQ ID NOs:191, 192, 193, 251, 252 and 253, respectively;

m. SEQ ID NOs:74, 75, 76, 134, 135 and 136, respectively, or SEQ ID NOs:194, 195, 196, 254, 255 and 256, respectively;
n. SEQ ID NOs:77, 78, 79, 137, 138 and 139, respectively, or SEQ ID NOs:197, 198, 199, 257, 258 and 259, respectively;
o. SEQ ID NOs:80, 81, 82, 140, 141 and 142, respectively, or SEQ ID NOs:200, 201, 202, 260, 261 and 262, respectively;
p. SEQ ID NOs:83, 84, 85, 143, 144 and 145, respectively, or SEQ ID NOs:203, 204, 205, 263, 264 and 265, respectively;
q. SEQ ID NOs:86, 87, 88, 146, 147 and 148, respectively, or SEQ ID NOs:206, 207, 208, 266, 267 and 268, respectively;
r. SEQ ID NOs:92, 93, 94, 152, 153 and 154, respectively, or SEQ ID NOs:212, 213, 214, 272, 273 and 274, respectively;
s. SEQ ID NOs:95, 96, 97, 155, 156 and 157, respectively, or SEQ ID NOs:215, 216, 217, 275, 276 and 277, respectively; or
t. SEQ ID NOs:98, 99, 100, 158, 159 and 160, respectively, or SEQ ID NOs:218, 219, 220, 278, 279 and 280, respectively;

wherein the antibody or antigen-binding fragment thereof specifically binds to CD73.

2. The isolated monoclonal antibody or antigen-binding fragment thereof of claim 1, comprising a heavy chain variable region having a polypeptide sequence at least 95% identical to SEQ ID NO:286 33, 1, 3, 5, 7, 9, 11, 13, 15, 17, 19, 21, 23, 25, 27, 29, 31, 35, 37, 39, 282, 283, 284, 285, 287, 288, 289, 295, 296, 297, or 298, or a light chain variable region having a polypeptide sequence at least 95% identical to SEQ ID NO:293 34, 2, 4, 6, 8, 10, 12, 14, 16, 18, 20, 22, 24, 26, 28, 30, 32, 36, 38, 40, 290, 291, 292, 294, or 299.

3. The isolated monoclonal antibody or antigen-binding fragment thereof of claim 1, comprising:
a. a heavy chain variable region having the polypeptide sequence of SEQ ID NO:286, and a light chain variable region having the polypeptide sequence of SEQ ID NO:293;
b. a heavy chain variable region having the polypeptide sequence of SEQ ID NO:33, and a light chain variable region having the polypeptide sequence of SEQ ID NO:34;
c. a heavy chain variable region having the polypeptide sequence of SEQ ID NO:1, and a light chain variable region having the polypeptide sequence of SEQ ID NO:2;
d. a heavy chain variable region having the polypeptide sequence of SEQ ID NO:3, and a light chain variable region having the polypeptide sequence of SEQ ID NO:4;
e. a heavy chain variable region having the polypeptide sequence of SEQ ID NO:5, and a light chain variable region having the polypeptide sequence of SEQ ID NO:6;
f. a heavy chain variable region having the polypeptide sequence of SEQ ID NO:7, and a light chain variable region having the polypeptide sequence of SEQ ID NO:8;
g. a heavy chain variable region having the polypeptide sequence of SEQ ID NO:9, and a light chain variable region having the polypeptide sequence of SEQ ID NO:10;
h. a heavy chain variable region having the polypeptide sequence of SEQ ID NO:11, and a light chain variable region having the polypeptide sequence of SEQ ID NO:12;
i. a heavy chain variable region having the polypeptide sequence of SEQ ID NO:13, and a light chain variable region having the polypeptide sequence of SEQ ID NO:14;
j. a heavy chain variable region having the polypeptide sequence of SEQ ID NO:15, and a light chain variable region having the polypeptide sequence of SEQ ID NO:16;
k. a heavy chain variable region having the polypeptide sequence of SEQ ID NO:17, and a light chain variable region having the polypeptide sequence of SEQ ID NO:18;
l. a heavy chain variable region having the polypeptide sequence of SEQ ID NO:19, and a light chain variable region having the polypeptide sequence of SEQ ID NO:20;
m. a heavy chain variable region having the polypeptide sequence of SEQ ID NO:21, and a light chain variable region having the polypeptide sequence of SEQ ID NO:22;
n. a heavy chain variable region having the polypeptide sequence of SEQ ID NO:23, and a light chain variable region having the polypeptide sequence of SEQ ID NO:24;
o. a heavy chain variable region having the polypeptide sequence of SEQ ID NO:25, and a light chain variable region having the polypeptide sequence of SEQ ID NO:26;
p. a heavy chain variable region having the polypeptide sequence of SEQ ID NO:27, and a light chain variable region having the polypeptide sequence of SEQ ID NO:28;
q. a heavy chain variable region having the polypeptide sequence of SEQ ID NO:29, and a light chain variable region having the polypeptide sequence of SEQ ID NO:30;
r. a heavy chain variable region having the polypeptide sequence of SEQ ID NO:31, and a light chain variable region having the polypeptide sequence of SEQ ID NO:32;
s. a heavy chain variable region having the polypeptide sequence of SEQ ID NO:35, and a light chain variable region having the polypeptide sequence of SEQ ID NO:36;
t. a heavy chain variable region having the polypeptide sequence of SEQ ID NO:37, and a light chain variable region having the polypeptide sequence of SEQ ID NO:38;
u. a heavy chain variable region having the polypeptide sequence of SEQ ID NO:39, and a light chain variable region having the polypeptide sequence of SEQ ID NO:40;
v. a heavy chain variable region having the polypeptide sequence of SEQ ID NO:282, and a light chain variable region having the polypeptide sequence of SEQ ID NO:290;
w. a heavy chain variable region having the polypeptide sequence of SEQ ID NO:282, and a light chain variable region having the polypeptide sequence of SEQ ID NO:291;

x. a heavy chain variable region having the polypeptide sequence of SEQ ID NO:282, and a light chain variable region having the polypeptide sequence of SEQ ID NO:292;
y. a heavy chain variable region having the polypeptide sequence of SEQ ID NO:283, and a light chain variable region having the polypeptide sequence of SEQ ID NO:290;
z. a heavy chain variable region having the polypeptide sequence of SEQ ID NO:283, and a light chain variable region having the polypeptide sequence of SEQ ID NO:291;
aa. a heavy chain variable region having the polypeptide sequence of SEQ ID NO:283, and a light chain variable region having the polypeptide sequence of SEQ ID NO:292;
bb. a heavy chain variable region having the polypeptide sequence of SEQ ID NO:284, and a light chain variable region having the polypeptide sequence of SEQ ID NO:290;
cc. a heavy chain variable region having the polypeptide sequence of SEQ ID NO:284, and a light chain variable region having the polypeptide sequence of SEQ ID NO:291,
dd. a heavy chain variable region having the polypeptide sequence of SEQ ID NO:284, and a light chain variable region having the polypeptide sequence of SEQ ID NO:292,
ee. a heavy chain variable region having the polypeptide sequence of SEQ ID NO:285, and a light chain variable region having the polypeptide sequence of SEQ ID NO:290,
ff. a heavy chain variable region having the polypeptide sequence of SEQ ID NO:285, and a light chain variable region having the polypeptide sequence of SEQ ID NO:291,
gg. a heavy chain variable region having the polypeptide sequence of SEQ ID NO:285, and a light chain variable region having the polypeptide sequence of SEQ ID NO:292,
hh. a heavy chain variable region having the polypeptide sequence of SEQ ID NO:283, and a light chain variable region having the polypeptide sequence of SEQ ID NO:293,
ii. a heavy chain variable region having the polypeptide sequence of SEQ ID NO:284, and a light chain variable region having the polypeptide sequence of SEQ ID NO:293,
jj. a heavy chain variable region having the polypeptide sequence of SEQ ID NO:285, and a light chain variable region having the polypeptide sequence of SEQ ID NO:293,
kk. a heavy chain variable region having the polypeptide sequence of SEQ ID NO:286, and a light chain variable region having the polypeptide sequence of SEQ ID NO:290,
ll. a heavy chain variable region having the polypeptide sequence of SEQ ID NO:286, and a light chain variable region having the polypeptide sequence of SEQ ID NO:291,
mm. a heavy chain variable region having the polypeptide sequence of SEQ ID NO:286, and a light chain variable region having the polypeptide sequence of SEQ ID NO:292;
nn. a heavy chain variable region having the polypeptide sequence of SEQ ID NO:287, and a light chain variable region having the polypeptide sequence of SEQ ID NO:294,
oo. a heavy chain variable region having the polypeptide sequence of SEQ ID NO:288, and a light chain variable region having the polypeptide sequence of SEQ ID NO:294,
pp. a heavy chain variable region having the polypeptide sequence of SEQ ID NO:289, and a light chain variable region having the polypeptide sequence of SEQ ID NO:294,
qq. a heavy chain variable region having the polypeptide sequence of SEQ ID NO:284, and a light chain variable region having the polypeptide sequence of SEQ ID NO:299,
rr. a heavy chain variable region having the polypeptide sequence of SEQ ID NO:295, and a light chain variable region having the polypeptide sequence of SEQ ID NO:299,
ss. a heavy chain variable region having the polypeptide sequence of SEQ ID NO:296, and a light chain variable region having the polypeptide sequence of SEQ ID NO:299,
tt. a heavy chain variable region having the polypeptide sequence of SEQ ID NO:297, and a light chain variable region having the polypeptide sequence of SEQ ID NO:299, or
uu. a heavy chain variable region having the polypeptide sequence of SEQ ID NO:298, and a light chain variable region having the polypeptide sequence of SEQ ID NO:299.

4. The isolated monoclonal antibody or antigen-binding fragment thereof of claim 1, wherein the monoclonal antibody or antigen-binding fragment thereof inhibits the enzyme activity of soluble and/or cell-surface CD73, prevents the dimerization of CD73, induces the internalization of CD73, and/or is capable of activating T cells.

5. The isolated monoclonal antibody or antigen-binding fragment thereof of claim 1, wherein the antibody or antigen-binding fragment thereof is chimeric or human or humanized.

6. An isolated nucleic acid encoding the monoclonal antibody or antigen-binding fragment thereof of claim 1.

7. A vector comprising the isolated nucleic acid of claim 6.

8. A host cell comprising the vector of claim 7.

9. A pharmaceutical composition, comprising the isolated monoclonal antibody or antigen-binding fragment thereof of claim 1 and a pharmaceutically acceptable carrier.

10. A method of inhibiting the nucleotidase activity of CD73, preventing the dimerization of CD73, inducing the internalization of CD73, or treating cancer in a subject in need thereof, comprising administering to the subject the pharmaceutical composition of claim 9.

11. A method of producing a monoclonal antibody or antigen-binding fragment thereof, comprising culturing the host cell of claim 8 under conditions to produce the monoclonal antibody or antigen-binding fragment thereof, and recovering the antibody or antigen-binding fragment thereof from the host cell.

12. A method of producing a pharmaceutical composition comprising the monoclonal antibody or antigen-binding fragment of claim 1, comprising combining the monoclonal antibody or antigen-binding fragment with a pharmaceutically acceptable carrier to obtain the pharmaceutical composition.

13. A method of determining a level of CD73 or determining the ecto-5' nucleotidase activity of CD73 in a subject, the method comprising:
 a. obtaining a sample from the subject;
 b. contacting the sample with an isolated monoclonal antibody or antigen-binding fragment thereof of claim 1; and
 c. determining a level of CD73 or determining the ecto-5' nucleotidase activity of CD73 in the subject.

14. The method of claim 13, wherein the sample is a tissue sample or a blood sample.

15. The method of claim 14, wherein the tissue sample is a cancer tissue sample.

16. An isolated bispecific antibody or antigen-binding fragment thereof comprising the monoclonal antibody or antigen-binding fragment thereof of claim 1.

17. An isolated nucleic acid encoding the bispecific antibody or antigen-binding fragment thereof of claim 16.

18. A vector comprising the isolated nucleic acid of claim 17.

19. A host cell comprising the vector of claim 18.

20. A pharmaceutical composition comprising the isolated bispecific antibody or antigen-binding fragment thereof of claim 16 and a pharmaceutically acceptable carrier.

\* \* \* \* \*